United States Patent
Herdewijn et al.

(10) Patent No.: US 8,338,435 B2
(45) Date of Patent: Dec. 25, 2012

(54) SUBSTITUTED PYRIDO(3,2-D) PYRIMIDINES AND PHARMACEUTICAL COMPOSITIONS FOR TREATING VIRAL INFECTIONS

(75) Inventors: Piet André Maurits Maria Herdewijn, Rotselaar/Wezemaal (BE); Steven Cesar Alfons De Jonghe, Brussels (BE); William John Watkins, Saratoga, CA (US); Lee Shun Chong, Newark, CA (US); Jennifer Zhang, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 644 days.

(21) Appl. No.: 12/374,223

(22) PCT Filed: Jun. 20, 2007

(86) PCT No.: PCT/BE2007/000088
§ 371 (c)(1),
(2), (4) Date: Mar. 26, 2009

(87) PCT Pub. No.: WO2008/009076
PCT Pub. Date: Jan. 24, 2008

(65) Prior Publication Data
US 2009/0253696 A1    Oct. 8, 2009

Related U.S. Application Data

(60) Provisional application No. 60/807,920, filed on Jul. 20, 2006.

(51) Int. Cl.
*A61K 31/517* (2006.01)
*C07D 471/00* (2006.01)
(52) U.S. Cl. .................... 514/258.1; 544/279
(58) Field of Classification Search .................. 514/258, 514/258.1; 544/279
See application file for complete search history.

(56) References Cited

U.S. PATENT DOCUMENTS

| | | |
|---|---|---|
| 2,512,572 A | 6/1950 | Smith, Jr. et al. |
| 2,924,599 A | 2/1960 | Oakes et al. |
| 3,843,638 A | 10/1974 | Nicki et al. |
| 3,939,268 A | 2/1976 | Nickl et al. |
| 3,952,001 A | 4/1976 | Brookes et al. |
| 3,969,268 A | 7/1976 | Fukuda et al. |
| 4,460,591 A | 7/1984 | Degraw et al. |
| 4,492,597 A | 1/1985 | Aoki et al. |
| 4,818,819 A | 4/1989 | Taylor et al. |
| 5,167,963 A | 12/1992 | Degraw et al. |
| 5,223,503 A | 6/1993 | Gossett et al. |
| 5,508,281 A | 4/1996 | Gangjee |
| 5,521,190 A | 5/1996 | Henrie et al. |
| 5,547,954 A | 8/1996 | Henrie, II et al. |
| 5,654,307 A | 8/1997 | Bridges et al. |
| 5,780,462 A | 7/1998 | Lee et al. |
| 6,331,547 B1 | 12/2001 | Zhu et al. |
| 6,440,991 B1 | 8/2002 | Zhu et al. |
| 6,476,031 B1 | 11/2002 | Chakravarty et al. |
| 6,521,620 B1 | 2/2003 | Bridges et al. |
| 6,562,818 B1 | 5/2003 | Bridges et al. |
| 6,713,484 B2 | 3/2004 | Bridges et al. |
| 6,723,726 B1 | 4/2004 | Cockeril et al. |
| 6,730,682 B2 | 5/2004 | Schnute et al. |
| 6,946,465 B2 | 9/2005 | Waer et al. |
| 6,962,920 B2 | 11/2005 | Gangjee |
| 6,974,808 B2 | 12/2005 | McCarthy |
| 7,074,799 B2 | 7/2006 | Bakthavatchalam et al. |
| 7,276,506 B2 | 10/2007 | Waer et al. |
| 7,501,513 B2 | 3/2009 | Waer et al. |
| 2002/0049207 A1 | 4/2002 | McCarthy |
| 2003/0199526 A1 | 10/2003 | Choquette et al. |
| 2003/0236255 A1 | 12/2003 | Waer et al. |

(Continued)

FOREIGN PATENT DOCUMENTS

DE    21 17 657    10/1972

(Continued)

OTHER PUBLICATIONS

Patani et al. "Bioisosterism: A rational approch in drug design," Chem. Rev. 1996, vol. 96, pp. 3147-3176.*
West, Solid state chemistry and its application, Wilsy, New York, 1988. pp, 358, 365.*
Ulrich "Crystallization," Chapter 4, Kirk-Othmer Encyclopedia of Chemical techology, John, Wiley and Sons, 2002.*
Testa "Prodrug research: Futile or fertile?" Biochemical Pharmacology, 2004, vol. 68, pp. 2097-2106.*
Hayakawa et al., Synthesis and Biological Evaluation of 4-morpholino-2-phenylquinazolines and Related Derivatives as Novel PI3 Kinase p110α Inhibitors, *Bioorganic & Medicinal Chemistry*, 14: 6847-6858, 2006.

(Continued)

*Primary Examiner* — Shengjun Wang
(74) *Attorney, Agent, or Firm* — Clark & Elbing LLP

(57) ABSTRACT

This invention provides di-, tri- and tetra-substituted pyrido (3,2-d)pyrimidine derivatives with specific substituting patterns, their pharmaceutically acceptable salts, N-oxides, solvates, pro-drugs and enantiomers, possessing unexpectedly desirable pharmaceutical properties, in particular being highly active antiviral agents. The invention also provides use of such derivatives in the treatment of viral infections and pathologic conditions associated therewith, including hepatitis C.

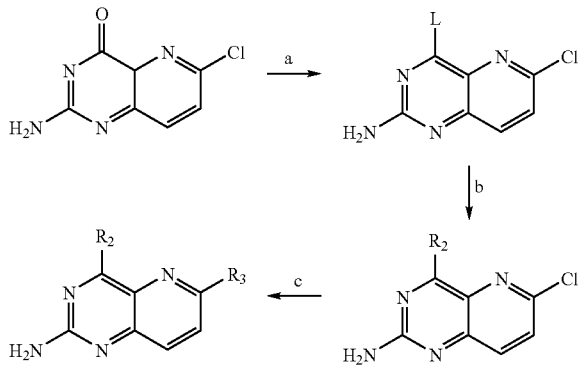

20 Claims, 4 Drawing Sheets

U.S. PATENT DOCUMENTS

| | | |
|---|---|---|
| 2004/0039000 A1 | 2/2004 | Gangjee |
| 2004/0077859 A1 | 4/2004 | Waer et al. |
| 2004/0106616 A1 | 6/2004 | Bakthavatchalam et al. |
| 2005/0014771 A1 | 1/2005 | Hayakawa et al. |
| 2006/0189620 A1 | 8/2006 | Waer et al. |
| 2006/0287314 A1 | 12/2006 | Waer et al. |
| 2007/0004721 A1 | 1/2007 | Waer et al. |
| 2007/0032477 A1 | 2/2007 | Waer et al. |
| 2007/0043000 A1 | 2/2007 | Waer et al. |
| 2008/0004285 A1 | 1/2008 | De Jonghe et al. |
| 2008/0182870 A1 | 7/2008 | Bondy et al. |
| 2008/0312227 A1 | 12/2008 | De Jonghe et al. |
| 2009/0036430 A1 | 2/2009 | De Jonghe et al. |
| 2009/0131414 A1 | 5/2009 | De Jonghe et al. |
| 2009/0285782 A1 | 11/2009 | Gao et al. |
| 2009/0318456 A1 | 12/2009 | Herdewijn et al. |
| 2010/0143299 A1 | 6/2010 | Gao et al. |
| 2010/0168416 A1 | 7/2010 | Goff et al. |
| 2010/0305117 A1 | 12/2010 | Herdewijn et al. |

FOREIGN PATENT DOCUMENTS

| | | |
|---|---|---|
| DE | 2 202 367 A1 | 8/1973 |
| DE | 2 208 535 A1 | 8/1973 |
| EP | 0 265 126 | 4/1988 |
| EP | 1 277 738 | 1/2003 |
| GB | 2 120 665 A | 12/1983 |
| WO | WO 94/27439 | 12/1994 |
| WO | WO 99/43681 | 2/1999 |
| WO | WO 99/43682 | 2/1999 |
| WO | WO 00/12497 | 3/2000 |
| WO | WO 01/83456 | 11/2001 |
| WO | WO 02/00623 | 1/2002 |
| WO | WO 02/22607 | 3/2002 |
| WO | WO 0222602 | 3/2002 |
| WO | WO03062209 | 7/2003 |
| WO | WO 03/097615 | 11/2003 |
| WO | WO 2004/010929 | 2/2004 |
| WO | WO 2004/055004 | 7/2004 |
| WO | WO 2005/065691 | 7/2005 |
| WO | WO 2006039718 | 4/2006 |
| WO | WO/2006/069805 | 7/2006 |
| WO | WO 2006/087229 A1 | 8/2006 |
| WO | WO/2006/090169 | 8/2006 |
| WO | WO/2006/135993 | 12/2006 |
| WO | WO 2007/076092 | 7/2007 |
| WO | WO 2007117394 | 10/2007 |
| WO | WO 2008/009079 A2 | 1/2008 |
| WO | WO 2008/077651 A1 | 7/2008 |
| WO | WO 2009/003669 A2 | 1/2009 |

OTHER PUBLICATIONS

Invitation to pay Additional Fees (PCT/BE2007/000088) mailed Mar. 4, 2008.

International Search Report (PCT/BE2007/000088) mailed Aug. 8, 2008.

Written Opinion of the International Searching Authority (PCT/BE2007/000088) mailed Aug. 8, 2008.

Response to Written Opinion of Aug. 8, 2008 (PCT/BE2007/000088) mailed Oct. 27, 2008.

Vema et al., "Design of EGFR Kinase Inhibitors: A Ligand-Based Approach and its Confirmation with Structure-Based Studies," *Bioorg. Med. Chem.* 11:4643-4653 (2003).

International Preliminary Report on Patentability for PCT/BE2007/000088 mailed Feb. 23, 2009.

U.S. Appl. No. 13/176,627, filed Jul. 5, 2011, Herdewijn et al.

Colbry et al., "Synthesis and Antimalarial Properties of 2,4-Diamino-6-[(aryl)thio, sulfinyl, and sulfonyl]pyrido[3,2-*d*]pyrimidines," *J. Heterocyclic Chem.* 21:1521-1525, 1984.

Di Giacomo et al., "Synthesis and Biological Activity of New Melatonin Dimeric Derivatives," *Biorg. Med. Chem.* 15:4643-4650, 2007.

Durucasu, "Investigation of Different Synthetic Ways for Protection of 6-Bromo-5-Deazapterin," *Doğa Tu J. Chem.* 13:280-292, 1989.

Griesser, "The Importance of Solvates," in *Polymorphism: In the Pharmaceutical Industry* Hilfiker (Ed.), Wiley-VCH, Verlag GmbH & Co. KgaA, Weinheim, Ch. 8 (pp. 211-233), 2006.

Kuwada et al., "A New Synthesis of 6-Substituted Pyrido[2,3-*d*]Pyrimidines," *Heterocycles* 57:2081-2090, 2002.

Taylor et al., "A Convenient Synthesis of 6-Formyl-5-Deazapterin," *Synth. Commun.* 18:1187-1191, 1988.

Taylor et al., "Convergent and Efficient Palladium-Effected Synthesis of 5,10-Dideaza-5,6,7,8-tetrahydrofolic Acid (DDATHF)," *J. Org. Chem.* 54:3618-3624, 1989.

Taylor et al., "Protection and Deprotection of Fused 2-Amino-4(3H)-Pyrimidinones: Conversion of Pterins and 5-Deazapterins to 2,4-Diamino Derivatives," *Heterocycles* 36:1883-1895, 1993.

Temple, Jr. et al., "Synthesis of Potential Antimalarial Agents. VIII. Azaquinolines. II. Preparation of Some 1, 5-Naphthyridines and Pyrido [3, 2-*d*] pyrimidines," *J. Heterocyclic Chem.* 7:1219-1222, 1970.

Vippagunta et al., "Crystalline Solids," *Adv. Drug Del. Rev.* 48: 3-26, 2001.

* cited by examiner

SUBSTITUTED PYRIDO(3,2-D) PYRIMIDINES AND PHARMACEUTICAL COMPOSITIONS FOR TREATING VIRAL INFECTIONS

CROSS-REFERENCE TO RELATED APPLICATIONS

This application is the U.S. National Stage of International Application No. PCT/BE2007/000088, filed Jul. 20, 2007, which, in turn, claims the benefit of U.S. Provisional Application Ser. No. 60/807,920, filed Jul. 20, 2006.

The present invention relates to a class of novel substituted pyrido(3,2-d) pyrimidine derivatives and methods for their preparation, as well as to pharmaceutical compositions comprising one or more of said novel substituted pyrido(3,2-d) pyrimidine derivatives and one or more pharmaceutically acceptable excipients. The present invention further relates to the use of said novel pyrido(3,2-d)pyrimidine derivatives as biologically active ingredients, more specifically for the manufacture of medicaments for the prevention and treatment of viral infections by a virus of the Flaviridae family, more specifically for inhibiting replication of hepatitis C virus. The present invention thus also relates to therapeutic and prophylactic methods against viral infections and pathologic conditions associated therewith, comprising the administration of said specifically substituted pyrido(3,2-d)pyrimidine derivatives, or pro-drugs thereof, to mammals, in particular human beings.

BACKGROUND OF THE INVENTION

A huge number of pyrido(3,2-d)pyrimidine derivatives is already known in the art. For instance pyrido(3,2-d)pyrimidine derivatives with various substituents on positions 2, 4 and 6 (using the standard atom numbering for the pyrido(3,2-d)pyrimidine moiety) are known with biological activities such as competitive inhibition of pteroylglutamic acid, inhibition of thrombocyte aggregation and adhesiveness, antineoplastic activity, inhibition of dihydrofolate reductase and thymidylate synthase, e.g. from U.S. Pat. No. 2,924,599, U.S. Pat. No. 3,939,268, U.S. Pat. No. 4,460,591, U.S. Pat. No. 5,167,963 and U.S. Pat. No. 5,508,281.

Pyrido(3,2-d)pyrimidine derivatives with various substituents on positions 2, 4, 6 and 7 (using the standard atom numbering for the pyrido(3,2-d)pyrimidine moiety) are also known e.g. from U.S. Pat. No. 5,521,190, U.S. patent application publication No. 2002/0049207, U.S. patent application publication No. 2003/0186987, U.S. patent application publication No. 2003/0199526, U.S. patent application publication No. 2004/0039000, U.S. patent application publication No. 2004/0106616, U.S. Pat. No. 6,713,484, U.S. Pat. No. 6,730,682 and U.S. Pat. No. 6,723,726. Some of them show activities as antiviral agents, anti-cancer agents, EGF inhibitors, inhibitors of GSK-3 protein kinases and the like.

U.S. Pat. No. 5,654,307 discloses pyrido(3,2-d)pyrimidine derivatives which are substituted on position 4 with monoarylamino or monobenzylamino, and on positions 6 and 7 with substituents each independently selected from the group consisting of lower alkyl, amino, lower alkoxy, mono- or dialkylamino, halogen and hydroxy. WO 01/083456 discloses pyrido(3,2-d)pyrimidine derivatives which are substituted on position 4 with morpholinyl and on position 2 with hydroxyphenyl or morpholinoethoxyphenyl, having PI3K and cancer inhibiting activity. U.S. Pat. No. 6,476,031 generically discloses substituted quinazoline derivatives, including (in reaction scheme 5) a series of pyrido(3,2-d)pyrimidine derivatives which are substituted on position 4 with hydroxy, chloro or an aryl, heteroaryl (including pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl), cycloaliphatic or cycloheteroaliphatic group being optionally spaced from the pyrido(3,2-d)pyrimidine ring by a linker such as NH. WO 02/22602 and WO 02/22607 disclose pyrazole and triazole compounds, including 2-(1-trifluoromethylphenyl)-4-fluorobenzopyrazolyl-pyrido(3,2-d)pyrimidine and 2-(1-trifluoromethylphenyl)-4-methyltriazolyl-pyrido(3,2-d)pyrimidine being useful as protein kinase inhibitors. WO 03/062209 discloses pyrido(3,2-d)pyrimidine derivatives which are substituted on position 7 with aryl or heteroaryl and on position 4 with monoarylamino or monoheteroarylamino and which may further be substituted on positions 2 and/or 6, being useful as capsaicin receptor modulators. However none of these documents teaches or suggests pyrido(3,2-d)pyrimidine derivatives having the substitution pattern disclosed by the present invention.

There is a continuous need in the art for specific and highly therapeutically active compounds for preventing or treating infections due to Flaviridae and pathologic conditions associated therewith, especially hepatitis C. In particular, there is a need in the art to provide drugs which are active against hepatitis C in a minor dose in order to replace existing drugs having significant side effects and to decrease treatment costs.

Hepatitis is an inflammation of the liver that is most often caused by infection with one of three viruses known as hepatitis. A, B or C. Hepatitis A virus (HAV) infection is the most common cause of acute hepatitis, and usually resolves spontaneously after several weeks of acute symptoms. Hepatitis B virus (HBV) and hepatitis C virus (HCV) are the most common viral causes of chronic hepatitis, usually defined as liver inflammation persisting for more than six months. HCV is the second most common cause of viral hepatitis in general and most common cause of chronic hepatitis. The World Health Organization estimates that worldwide 170 million people (3% of the world's population) are chronically infected with HCV. These chronic carriers are at risk of developing cirrhosis and/or liver cancer. In studies with a 10 to 20 year follow-up, cirrhosis developed in 20-30% of the patients, 1-5% of whom may develop liver cancer subsequently. The 15% to 45% of persons with acute hepatitis C who do recover are not subject to long-term complications and do not need treatment. Since HCV and pestiviruses belong to the same virus family and share many similarities (such as, but not limited to, organization of the genome, analogous gene products and replication cycle), pestiviruses may be adopted as a model virus and surrogate for HCV. For example the Bovine Viral Diarrhea Virus (BVDV) is closely related to hepatitis C virus (HCV) and may be used as a surrogate virus in drug development for HCV infection.

HCV is a representative and highly significant member of the Flaviviridae family, a family of positive-strand RNA viruses. This family includes the following genera: Genus *Flavivirus* (type species Yellow fever virus, others include West Nile virus and Dengue Fever), Genus *Hepacivirus* (type species Hepatitis C virus), and Genus *Pestivirus* (type species Bovine viral diarrhea virus (BVDV), others include classical swine fever or hog cholera). Contrary to other families of positive strand RNA viruses such as human immunodeficiency virus (HIV), HCV seems incapable of integrating into the host's genome. The primary immune response to HCV is mounted by cytotoxic T lymphocytes. Unfortunately, this process fails to eradicate infection in most people; in fact, it may contribute to liver inflammation and, ultimately, tissue necrosis. The ability of HCV to escape immune surveillance is the subject of much speculation. One likely means of viral persistence relies on the presence of closely related but heterogeneous populations of viral genomes. Further studies of these quasi-species enable classification of several genotypes and subtypes, which have clinical implications.

The diagnosis of hepatitis C is rarely made during the acute phase of the disease because the majority of people infected experience no symptoms during this phase of the disease. Those who do experience acute phase symptoms are rarely ill enough to seek medical attention. The diagnosis of chronic phase hepatitis C is also challenging due to the absence or lack of specificity of symptoms until advanced liver disease develops, which may not occur until decades into the disease.

Hepatitis C testing begins with serological blood tests used to detect antibodies to HCV. Anti-HCV antibodies can be detected in about 80% of patients within 15 weeks after exposure, in more than 90% of patients within 5 months after exposure, and in more than 97% of patients by 6 months after exposure. Overall, HCV antibody tests have a strong positive predictive value for exposure to the hepatitis C virus, but may miss patients who have not yet developed antibodies (seroconversion), or have an insufficient level of antibodies to detect. Anti-HCV antibodies indicate exposure to the virus, but cannot determine if ongoing infection is present. All persons with positive anti-HCV antibody tests must undergo additional testing for the presence of the hepatitis C virus itself to determine whether current infection is present. The presence of HCV may be tested by using molecular nucleic acid testing methods such as, but not limited to, polymerase chain reaction (PCR), transcription mediated amplification (TMA), or branched DNA amplification. All HCV nucleic acid molecular tests have the capacity to detect not only whether the virus is present, but also to measure the amount of virus present in the blood (the HCV viral load). The HCV viral load is an important factor in determining the probability of response to interferon-base therapy, but does not indicate disease severity nor the likelihood of disease progression.

The goal of treatment is to prevent complications of HCV infection. This is principally achieved by eradication of infection. Accordingly, treatment responses are frequently characterized by the results of HCV RNA testing. Infection is considered eradicated when there is a sustained virologic response (SVR), defined as the absence of HCV RNA in serum by a sensitive test at the end of treatment and 6 months later. Persons who achieve an SVR almost always have a dramatic earlier reduction in the HCV RNA level, referred to as an early virologic response (EVR). Continued absence of detectable virus at termination of treatment is referred to as end of treatment response (ETR). A patient is considered relapsed when HCV RNA becomes undetectable on treatment but is detected again after discontinuation of treatment. Persons in whom HCV RNA levels remain stable on treatment are considered as non-responders, while those whose HCV RNA levels decline but remain detectable are referred to as partial responders.

Current standard of care for HCV treatment is a combination of (pegylated) interferon alpha and the antiviral drug ribavirin for a period of 24 or 48 weeks, depending upon the viral genotype. Should treatment with pegylated ribavirin-interferon not return a viral load reduction after 12 weeks, the chance of treatment success is less than 1%. Current indication for treatment includes patients with proven hepatitis C virus infection and persistent abnormal liver function tests. SVR of 75% or better occur in people with genotypes HCV 2 and 3 within 24 weeks of treatment, about 50% in those with genotype 1 within 48 weeks of treatment and 65% for those with genotype 4 within 48 weeks of treatment. About 80% of hepatitis C patients in the United States exhibit genotype 1, whereas genotype 4 is more common in the Middle East and Africa.

Best results have been achieved with the combination of weekly subcutaneous injections of long-acting peginterferon alpha and oral ribavirin daily. Interferons are substances naturally released by cells in the body after viral invasion. Interferon alfa-2b and peginterferon alfa-2b are synthetic versions of these substances. The protein product is manufactured by recombinant DNA-technology. Second generation interferons are further derivatized by binding to inert polyethylene glycol, thereby altering the pharmacokinetic properties. Ribavirin is a nucleoside analogue, which disrupts viral replication of hepatitis C virus (HCV).

The most common side effects of HCV treatment with (pegylated) interferon include: a decrease in white blood cells and platelets, anemia, nausea, diarrhea, fever, chills, muscle and joint pain, difficulty in concentrating, thyroid dysfunction, hair loss, sleeplessness, irritability, mild to serious depression, and rarely, suicidal thoughts. Other serious adverse events include bone marrow toxicity, cardiovascular disorders, hypersensitivity, endocrine disorders, pulmonary disorders, colitis, pancreatitis, and opthalmologic disorders (eye and vision problems). (Pegylated) interferon may also cause or make worse fatal or life-threatening neuropsychiatric, autoimmune, ischemic, and infectious disorders. Patients with persistently severe or worsening signs or symptoms of these conditions are advised to stop therapy.

The most common side effect of HCV treatment with ribavirin is anemia, which can be treated with erythropoietin. Other side effects include mood swings, irritability, anxiety, insomnia, abdominal pain, nervousness, breathlessness, rash, hair loss, dry skin, nausea, diarrhoea, loss of appetite, dizziness and weight loss. Ribavirin can also cause birth defects. Ribavirin should not be taken in combination with certain HIV drugs such as, but not limited to, didanosine, since lactic acidosis with fatal hepatic steatosis (fatty liver) may occur. Special attention should be taken for treatment with HIV co-infection.

Although the liver is the primary target of infection, studies to better define the steps of HCV infection are greatly hampered by the lack of a suitable animal model for such studies. The recent development of sub-genomic HCV RNA replicons capable of autonomous replication in the human hepatoma cell line, Huh-7, has been a significant advance in the study of HCV biology. The sub-genomic HCV RNA replicon system provides a cell-based assay to evaluate inhibitors of HCV enzymes like the protease, helicase, and RNA-dependant RNA polymerase or to evaluate nucleic acid targeting strategies like antisense RNA and ribozymes.

Targets for HCV Drug development include HCV-encoded enzymes, namely, NS2-3 and NS3-4A proteases, NS3 helicase, and NS5B RNA dependant RNA polymerase. Alternatively, HCV replication can be inhibited by blocking the conserved RNA elements employing a nucleic acid based approach including antisense oligo-nucleotides, ribozymes, RNA aptamers, RNA decoys, and RNA interference. A major drawback for such nucleic acid based approach is the size and charge of the nucleic acids, and their usually low physiological stability that do not allow for oral administration. Another target option for therapy is by blocking viral entry into the cell by obstruction of binding to HCV receptors such as, but not limited to, CD 209L and L-SIGN.

There is a strong need in the art to improve, or to provide alternatives to, the existing prophylactic or therapeutic solutions to infections by a virus of the Flaviridae family, more specifically HCV infection. In particular there is still a need in the art for providing alternative synthetic molecules having significant HCV replication inhibiting activity. There is also a need in the art for providing effective inhibiting molecules which are free from the significant drawbacks of the current drugs like pegylated interferon and ribavirin. Meeting these various needs in the art constitutes the main goal of the present invention.

SUMMARY OF THE INVENTION

The present invention is based on the unexpected finding that pyrido(3,2-d)pyrimidine derivatives with certain combinations of substituents on positions 2, 4, 6 and/or 7 (using the standard atom numbering for the pyrido(3,2-d)pyrimidine moiety) which are not suggested by the prior art, in particular but not limited to certain 2-amino-4-hydrocarbyl-6-aryl-pyrido(3,2-d)pyrimidines and 2-amino-4-hydrocarbyl-6-heteroaryl-pyrido(3,2-d)pyrimidines, are able to meet one or more of the needs recited herein above, in particular have a significant HCV replication inhibiting activity.

Based on this finding the present invention relates, in one aspect, to a class of di-, tri- and tetra-substituted pyrido(3,2-d)pyrimidine derivatives represented by the structural formula (I):

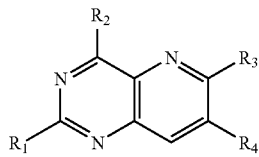

wherein:
R$_1$ is selected from the group consisting of hydrogen; halogen; cyano; carboxylic acid; acyl; thioacyl; C$_{1-7}$ alkoxycarbonyl; acyloxy; carbonate; carbamate; C$_{1-7}$ alkyl; aryl; amino; acylamino; thioacylamino; N-protected amino; (mono- or di-) C$_{1-7}$ alkylamino; (mono- or di-) arylamino; (mono- or di-) C$_{3-10}$ cycloalkylamino; (mono- or di-) hydroxy C$_{1-7}$ alkylamino; (mono- or di-) C$_{1-7}$ alkyl-arylamino; mercapto C$_{1-7}$ alkyl; C$_{1-7}$ alkyloxy; and groups having the structural formula R$_6$—NR$_7$R$_{12}$ wherein R$_6$ is a bond or C$_{1-7}$ alkylene and wherein R$_7$ and R$_{12}$ are independently selected from the group consisting of hydrogen, C$_{1-7}$ alkyl, C$_{2-7}$ alkenyl, C$_{2-7}$ alkynyl, aryl C$_{1-7}$ alkyl, C$_{3-10}$ cycloalkyl, aryl and heteroaryl, said aryl or heteroaryl being optionally substituted with one or more substituents independently selected from the group consisting of halogen and C$_{1-7}$ alkyl, and said C$_{3-10}$ cycloalkyl being optionally substituted, at the carbon position adjacent to the nitrogen atom to which it is attached, with aryl or heteroaryl wherein said aryl or heteroaryl is optionally substituted with halogen, or wherein R$_7$ and R$_{12}$ together with the nitrogen to which they are attached form a heterocyclyl group; and groups having the structural formula —NH—CHR$_8$R$_8$' wherein R$_8$ is selected from the group consisting of C$_{1-7}$ alkyl substituted with one or more substituents independently selected from the group consisting of halogen and C$_{1-7}$ alkoxy, C$_{3-10}$ cycloalkyl, aryl substituted with one or more R$_{14}$, and heterocyclyl, and wherein R$_8$' is selected from the group consisting of hydrogen, C$_{1-7}$ alkyl optionally substituted with one or more substituents independently selected from the group consisting of halogen and C$_{1-7}$ alkoxy, C$_{3-10}$ cycloalkyl, aryl optionally substituted with one or more R$_{14}$, and heterocyclyl;

R$_2$ is selected from the group consisting of C$_{1-14}$ alkyl, C$_{2-7}$ alkenyl, C$_{2-7}$ alkynyl, halo C$_{1-7}$ alkyl, hydroxy C$_{1-7}$ alkyl, C$_{1-7}$ alkoxy-C$_{1-7}$ alkyl, arylalkenyl, C$_{3-10}$ cycloalkyl, heterocyclyl (in particular heteroaryl), heterocyclyl-C$_{1-7}$ alkyl, C$_{3-10}$ cycloalkyl-C$_{1-7}$ alkyl, aryl and aryl-C$_{1-7}$ alkyl, wherein the aryl moiety of said aryl or aryl-C$_{1-7}$ alkyl is optionally substituted with one or more substituents independently selected from the group consisting of halogen, C$_{1-7}$ alkoxy and C$_{1-7}$ alkyl;

R$_3$ and R$_4$ are each independently selected from the group consisting of hydrogen halogen, heterocyclyl (in particular heteroaryl) and aryl, wherein said heterocyclyl (in particular heteroaryl) or aryl is optionally substituted with one or more substituents independently selected from the group consisting of halogen, C$_{1-7}$ alkyl, C$_{2-7}$ alkenyl, C$_{2-7}$ alkynyl, halo C$_{1-7}$ alkyl, C$_{3-10}$ cycloalkyl, aryl, nitro, hydroxyl, sulfhydryl, amino, C$_{1-7}$ alkoxy, C$_{3-10}$ cycloalkoxy, aryloxy, aryl-C$_{1-7}$ alkoxy, oxyheterocyclic, heterocyclic-substituted alkyloxy, thio-C$_{1-7}$ alkyl, thio-C$_{3-10}$ cycloalkyl, thioaryl, thio-heterocyclyl, arylalkylthio, heterocyclyl-C$_{1-7}$ alkylthio, formyl, —CO—NHR$_9$, —CO—NR$_9$R$_9$', —CS—NHR$_9$, —NR$_{13}$—CO—NHR$_{13}$, —NR$_{13}$—CS—NHR$_{13}$, —SO$_2$NH$_2$, —NR$_{13}$—SO$_2$R$_{11}$, —NR$_{13}$—COR$_{10}$, —NR$_{13}$—CSR$_{10}$, hydroxylamino, C$_{1-7}$ alkoxyamino, mercaptoamino, thioalkylamino, cyano, carboxylic acid or esters or thioesters or halides or anhydrides or amides thereof, thiocarboxylic acid or esters or thioesters or halides or anhydrides or amides thereof, C$_{1-7}$ alkylamino, C$_{3-10}$ cycloalkylamino, C$_{2-7}$ alkenylamino, C$_{3-10}$ cycloalkenylamino, C$_{2-7}$ alkynylamino, arylamino, arylC$_{1-7}$alkylamino, hydroxy C$_{1-7}$alkylamino, mercapto C$_{1-7}$ alkylamino, heterocyclylamino, C$_{1-7}$ alkylsulfoxide, C$_{1-7}$ alkylsulfone, hydrazino, C$_{1-7}$ alkylhydrazino, phenylhydrazino, and heterocyclyl optionally substituted with one or more substituents independently selected from the group consisting of hydroxy, oxo, halogen, amino, C$_{1-7}$ alkyl and C$_{1-7}$ alkoxy;

or R$_3$ and R$_4$ are independently selected from the group consisting of hydrogen; aryl being substituted with one or more substituents independently selected from the group consisting of aryl optionally substituted with arylcarbonyl, (O,O-dialkylphosphonyl)-C$_{1-7}$ alkyl, acyl, halo-C$_{1-7}$ alkoxy, hydroxy-C$_{1-7}$ alkoxy, hydroxy-C$_{1-7}$ alkyl, di-(C$_{1-7}$ alkyl)amino C$_{1-7}$ alkyl, ω-carboxy-acylamino, mono-C$_{3-7}$ cycloalkylaminocarbonyl, di-(C$_{3-7}$ cyclo-alkyl)aminocarbonyl, mono-(C$_{1-7}$ alkyl)aminocarbonyl, mono-(ω-dimethylamino-C$_{1-7}$ alkyl)aminocarbonyl, (di-C$_{1-7}$ alkyl)aminocarbonyl, mono-(hydroxy-C$_{1-7}$ alkyl)-aminocarbonyl, formylamino, —SO$_2$NH$_2$, arylamino-C$_{1-17}$ alkyl, C$_{1-7}$ alkylsulfonyl, heterocyclyl-carbonyl, heterocyclyl-C$_{1-7}$ alkyl or heterocyclyl, wherein said heterocyclyl is optionally substituted with C$_{3-7}$ alkenyloxycarbonyl, C$_{1-7}$ alkyl or C$_{1-7}$ alkyloxycarbonyl; fused benzo-C$_{5-8}$ cycloalkyl optionally substituted with oxo; and heterocyclyl substituted with one or more substituents independently selected from the group consisting of acylamino, C$_{1-7}$ alkylsulfonyl, arylsulfonyl, heterocyclyl-C$_{1-7}$ alkyl, heterocyclyl-C$_{1-7}$ alkylamino, aryl and heterocyclyl, wherein the latter heterocyclyl is optionally substituted with C$_{1-7}$ alkyl, arylsulfonyl or (di-C$_{1-7}$ alkylamino)-C$_{1-7}$ alkoxy, or said heterocyclyl is non-aromatic and includes a nitrogen atom substituted with heterocyclyl-C$_{1-7}$ alkyl or a carboxylic acid or a $C_{1-7}$ alkyl ester thereof; provided that $R_3$ and $R_4$ are not both hydrogen;

$R_9$ and $R_9'$ are each independently selected from the group consisting of hydrogen; $C_{3-10}$ cycloalkyl optionally substituted with one or more substituents independently selected from the group consisting of cyano, halogen, hydroxy, amino, $C_{1-7}$ alkyl and $C_{1-7}$ alkoxy; $C_{1-7}$ alkoxy; $C_{1-7}$ alkyl optionally substituted with one or more substituents independently selected from the group consisting of amino-$C_{1-7}$ alkylamino, cyano, di-($C_{1-7}$ alkyl) amino, halogen, and heterocyclyl optionally substituted with $C_{1-7}$ alkyl; aryl and aryl$C_{1-7}$alkyl wherein the aryl moiety is optionally substituted with one or more halogens; or $R_9$ and $R_9'$ together with the nitrogen atom to which they are attached form a heterocyclyl group;

each $R_{10}$ and each $R_{11}$ is independently selected from the group consisting of $C_{1-7}$ alkyl optionally substituted with one or more substituents independently selected from the group consisting of amino, cyano, halogen and hydroxy; $C_{1-7}$ alkoxy optionally substituted with one or more substituents independently selected from the group consisting of amino, mono-($C_{1-7}$ alkyl)amino, cyano, di-($C_{1-7}$ alkyl)amino, halogen, and heterocyclyl optionally substituted with one or more substituents independently selected from the group consisting of $C_{1-7}$ alkyl, acylamino and oxo; $C_{3-10}$ cycloalkyl optionally substituted with one or more substituents independently selected from the group consisting of amino and hydroxy; and amino optionally substituted with one or more substituents independently selected from the group consisting of $C_{1-7}$ alkyl wherein said $C_{1-7}$ alkyl is optionally substituted with one or more substituents independently selected from the group consisting of amino, mono-($C_{1-7}$ alkyl)amino, cyano, di-($C_{1-7}$ alkyl) amino, halogen and heterocyclyl;

each $R_{13}$ is hydrogen or $C_{1-7}$ alkyl optionally substituted with one or more substituents independently selected from the group consisting of cyano, halogen and hydroxy;

each $R_{14}$ is independently selected from the group consisting of halogen, hydroxy, amino, nitro, cyano, halo $C_{1-7}$ alkyl, halo $C_{1-7}$ alkoxy, $C_{1-7}$ alkyl, $C_{1-7}$ alkoxy, di-($C_{1-7}$ alkyl)amino, mono-($C_{1-7}$ alkyl)amino, carboxamido, —$SO_2NH_2$, carbamoyl, —$NR_{13}$—$SO_2R_{11}$ and phenoxy, or a pharmaceutical acceptable addition salt or a stereochemical isomeric form thereof or a N-oxide thereof or a solvate thereof or a pro-drug form thereof, provided said pyrido(3,2-d)pyrimidine derivative is not 2-amino-4-n-propyl-6-(4-fluorophenyl)-pyrido(3,2-d)pyrimidine.

Within the above defined class of pyrido(3,2-d)pyrimidine compounds, a particular embodiment of the present invention is one wherein $R_1$ is not hydrogen, i.e. position 2 of the pyrido(3,2-d)pyrimidine moiety is substituted. Another particular embodiment of pyrido(3,2-d)pyrimidine derivatives of the present invention is one wherein $R_1$ is amino or N-protected amino such as, but not limited to, acylamino, e.g. acetamido or pivalamido. Another particular embodiment of pyrido(3,2-d)pyrimidine derivatives according to the present invention is one wherein $R_1$ is amino or N-protected amino (such as specified above), and further wherein $R_4$ is hydrogen and $R_3$ is a substituted aryl group, e.g. a phenyl group having a single substituent wherein e.g. said single substituent is in para position onto said phenyl group, or a phenyl group having two identical or different substituents. Another particular embodiment of pyrido(3,2-d)pyrimidine derivatives according to the present invention is one wherein $R_1$ is amino or N-protected amino (such as specified above), and wherein $R_3$ is a phenyl group substituted with fluoro or acetamido. Another particular embodiment of pyrido(3,2-d)pyrimidine derivatives according to the present invention is one wherein $R_1$ is amino or N-protected amino (such as specified above), and further wherein $R_4$ is hydrogen and $R_3$ is a substituted heteroaryl group, e.g. a pyridinyl or pyrimidinyl group, having a single substituent or a heteroaryl group, e.g. a pyridinyl or pyrimidinyl group, having two identical or different substituents. Another particular embodiment of pyrido(3,2-d) pyrimidine derivatives according to the present invention is one wherein $R_2$ is a saturated or ethylenically unsaturated aliphatic group having 1 to 14 carbon atoms such as, but not limited to, methyl, ethyl, n-propyl, isopropyl, vinyl or but-3-enyl. Another particular embodiment of pyrido(3,2-d)pyrimidine derivatives according to the present invention is one wherein $R_2$ is phenyl or benzyl, said phenyl or benzyl optionally having a single substituent or two identical or different substituents onto their phenyl moiety.

In another aspect, the present invention relates to certain groups of trisubstituted pyrido(3,2-d)pyrimidine derivatives which are useful in particular as intermediates for making some of the biologically active pyrido(3,2-d)pyrimidine derivatives having the structural formula (I), in particular:

a group of 2-amino-4-$R_2$-substituted-6-halo-pyrido(3,2-d) pyrimidines wherein $R_2$ is as broadly defined in the structural formula (I) or is as more specifically defined in one of the above particular embodiments, and a group of 2-amino-4-$R_2$-substituted-7-halo-pyrido(3,2-d) pyrimidines wherein $R_2$ is as broadly defined in the structural formula (I) or is as more specifically defined in one of the above particular embodiments.

In another, the present invention relates to the unexpected finding that at least one desirable biological property is present in the said group of novel pyrido(3,2-d)pyrimidine derivatives according to the present invention such as, but not limited to, the ability to prevent or combat viral infections, especially infections due to a member of the Flaviridae family, and more specifically the ability to inhibit hepatitis C virus (hereinafter referred as HCV) replication. Therefore, the invention relates to methods of treatment or prevention of viral infections, in particular infections due to a virus of the Flaviviridae family, in particular HCV, by administering to a patient in need thereof a therapeutically effective amount of at least one pyrido(3,2-d)pyrimidine derivative having structural formula (I), or as specifically disclosed herein. Alternatively, the invention also relates to the pyrido(3,2-d)pyrimidine derivative represented by the structural formula (I), or as more specifically disclosed in one of the particular embodiments herein, for use in the treatment or prevention of a viral infection due to a virus of the Flaviviridae family, in particular HCV. The invention further relates to the use of pyrido(3,2-d)pyrimidine derivative represented by the structural formula (I), or as specifically disclosed in one of the particular embodiments herein, in the manufacture of a medicament for the treatment or prevention of a viral infection due to a virus of the Flaviviridae family, in particular HCV.

The present invention also relates to individual 4,6-di- and 2,4,6-trisubstituted pyrido(3,2-d)pyrimidine derivatives specifically disclosed herein, and their use in medicine, especially for combatting viral infections due to Flaviridae such as HCV.

As a consequence of this finding, the present invention also relates to pharmaceutical compositions comprising one or more pharmaceutically acceptable carrier and, as a biologically active ingredient, at least one pyrido(3,2-d)pyrimidine derivative having the structural formula (I) and/or a pharmaceutically acceptable addition salt thereof and/or a stereoisomer thereof and/or a N-oxide thereof and/or a solvate thereof and/or a pro-drug form thereof.

As a result of their biological property, pyrido(3,2-d)pyrimidine derivatives having the structural formula (I) are highly active antiviral agents, especially anti-HCV agents which, together with one or more suitably selected pharmaceutically acceptable carriers, may be formulated into pharmaceutical compositions or preparations for the prevention or treatment of viral infections and pathologic conditions such as, but not limited to, hepatitis C.

In a further aspect, the present invention relates to combined preparations containing at least one pyrido(3,2-d)pyrimidine derivative represented by the structural formula (I) and one or more other antiviral drugs. In a further embodiment, the present invention relates to the prevention or treatment of the above-cited viral infections, and pathologic conditions associated therewith, by administering to a patient in need thereof (preferably a mammal, more preferably a human being) an effective amount of a pyrido(3,2-d)pyrimidine derivative represented by the structural formula (I), optionally in the form of a pharmaceutical composition or a combined preparation with one or more other suitable antiviral drugs.

In another aspect, the present invention relates to various processes and methods for making the novel pyrido(3,2-d) pyrimidine derivatives defined in the structural formula (I) as well as their pharmaceutically acceptable salts, N-oxides, solvates and stereoisomers, e.g. but not limited to via one or more trisubstituted pyrido(3,2-d)pyrimidine intermediates such as specified herein before.

DEFINITIONS

Figure 1:
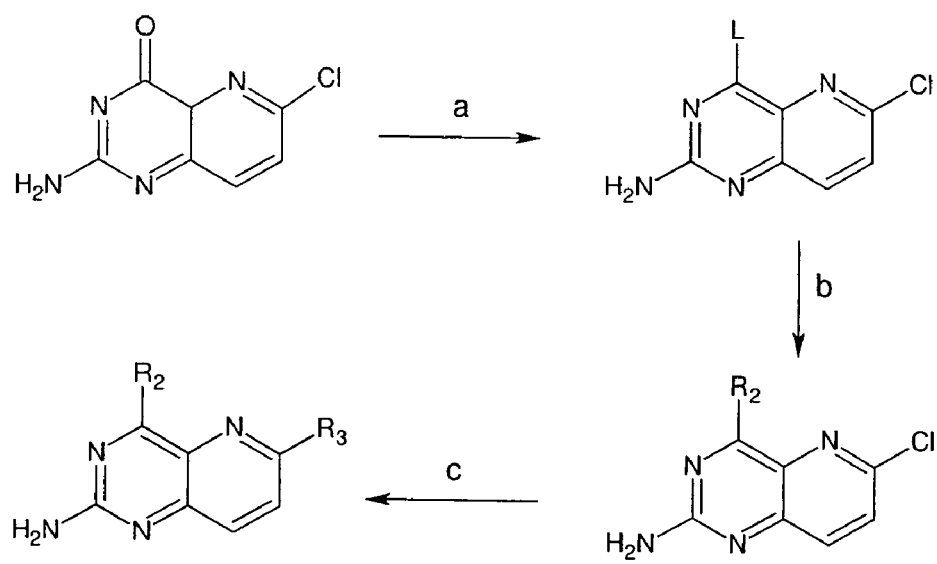
FIG. 1 schematically shows a method for making 2,4,6-trisubstituted pyrido(3,2-d)pyrimidine derivatives represented by the structural formula (I) wherein the substituent in position 2 is amino, via a 2-amino-4-$R_2$-substituted-6-chloropyrido(3,2-d)pyrimidine intermediate, according to an embodiment of the present invention.

Unless otherwise stated herein, the term "trisubstituted" means that three of the carbon atoms being in positions 2, 4 and 6 or, alternatively, in positions 2, 4 and 7 of the pyrido(3, 2-d)pyrimidine moiety (according to standard atom numbering for the pyrido(3,2-d)pyrimidine moiety) are substituted with an atom or group of atoms other than hydrogen. Unless otherwise stated herein, the term "disubstituted" means that only two carbon atoms being in positions 2, 4, 6 and 7 of the pyrido(3,2-d)pyrimidine moiety are substituted with an atom or group of atoms other than hydrogen, preferably the carbon atom in position 2 is not substituted.

As used herein with respect to a substituting radical, and unless otherwise stated, the term "$C_{1-7}$ alkyl" means straight and branched chain saturated acyclic hydrocarbon monovalent radicals having from 1 to 7 carbon atoms such as, for example, methyl, ethyl, propyl, n-butyl, 1-methylethyl(isopropyl), 2-methylpropyl (isobutyl), 1,1-dimethylethyl(terbutyl), 2-methylbutyl, n-pentyl, dimethylpropyl, n-hexyl, 2-methylpentyl, 3-methylpentyl, n-heptyl and the like. By analogy, the term "$C_{1-14}$ alkyl" refers to such radicals having from 1 to 14 carbon atoms, i.e. up to and including tetradecyl. Also by analogy, the term "$C_{1-4}$ alkyl" refers to such radicals having from 1 to 4 carbon atoms, i.e. up to and including butyl isomers.

As used herein with respect to a substituting radical, and unless otherwise stated, the term "acyl" broadly refers to a substituent derived from an acid such as an organic monocarboxylic acid, a carbonic acid, a carbamic acid (resulting into a carbamoyl substituent) or the thioacid or imidic acid (resulting into a carbamidoyl substituent) corresponding to said acids, and the term "sulfonyl" refers to a substituent derived from an organic sulfonic acid, wherein said acids comprise an aliphatic, aromatic or heterocyclic group in the molecule. A more specific kind of "acyl" group within the scope of the above definition refers to a carbonyl (oxo) group adjacent to a $C_{1-7}$ alkyl, a $C_{3-10}$ cycloalkyl, an aryl, an arylalkyl or a heterocyclic group, all of them being such as herein defined. Suitable examples of acyl and sulfonyl groups are to be found below.

Acyl and sulfonyl groups originating from aliphatic or cycloaliphatic monocarboxylic acids or aliphatic or cycloaliphatic sulfonic acids are designated herein as aliphatic or cycloaliphatic acyl and sulfonyl groups and include, but are not limited to, the following:

- alkanoyl (for example formyl, acetyl, propionyl, butyryl, isobutyryl, valeryl, isovaleryl, pivaloyl and the like);
- cycloalkanoyl (for example cyclobutanecarbonyl, cyclopentanecarbonyl, cyclo-hexanecarbonyl, 1-adamantanecarbonyl and the like);
- cycloalkyl-alkanoyl (for example cyclohexylacetyl, cyclopentylacetyl and the like);
- alkenoyl (for example acryloyl, methacryloyl, crotonoyl and the like);
- alkylthioalkanoyl (for example methylthioacetyl, ethylthioacetyl and the like);
- alkanesulfonyl (for example mesyl, ethanesulfonyl, propanesulfonyl and the like);
- alkoxycarbonyl (for example methoxycarbonyl, ethoxycarbonyl, propoxycarbonyl, isopropoxycarbonyl, butoxycarbonyl, isobutoxycarbonyl and the like);
- alkylcarbamoyl (for example methylcarbamoyl and the like);
- (N-alkyl)-thiocarbamoyl (for example (N-methyl)-thiocarbamoyl and the like);
- alkylcarbamidoyl (for example methylcarbamidoyl and the like); and
- alkoxalyl (for example methoxalyl, ethoxalyl, propoxalyl and the like);

Acyl and sulfonyl groups may also originate from aromatic monocarboxylic acids and aromatic sulfonic acids and include, but are not limited to, the following:

- aroyl (for example benzoyl, toluoyl, xyloyl, 1-naphthoyl, 2-naphthoyl and the like);
- aralkanoyl (for example phenylacetyl and the like);
- aralkenoyl (for example cinnamoyl and the like);
- aryloxyalkanoyl (for example phenoxyacetyl and the like);
- arylthioalkanoyl (for example phenylthioacetyl and the like);
- arylaminoalkanoyl (for example N-phenylglycyl, and the like);
- arylsulfonyl (for example benzenesulfonyl, toluenesulfonyl, naphthalene sulfonyl and the like);
- aryloxycarbonyl (for example phenoxycarbonyl, naphthyloxycarbonyl and the like);
- aralkoxycarbonyl (for example benzyloxycarbonyl and the like);
- arylcarbamoyl (for example phenylcarbamoyl, naphthylcarbamoyl and the like);
- arylglyoxyloyl (for example phenylglyoxyloyl and the like).
- arylthiocarbamoyl (for example phenylthiocarbamoyl and the like); and
- arylcarbamidoyl (for example phenylcarbamidoyl and the like).

Acyl groups may also originate from an heterocyclic monocarboxylic acids and include, but are not limited to, the following:

- heterocyclic-carbonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiophenoyl, furoyl, pyrrolecarbonyl, nicotinoyl and the like); and
- heterocyclic-alkanoyl in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiopheneneacetyl, furylacetyl, imida-zolylpropionyl, tetrazolylacetyl, 2-(2-amino-4-thiazolyl)-2-methoxyiminoacetyl and the like).

Sulfonyl groups may also originate from an heterocyclic mono sulfonic acids and include, but are not limited to, the following:

- heterocyclic-sulfonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring; and
- heterocyclyl-alkylsulfonyl in which said heterocyclic group is as defined herein, preferably an aromatic or non-aromatic 5- to 7-membered heterocyclic ring with one or more heteroatoms selected from the group consisting of nitrogen, oxygen and sulfur in said ring.

As used herein with respect to a substituting radical, and unless otherwise stated, the term "$C_{1-7}$ alkylene" means the divalent hydrocarbon radical corresponding to the above defined $C_{1-7}$ alkyl, such as methylene, bis(methylene), tris(methylene), tetramethylene, hexamethylene and the like.

As used herein with respect to a substituting radical, and unless otherwise stated, the term "$C_{3-10}$ cycloalkyl" means a mono- or polycyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituting radical, and unless otherwise stated, the term "$C_{3-10}$ cycloalkyl-alkyl" refers to an aliphatic saturated hydrocarbon monovalent radical (preferably a $C_{1-7}$ alkyl such as defined above) to which a $C_{3-10}$ cycloalkyl (such as defined above) is already linked such as, but not limited to, cyclohexylmethyl, cyclopentylmethyl and the like.

As used herein with respect to a substituting radical, and unless otherwise stated, the term "$C_{3-10}$ cycloalkylene" means the divalent hydrocarbon radical corresponding to the above defined $C_{3-10}$ cycloalkyl.

As used herein with respect to a substituting radical, and unless otherwise stated, the term "aryl" designate any mono- or polycyclic aromatic monovalent hydrocarbon radical having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl radicals (the latter being as defined above) such as, for instance, indanyl, tetrahydronaphthyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein, e.g. with respect to a substituting radical such as the combination of substituents in certain positions of the pyrido(3,2-d)pyrimidine ring together with the carbon atoms in the same positions of said ring, and unless otherwise stated, the term "homocyclic" means a mono- or polycyclic, saturated or mono-unsaturated or polyunsaturated hydrocarbon radical having from 4 up to 15 carbon atoms but including no heteroatom in the said ring; for instance said combination of substituents may form a $C_{2-6}$ alkylene radical, such as tetramethylene, which cyclizes with carbon atoms in certain positions of the pyrido(3,2-d)pyrimidine ring.

As used herein with respect to a substituting radical (including the combination of substituents in certain positions of the pyrido(3,2-d)pyrimidine ring together with the carbon atoms in the same positions of said ring), and unless otherwise stated, the terms "heterocyclic" and "heterocyclyl" refer to a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphto-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxathiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiocinyl, benzodioxocinyl, benzotrioxepinyl, benzoxathiazepinyl, benzoxadiazepinyl, benzothiadiazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypoxanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzocarbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphtindazolyl, naphtindolyl, naphtothiazolyl, naphtothioxolyl, naphtoxindolyl, naphto-triazolyl, naphtopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydro-pyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl (e.g. phtalazinyl), phtalidyl, phtalimidinyl, phtalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may furthermore be independently substituted with a substituent selected from the group consisting of halogen, nitro, $C_{1-7}$ alkyl (optionally containing one or more functions or radicals selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkylamino, hydroxylalkylamino, mercaptoalkylamino, heterocyclic-substituted alkylamino, heterocyclic amino, heterocyclic-substituted arylamino, hydrazino, alkylhydrazino, phenylhydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkylhydrazino, phenylhydrazino, sulfhydryl, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, thiocarboxylic acid or esters or thioesters or amides thereof; depending upon the number of unsaturations in the 3 to 10 atoms ring, heterocyclic radicals may be sub-divided into heteroaromatic (or "heteroaryl") radicals and non-aromatic heterocyclic radicals; when a heteroatom of said non-aromatic heterocyclic radical is nitrogen, the latter may be substituted with a substituent selected from the group consisting of $C_{1-7}$ alkyl, $C_{3-10}$ cycloalkyl, aryl, arylalkyl and alkylaryl.

As used herein with respect to a substituting radical, and unless otherwise stated, the terms "$C_{1-7}$ alkoxy", "$C_{3-10}$ cycloalkoxy", "aryloxy", "arylalkyloxy oxyheterocyclic", "thio $C_{1-7}$ alkyl", "thio $C_{3-10}$ cycloalkyl", "arylthio", "arylalkylthio and "thioheterocyclic" refer to substituents wherein a carbon atom of a $C_{1-7}$ alkyl, respectively a $C_{3-10}$ cycloalkyl, aryl, arylalkyl or heterocyclic radical (each of them such as defined herein), is attached to an oxygen atom or a divalent sulfur atom through a single bond such as, but not limited to, methoxy, ethoxy, propoxy, butoxy, pentoxy, isopropoxy, sec-butoxy, tert-butoxy, isopentoxy, cyclopropyloxy, cyclobutyloxy, cyclopentyloxy, thiomethyl, thioethyl, thiopropyl, thiobutyl, thiopentyl, thiocyclopropyl, thiocyclobutyl, thiocyclopentyl, thiophenyl, phenyloxy, benzyloxy, mercaptobenzyl, cresoxy, and the like.

As used herein with respect to a substituting atom, and unless otherwise stated, the term halogen means any atom selected from the group consisting of fluorine, chlorine, bromine and iodine.

As used herein with respect to a substituting radical, and unless otherwise stated, the term "halo $C_{1-7}$ alkyl" means a $C_{1-7}$ alkyl radical (such as above defined) in which one or more hydrogen atoms are independently replaced by one or more halogens (preferably fluorine, chlorine or bromine), such as but not limited to difluoromethyl, trifluoromethyl, trifluoroethyl, octafluoropentyl, dodecafluoroheptyl, dichloromethyl and the like.

As used herein with respect to a substituting radical, and unless otherwise stated, the terms "$C_{2-7}$ alkenyl" designate a straight and branched acyclic hydrocarbon monovalent radical having one or more ethylenic unsaturations and having from 2 to 7 carbon atoms such as, for example, vinyl, 1-propenyl, 2-propenyl (allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl and the like, including all possible isomers thereof.

As used herein with respect to a substituting radical, and unless otherwise stated, the term "$C_{3-10}$ cycloalkenyl" means a monocyclic mono- or polyunsaturated hydrocarbon monovalent radical having from 3 to 8 carbon atoms, such as for instance cyclopropenyl, cyclobutenyl, cyclopentenyl, cyclopentadienyl, cyclohexenyl, cyclohexadienyl, cycloheptenyl, cyclohepta-dienyl, cycloheptatrienyl, cyclooctenyl, cyclooctadienyl and the like, or a $C_{7-10}$ polycyclic mono- or polyunsaturated hydrocarbon mono-valent radical having from 7 to 10 carbon atoms such as dicyclopentadienyl, fenchenyl (including all isomers thereof, such as α-pinolenyl), bicyclo[2.2.1]hept-2-enyl, bicyclo[2.2.1]hepta-2,5-dienyl, cyclo-fenchenyl and the like.

As used herein with respect to a substituting radical, and unless otherwise stated, the term "$C_{2-7}$ alkynyl" defines straight and branched chain hydrocarbon radicals containing one or more triple bonds and optionally at least one double bond and having from 2 to 7 carbon atoms such as, for example, acetylenyl, 1-propynyl, 2-propynyl, 1-butynyl, 2-butynyl, 2-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like.

As used herein with respect to a substituting radical, and unless otherwise stated, the terms "arylalkyl", "arylalkenyl" and "heterocyclic-substituted alkyl" refer to an aliphatic saturated or ethylenically unsaturated hydrocarbon monovalent radical (preferably a $C_{1-7}$ alkyl or $C_{2-7}$ alkenyl radical such as defined above) onto which an aryl or heterocyclic radical (such as defined above) is already bonded via a carbon atom, and wherein the said aliphatic radical and/or the said aryl or heterocyclic radical may be optionally substituted with one or more substituents independently selected from the group consisting of halogen, amino, hydroxyl, sulfhydryl, $C_{1-7}$ alkyl, $C_{1-7}$ alkoxy, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthylmethyl, phenylethyl, 1-amino-2-phenylethyl, 1-amino-2-[4-hydroxy-phenyl]-ethyl, 1-amino-2-[indol-2-yl]ethyl, styryl, pyridylmethyl (including all isomers thereof), pyridylethyl, 2-(2-pyridyl)isopropyl, oxazolylbutyl, 2-thienylmethyl, pyrrolylethyl, morpholinylethyl, imidazol-1-yl-ethyl, benzodioxolylmethyl and 2-furylmethyl.

As used herein with respect to a substituting radical, and unless otherwise stated, the terms "alkylaryl" and "alkyl-substituted heterocyclic" refer to an aryl or, respectively, heterocyclic radical (such as defined above) onto which are bonded one or more aliphatic saturated or unsaturated hydrocarbon monovalent radicals, preferably one or more $C_{1-7}$ alkyl, $C_{2-7}$ alkenyl or $C_{3-10}$ cycloalkyl radicals as defined above such as, but not limited to, o-toluoyl, m-toluoyl, p-toluoyl, 2,3-xylyl, 2,4-xylyl, 3,4-xylyl, o-cumenyl, m-cumenyl, p-cumenyl, o-cymenyl, m-cymenyl, p-cymenyl, mesityl, ter-butylphenyl, lutidinyl (i.e. dimethylpyridyl), 2-methylaziridinyl, methylbenzimidazolyl, methylbenzofuranyl, methylbenzothiazolyl, methylbenzotriazolyl, methyl-benzoxazolyl and methylbenzselenazolyl.

As used herein with respect to a substituting radical, and unless otherwise stated, the term "alkoxyaryl" refers to an aryl radical (such as defined above) onto which is (are) bonded one or more $C_{1-7}$ alkoxy radicals as defined above, preferably one or more methoxy radicals, such as, but not limited to, 2-methoxyphenyl, 3-methoxyphenyl, 4-methoxyphenyl, 3,4-dimethoxyphenyl, 2,4,6-trimethoxyphenyl, methoxynaphtyl and the like.

As used herein with respect to a substituting radical, and unless otherwise stated, the terms "alkylamino", "cycloalkylamino", "alkenylamino", "cycloalkenylamino", "arylamino", "arylalkylamino", "heterocyclic-substituted alkylamino", "heterocyclic-substituted arylamino", "heterocyclic amino", "hydroxyalkylamino", "mercaptoalkylamino" and "alkynylamino" mean that respectively one (thus monosubstituted amino) or even two (thus disubstituted amino) $C_{1-7}$ alkyl, $C_{3-10}$ cycloalkyl, $C_{2-7}$ alkenyl, $C_{3-10}$ cycloalkenyl, aryl, arylalkyl, heterocyclic-substituted alkyl, heterocyclic-substituted aryl, heterocyclic (provided in this case the nitrogen atom is attached to a carbon atom of the heterocyclic ring), mono- or polyhydroxy $C_{1-7}$ alkyl, mono- or polymercapto $C_{1-7}$ alkyl, or $C_{2-7}$ alkynyl radical(s) (each of them as defined herein, respectively, and including the presence of optional substituents independently selected from the group consisting of halogen, amino, hydroxyl, sulfhydryl, $C_{1-7}$ alkyl, $C_{1-7}$ alkoxy, trifluoromethyl and nitro) is/are attached to a nitrogen atom through a single bond such as, but not limited to, anilino, 2-bromoanilino, 4-bromoanilino, 2-chloroanilino, 3-chloroanilino, 4-chloroanilino, 3-chloro-4-methoxyanilino, 5-chloro-2-methoxyanilino, 2,3-dimethylanilino, 2,4-dimethylanilino, 2,5-dimethylanilino, 2,6-dimethylanilino, 3,4-dimethylanilino, 2-fluoroanilino, 3-fluoroanilino, 4-fluoroanilino, 3-fluoro-2-methoxyanilino, 3-fluoro-4-methoxyanilino, 2-fluoro-4-methylanilino, 2-fluoro-5-methylanilino, 3-fluoro-2-methyl-anilino, 3-fluoro-4-methylanilino, 4-fluoro-2-methylanilino, 5-fluoro-2-methylanilino, 2-iodoanilino, 3-iodoanilino, 4-iodoanilino, 2-methoxy-5-methylanilino, 4-methoxy-2-methylanilino, 5-methoxy-2-methylanilino, 2-ethoxyanilino, 3-ethoxyanilino, 4-ethoxyanilino, benzylamino, 2-methoxybenzylamino, 3-methoxybenzyl-amino, 4-methoxybenzylamino, 2-fluorobenzylamino, 3-fluorobenzylamino, 4-fluorobenzylamino, 2-chlorobenzylamino, 3-chlorobenzylamino, 4-chlorobenzylamino, 2-amino-benzylamino, diphenylmethylamino, α-naphthylamino, methylamino, dimethylamino, ethylamino, diethylamino, isopropylamino, propenylamino, n-butylamino, ter-butylamino, dibutylamino, 1,2-diaminopropyl, 1,3-diaminopropyl, 1,4-diaminobutyl, 1,5-diaminopentyl, 1,6-diaminohexyl, morpholinomethylamino, 4-morpholinoanilino, hydroxymethylamino, β-hydroxyethylamino and ethynylamino; this definition also includes mixed disubstituted amino radicals wherein the nitrogen atom is attached to two such radicals belonging to two different sub-sets of radicals, e.g. an alkyl radical and an alkenyl radical, or to two different radicals within the same sub-set of radicals, e.g. methylethylamino; among di-substituted amino radicals, symmetrically-substituted amino radicals are more easily accessible and thus usually preferred from a standpoint of ease of preparation.

As used herein with respect to a substituting radical, and unless otherwise stated, the terms "(thio)carboxylic acid ester", "(thio)carboxylic acid thioester" and "(thio)carboxylic acid amide" refer to radicals wherein the carboxyl or thiocarboxyl group is bonded to the hydrocarbonyl residue of an alcohol, a thiol, a polyol, a phenol, a thiophenol, a primary or secondary amine, a polyamine, an amino-alcohol or ammonia, the said hydrocarbonyl residue being selected from the group consisting of alkyl, alkenyl, alkynyl, cycloalkyl, cycloalkenyl, aryl, arylalkyl, alkylaryl, alkylamino, cycloalkylamino, alkenylamino, cycloalkenylamino, arylamino, arylalkylamino, heterocyclic-substituted alkylamino, heterocyclic amino, heterocyclic-substituted arylamino, hydroxyalkylamino, mercapto-alkylamino or alkynylamino (such as above defined, respectively).

As used herein with respect to a substituting radical, and unless otherwise stated, the term "sulfonamido" refers to a radical represented by the formula —$NR_x$—$SO_2R_y$, wherein $R_x$ hydrogen or a cyclic or non-cyclic hydrocarbyl group and $R_y$ is a cyclic or non-cyclic hydrocarbyl group.

As used herein with respect to a substituting radical, and unless otherwise stated, the term "sulfamoyl" refers to a radical represented by the formula —$SO_2NH_2$.

As used herein with respect to a substituting radical, and unless otherwise stated, the term "amino-acid" refers to a radical derived from a molecule having the chemical formula $H_2N$—CHR—COOH, wherein R is the side group of atoms characterising the amino-acid type; said molecule may be one of the 20 naturally-occurring amino-acids or any similar non naturally-occurring amino-acid.

As used herein and unless otherwise stated, the term "stereoisomer" refers to all possible different isomeric as well as conformational forms which the compounds of formula (I) may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a pyrido(3,2-d)pyrimidine derivative of this invention with a suitable inorganic solvent (e.g. hydrates) or organic solvent, such as but not limited to alcohols, ketones, esters, ethers, nitriles and the like.

DETAILED DESCRIPTION OF THE INVENTION

In the first embodiment of the invention, the novel pyrido (3,2-d)pyrimidine derivatives are as defined in the general formula (I), wherein each of the substituents $R_1$, $R_2$, $R_3$, $R_4$, $R_6$, $R_7$, $R_8$, $R_8'$, $R_9$, $R_9'$, $R_{10}$, $R_{11}$, $R_{12}$, $R_{13}$ and $R_{14}$ may independently correspond to any of the definitions given above, in particular with any of the individual meanings (such as illustrated above) of generic terms used for substituting radicals such as, but not limited to, "$C_{1-7}$ alkyl", "$C_{3-10}$ cycloalkyl", "$C_{2-7}$ alkenyl", "$C_{2-7}$ alkynyl", "aryl", "homocyclic", "heterocyclic", "halogen", "$C_{3-10}$ cycloalkenyl", "alkylaryl", "arylalkyl", "alkylamino", "cycloalkyl-amino", "alkenylamino", "alkynylamino", "arylamino", "arylalkylamino", "heterocyclic-substituted alkylamino", "heterocyclic amino", "heterocyclic-substituted arylamino", "hydroxyalkylamino", "mercaptoalkylamino", "alkynylamino", "$C_{1-7}$ alkoxy", "$C_{3-10}$ cycloalkoxy", "thio $C_{1-7}$ alkyl", "thio $C_{3-10}$ cycloalkyl", "halo $C_{1-7}$ alkyl", "amino-acid" and the like.

In the second embodiment of the invention, the novel pyrido(3,2-d)pyrimidine intermediates are as specified herein before, wherein the substituent $R_2$ may correspond to any of the definitions given with respect to the structural formula (I), in particular with any of the individual meanings (such as illustrated above) of generic terms used for substituents such as, but not limited to, "$C_{1-7}$ alkyl", "$C_{3-10}$ cycloalkyl", "$C_{2-7}$ alkenyl", "$C_{2-7}$ alkynyl", "aryl", "heterocyclic", "arylalkyl", "heterocyclic-substituted $C_{1-7}$ alkyl" and the like.

Within the class of compounds represented by the structural formula (I), useful species of pyrido(3,2-d)pyrimidine derivatives are those wherein the substituent $R_1$ is a group of the general formula $R_6$—$NR_7R_{12}$, wherein $R_6$ is a bond or $C_{1-7}$ alkylene (in particular $C_{1-3}$ alkylene), wherein $R_7$ and $R_{12}$ are independently selected from the group consisting of hydrogen, $C_{1-7}$ alkyl, $C_{2-7}$ alkenyl, $C_{2-7}$ alkynyl, aryl, arylalkyl, $C_{3-10}$ cycloalkyl and heteroaryl, or wherein $R_7$ and $R_{12}$ together with the nitrogen atom to which they are attached form a heterocycle. Within this sub-class of derivatives, it is preferred when $R_6$ is a single bond or methylene, and/or $R_7$ is methyl, ethyl, propyl or cyclopropylmethyl, and/or $R_7$ and $R_{12}$ together with the nitrogen atom to which they are attached form a morpholinyl, 2,6-dimethylmorpholinyl, pyrrolidinyl, azepanyl, 3,3,5-trimethylazepanyl, piperidinyl, 2-methylpiperidinyl or 2-ethylpiperidinyl group. Methods for introducing such substituents in position 2 of the pyrido(3,2-d)pyrimidine ring are extensively described in WO 03/062209.

The present invention further provides various processes and methods for making the novel pyrido(3,2-d)pyrimidine derivatives represented by the structural formula (I). As a general rule, the preparation of these compounds is based on the principle that, starting from a suitable pyrido(3,2-d)pyrimidine precursor (usually a 2,3,6-trisubstituted pyridine or a known trisubstituted pyrido(3,2-d)pyrimidine), each of the substituents $R_2$, $R_3$, $R_4$ and $R_1$ may be introduced separately without adversely influencing the presence of one or more substituents already introduced at other positions on the pyrido(3,2-d)pyrimidine moiety or the capacity to introduce further substituents later on.

Methods of manufacture have been developed by the present inventors which may be used alternatively to, or may be combined with, the methods of synthesis already known in the art of pyrido(3,2-d)pyrimidine derivatives (depending upon the targeted final compound). For instance, the synthesis of mono- and di-N-oxides of the pyrido(3,2-d)pyrimidine derivatives of this invention can easily be achieved by treating the said derivatives with an oxidizing agent such as, but not limited to, hydrogen peroxide (e.g. in the presence of acetic acid) or a peracid such as chloroperbenzoic acid. The methods for making the pyrido(3,2-d)pyrimidine derivatives of the present invention will now be explained in more details by reference to the appended FIGS. 1 to 8 wherein, unless otherwise stated hereinafter, each of the substituting groups or atoms $R_2$, $R_3$, $R_4$ and $R_1$ is as defined in formula (I) of the summary of the invention and, more specifically, may correspond to any of the individual meanings disclosed in particular embodiments above.

In the description of the reaction steps involved in each figure, reference is made to the use of certain catalysts and/or certain types of solvents. It should be understood that each catalyst mentioned should be used in a catalytic amount well known to the skilled person with respect to the type of reaction involved. Solvents that may be used in the following reaction steps include various kinds of organic solvents such as protic solvents, polar aprotic solvents and non-polar solvents as well as aqueous solvents which are inert under the relevant reaction conditions. More specific examples include aromatic hydrocarbons, chlorinated hydrocarbons, ethers, aliphatic hydrocarbons, alcohols, esters, ketones, amides, water or mixtures thereof, as well as supercritical solvents such as carbon dioxide (while performing the reaction under supercritical conditions). The suitable reaction temperature and pressure conditions applicable to each kind of reaction step will not be detailed herein but do not depart from the relevant conditions already known to the skilled person with respect to the type of reaction involved and the type of solvent used (in particular its boiling point).

FIG. 1 schematically shows a method for making 2-amino-4-$R_2$-substituted-6-$R_3$-substituted-pyrido(3,2-d)pyrimidine derivatives, via a 2-amino-4-$R_2$-substituted-6-chloro-pyrido(3,2-d)pyrimidine intermediate, starting from 2-amino-4-hydroxy-6-chloro-pyrido(3,2-d)pyrimidine. Activation of the tautomeric hydroxyl group at position 4 of the pyrido[3,2-d]pyrimidine scaffold for the subsequent nucleophilic displacement reaction occurs in step (a) by preparing the corresponding 4-(1,2,4-triazolyl)-pyrido[3,2-d]pyrimidine derivative or 4-chloro-pyrido[3,2-d]pyrimidine derivative. The 4-triazolyl derivative can be obtained by treating the 4-oxo-pyrido[3,2-d]pyrimidine derivative with $POCl_3$ or 4-chlorophenyl phosphorodichloridate and 1,2,4-triazole in an appropriate solvent such as, but not limited to, pyridine or acetonitrile. The 4-chloro derivative can be obtained by treating the 4-oxo-pyrido[3,2-d]pyrimidine derivative with thionyl chloride or $POCl_3$. The chlorine atom or 1,2,4-triazolyl group is designated as L in FIG. 1. Displacement of the 1,2,4-triazolyl group or chlorine atom occurs in step (b) by reaction with an appropriate Grignard reagent in a dry, polar, aprotic solvent such as for example 1,4-dioxane, diethyl ether or tetrahydrofuran.

A broad range of suitable Grignard reagents for use in the methods described herein and illustrated by the figures, is commercially available comprising, but not limited to, benzylmagnesium chloride, methylmagnesium bromide, methylmagnesium chloride, methylmagnesium iodide, ethylmagnesium bromide, ethylmagnesium chloride, propylmagnesium chloride, isopropylmagnesium bromide, isopropylmagnesium chloride, n-butylmagnesium chloride, sec-butyl-magnesium chloride, tert-butylmagnesium chloride, pentylmagnesium bromide, 3-hexylmagnesium bromide, n-hexylmagnesium bromide, 3-heptylmagnesium bromide, n-heptylmagnesium bromide, n-octylmagnesium bromide, n-decylmagnesium bromide, n-tetradecylmagnesium chloride, allylmagnesium bromide, allylmagnesium chloride, ethynylmagnesium chloride, (trimethylsilyl)methylmagnesium chloride, phenylmagnesium bromide, 4-methoxyphenylmagnesium bromide, 4-chlorophenylmagnesium bromide, 4-fluorophenylmagnesium bromide, 1-naphthylmagnesium bromide, phenylmagnesium chloride, vinylmagnesium bromide, vinylmagnesium chloride, cyclohexylmagnesium chloride, cyclopentylmagnesium chloride, cyclopropylmagnesium chloride, 4-but-3-enylmagnesium bromide, benzylmagnesium bromide, benzylmagnesium chloride, o-tolylmagnesium bromide, m-tolylmagnesium bromide, p-tolylmagnesium bromide, o-tolylmagnesium chloride, m-tolylmagnesium chloride, 2-pyridylmagnesium bromide, 1,3-dioxan-2-ylmethylmagnesium bromide, 3,4-dichlorophenylmagnesium bromide, 3,5-dichlorophenylmagnesium bromide, 3,4-difluorophenylmagnesium bromide, 3,5-difluorophenylmagnesium bromide, 3-chloro-4-fluorophenylmagnesium bromide, 3-chloro-5-fluorophenylmagnesium bromide, 4-chloro-3-fluorophenylmagnesium bromide, 3,5-dimethylphenylmagnesium bromide, 3,4-dimethylphenylmagnesium bromide, 2,3-dimethylphenylmagnesium bromide, 2,4-dimethylphenylmagnesium bromide, 2,5-dimethylphenylmagnesium bromide, 2,6-dimethylphenylmagnesium bromide, 2,4-dimethylphenylmagnesium bromide, 2,5-dimethoxyphenylmagnesium bromide, 3,4-dimethoxyphenylmagnesium bromide, 3,5-dimethoxyphenylmagnesium bromide, 3,4,5-dimethoxyphenylmagnesium bromide, 2,4,5-trimethoxyphenylmagnesium bromide, trimethylphenylmagnesium bromide, 4-ethylphenylmagnesium bromide, 4-ethoxyphenylmagnesium bromide, 2,4,6-trimethylphenylmagnesium bromide, 4-methylbenzylmagnesium chloride, 3-methylbenzylmagnesium chloride, 2-methylbenzylmagnesium chloride, 4-methoxybenzylmagnesium chloride, 3-methoxybenzylmagnesium chloride, 2-methoxybenzylmagnesium chloride, 4-chlorobenzylmagnesium chloride, 3-chlorobenzylmagnesium chloride, 2-chlorobenzylmagnesium chloride, 4-fluorobenzylmagnesium chloride, 3-fluorobenzylmagnesium chloride, 2-fluorobenzylmagnesium chloride, 4-bromobenzylmagnesium bromide, 3-bromobenzylmagnesium bromide, 2-bromobenzylmagnesium bromide, 2-biphenylmagnesium bromide, 4-biphenylmagnesium bromide, 3-fluoro-4-biphenylmagnesium bromide, 2-naphthylmagnesium bromide, 3-thienylmagnesium iodide and the like. Alternatively, the above-listed Grignard reagents as well as those which are not commercially available are obtainable using methods well known to the skilled person, or can advantageously be made in situ if desired. The reaction with the appropriate Grignard reagent may optionally be performed in the presence of a catalytic amount of a suitable catalyst, e.g. a transition metal complex such as, but not limited to, iron acetylacetonate. Alternatively (but not shown in FIG. 1), a 2-(protected amino)-4,6-dichloro-pyrido[3,2-d]pyrimidine can also serve as an excellent starting material for a wide variety of organometallic cross-coupling reactions, which are well known in the art (see e.g. F. Diederich et al., *Metal-Catalyzed Cross-Coupling reactions*, Wiley-VCH, New York, 1998). Examples of suitable cross-coupling reactions include, but are not limited to, a Negishi reaction (i.e. a nickel or palladium catalyzed coupling of organozinc compounds with an aryl- or heteroarylhalide), Stille coupling (i.e. a palladium catalysed coupling reaction between an aryl- or heteroaryl halide and a stannane), Suzuki coupling (i.e. a palladium catalysed cross coupling reaction between an organoboronic acid and an aryl- or heteroarylhalide), Kumada coupling (which is a palladium or nickel catalyzed coupling of a Grignard reagent with an aryl- or heteroarylhalide), Heck reaction (which is the palladium-catalyzed C—C coupling between an aryl- or heteroaryl halide and an activated alkene in the presence of a base), Sonogashira reaction (i.e. the coupling of a terminal alkyne with an aryl- or heteroarylhalide with a palladium catalyst, a copper (I) co-catalyst, and an amine base). In each of the above types of reaction, the 4-chloro-pyrido[3,2-d]pyrimidine moiety will serve as the heteroaryl halide. In step (c), the 2-amino-4-$R_2$-substituted-6-chloro-pyrido(3,2-d)pyrimidine intermediate is reacted with a suitable aryl- or heteroaryl-boronic acid, optionally in the presence of a catalytic amount of a suitable catalyst, e.g. a transition metal complex such as, but not limited to, a complex between palladium and a triphosphine.

Figure 2:
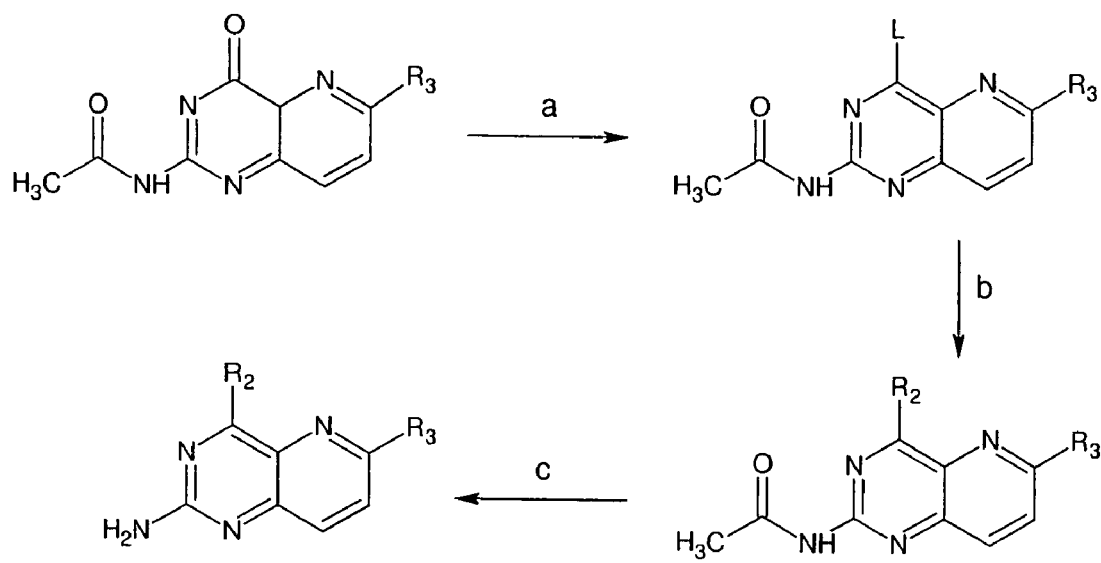
FIG. 2 schematically shows a method for making 2,4,6-trisubstituted pyrido(3,2-d)pyrimidine derivatives represented by the structural formula (I) wherein the substituent in position 2 is amino, wherein said substituent is protected during the whole synthesis, and wherein introduction of the substituent at position 4 is performed after introduction of the substituent at position 6, according to an embodiment of the present invention.

FIG. 2 schematically shows a method for making a 2-amino-4-$R_2$-substituted-6-$R_3$-substituted-pyrido(3,2-d)pyrimidine derivatives, starting from a known 2-acetamido-4-hydroxy-6-$R_3$-substituted-pyrido(3,2-d)pyrimidine. Activation of the 4-hydroxy group in step (a), followed by displacement of the L group (e.g. L is chloro or 1,2,4-triazolyl) on position 4, occur in the same way as described previously with respect to FIG. 1.

Figure 3:
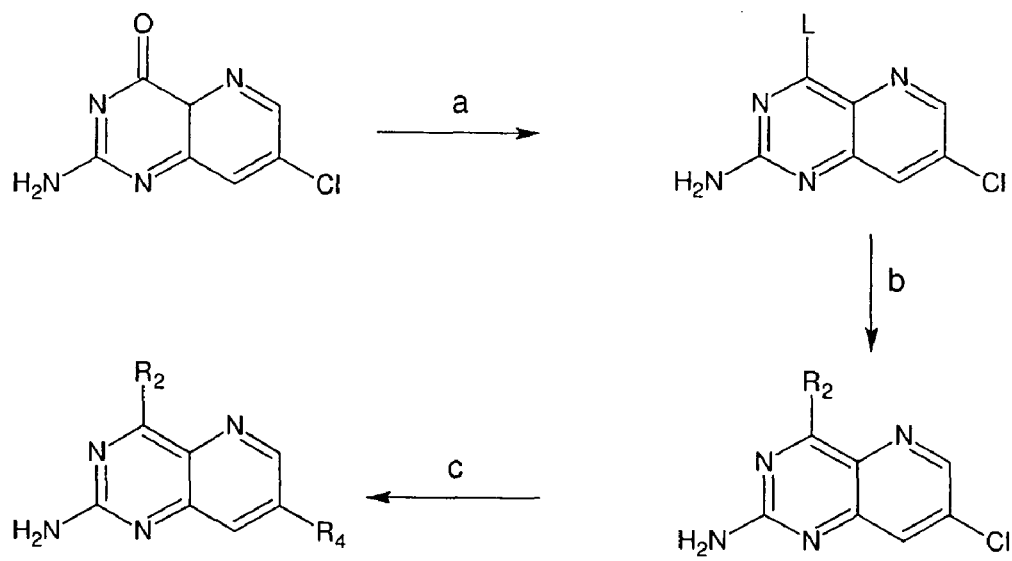
FIG. 3 schematically shows a method for making 2,4,7-trisubstituted pyrido(3,2-d)pyrimidine derivatives represented by the structural formula (I) wherein the substituent in position 2 is amino, via a 2-amino-4-$R_2$-substituted-7-chloropyrido(3,2-d)pyrimidine intermediate, according to an embodiment of the present invention.

FIG. 3 schematically shows a method for making 2-amino-4-$R_2$-substituted-7-$R_4$-substituted-pyrido(3,2-d)pyrimidine derivatives, via a 2-amino-4-$R_2$-substituted-7-chloro-pyrido(3,2-d)pyrimidine intermediate, starting from 2-amino-4-hydroxy-7-chloro-pyrido(3,2-d)pyrimidine. All steps (a) to (c) proceed exactly in the same way as described previously with respect to FIG. 1.

Figure 4:
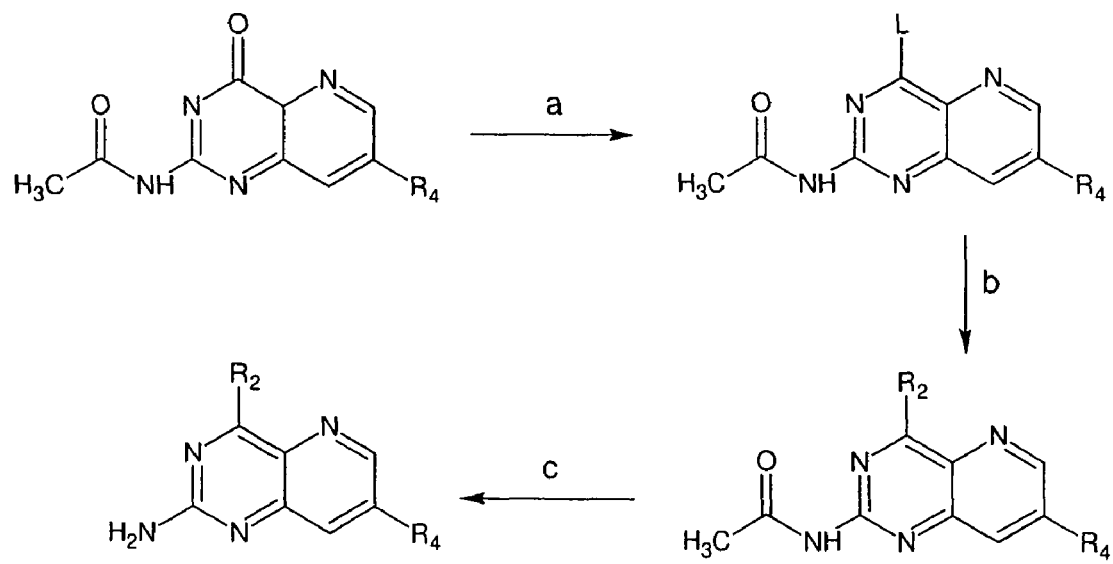
FIG. 4 schematically shows a method for making 2,4,7-trisubstituted pyrido(3,2-d)pyrimidine derivatives represented by the structural formula (I) wherein the substituent in position 2 is amino, wherein said substituent is protected during the whole synthesis, and wherein introduction of the substituent at position 4 is performed prior to introduction of the substituent at position 7, according to an embodiment of the present invention.

FIG. 4 schematically shows a method for making a 2-amino-4-$R_2$-substituted-7-$R_4$-substituted-pyrido(3,2-d)pyrimidine derivatives, starting from a known 2-acetamido-4-hydroxy-7-$R_4$-substituted-pyrido(3,2-d)pyrimidine. Activation of the 4-hydroxy group in step (a), followed by displacement of the L group (e.g. L is chloro or 1,2,4-triazolyl) on position 4, occurs in the same way as described previously with respect to FIG. 1.

Figure 5:
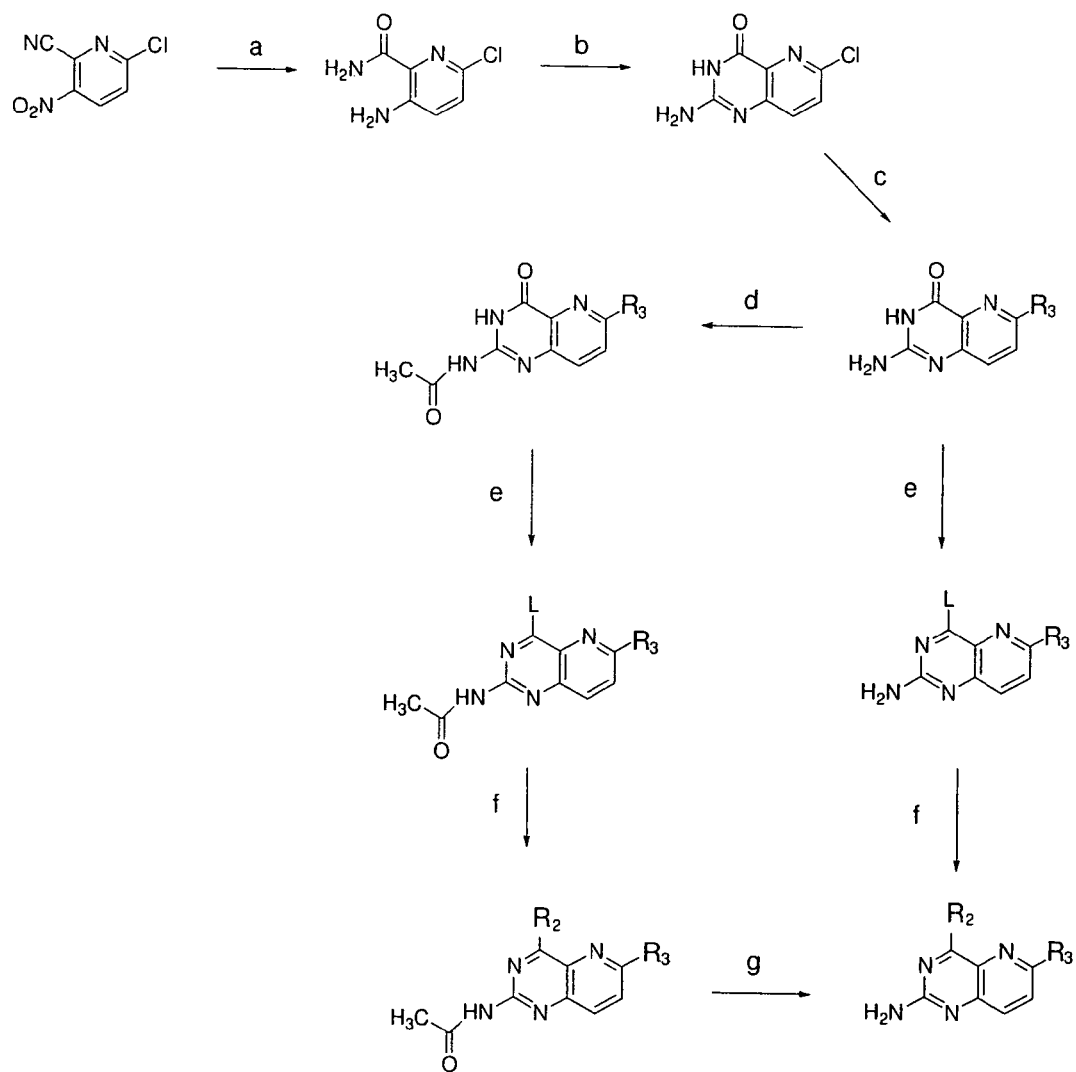
FIG. 5 schematically shows a method for making 2-amino-4,6-substituted pyrido(3,2-d)pyrimidine derivatives represented by the structural formula (I) through a series of intermediates wherein the amino substituent in position 2 may be protected and/or wherein the substituent in position 4 may be hydroxy, chloro or triazolyl, and wherein introduction of the substituent at position 6 is performed prior to introduction of the substituent at position 4, according to an embodiment of the present invention.

FIG. 5 schematically shows a method for making 2-amino-4-$R_2$-substituted-6-$R_3$-substituted-pyrido(3,2-d)pyrimidine derivatives through a series of intermediates wherein the amino substituent in position 2 is optionally protected during synthesis. In step (a), the nitro group of 6-chloro-2-cyano-3-nitropyridine is reduced either catalytically (e.g. by using Raney-Nickel under an atmosphere of hydrogen) or chemically (e.g. by using iron or tin under acidic conditions) with concomitant hydrolysis of the cyano group leading to the formation of a carboxamide. In step (b), the pyrido[3,2-d]pyrimidine moiety is generated by treatment of 6-chloro-2-carboxamido-3-aminopyridine with chloroformamidine. The chlorine atom at position 6 is then used in step (c) for a wide variety of palladium-catalyzed cross-coupling reactions, such as, but not limited to, a Suzuki reaction (i.e. a reaction with an arylboronic acid, heteroaryl boronic acid or esters thereof leading to the formation of 2-amino-4-hydroxy-6-(hetero)aryl-pyrido[3,2-d]pyrimidine), a Heck reaction (i.e. a reaction with a terminal alkene affording the corresponding 2-amino-4-hydroxy-6-alkenyl-pyrido[3,2-d]pyrimidine derivative), or a Sonogashira reaction (i.e. a reaction with a terminal alkyne affording the corresponding 2-amino-4-hydroxy-6-alkynyl-pyrido[3,2-d]pyrimidine derivative). In step (d), the 2-amino group is protected from further reactions with for example (but not limited to) an acetyl group (as shown in the figure, e.g. by reaction with acetic anhydride in pyridine) or a pivaloyl group (e.g. by reaction with pivaloyl anhydride in pyridine, not shown in the figure). Activation of the tautomeric hydroxyl group at position 4 of the pyrido[3,2-d]pyrimidine scaffold then occurs in step (e) by introducing a readily leaving group (indicated by the letter L in FIG. 5) at position 4 of the pyrido[3,2-d]pyrimidine scaffold. Suitable leaving groups include, but are not limited to, chlorine and 1,2,4-triazolyl. The 2-(protected amino)-4-(1,2,4-triazolyl)-6-$R_3$-substituted-pyrido[3,2-d]pyrimidine derivative can be obtained for instance by treating the 2-(protected amino)-4-hydroxy-6-$R_3$-substituted pyrido[3,2-d]pyrimidine derivative with $POCl_3$ or 4-chlorophenyl phosphorodichloridate and 1,2,4-triazole in an appropriate solvent such as, but not limited to, pyridine, acetonitrile or dichloromethane. The 2-(protected amino)-4-chloro-6-$R_3$-substituted-pyrido[3,2-d]pyrimidine derivative can be obtained by treating the 2-(protected amino)-4-hydroxy-6-$R_3$-substituted pyrido[3,2-d]pyrimidine derivative with thionyl chloride or $POCl_3$. In order to introduce a carbon linker at position 4 of the pyrido[3,2-d]pyrimidine scaffold, a nucleophilic displacement reaction is effected in step (f) by mixing the 2-(protected amino)-4-chloro-6-$R_3$-substituted or 2-(protected amino)-4-(1,2,4-triazolyl)-6-$R_3$-substituted-pyrido[3,2-d]pyrimidine derivative with an appropriate Grignard reagent in a dry, polar, aprotic solvent. Examples of suitable solvents and suitable Grignard reagents are as detailed hereinabove with respect to the description of FIG. 1. Alternatively, 2-(protected amino)-4-chloro-6-$R_3$-substituted-pyrido[3,2-d]pyrimidine derivatives can also serve as excellent starting materials for a wide variety of organometallic cross-coupling reactions, such as detailed hereinabove with respect to the description of FIG. 1.

Figure 6:
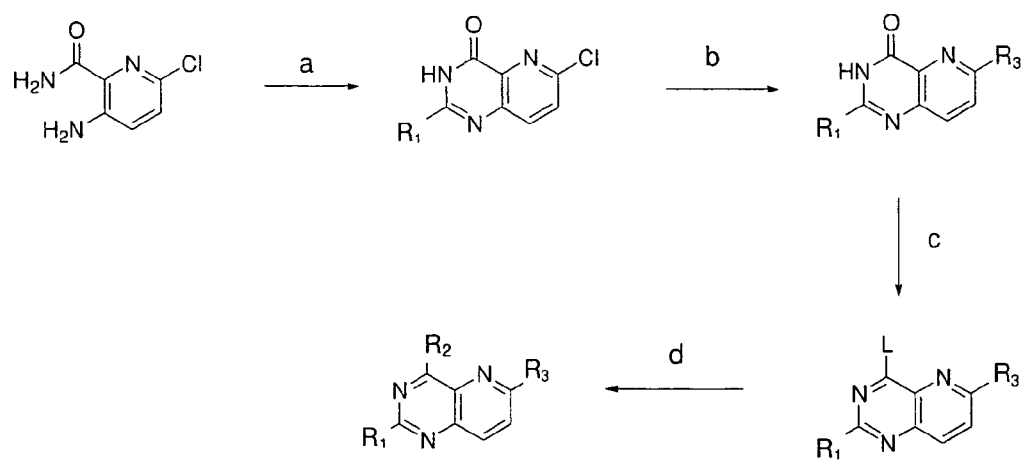
FIG. 6 schematically shows a method for making 2,4,6-trisubstituted pyrido(3,2-d)pyrimidine derivatives represented by the structural formula (I) through a series of intermediates wherein the substituent in position 4 may be hydroxy or a leaving group L such as chloro or 1,2,4-triazolyl, and wherein introduction of the substituent at position 6 is performed prior to introduction of the substituent at position 4, according to an embodiment of the present invention.

FIG. 6 schematically shows a method for making 2-$R_1$-substituted-4-$R_2$-substituted-6-$R_3$-substituted-pyrido(3,2-d)pyrimidine derivatives through a series of intermediates wherein the substituent in position 4 may be hydroxy or a leaving group L such as chloro or triazolyl. In step (a), condensation of 2-carboxamido-3-amino-6-chloro-pyridine with an appropriate ortho-ester, bearing the general formula $R_1C(O—C_{1-2}\ alkyl)_3$, leads to the formation of a 2-$R_1$-substituted-4-hydroxy-6-chloro-pyrido(3,2-d)pyrimidine derivative. Examples of commercially available ortho-esters include, but are not limited to, triethyl orthoacetate, triethyl orthoformate, triethyl orthopropionate, triethyl ortho-benzoate, trimethyl orthoacetate, trimethyl orthoformate, trimethyl orthobuty-rate, trimethyl orthobenzoate, and trimethyl orthovalerate, thus forming 2-$R_1$-substituted-4-hydroxy-6-chloro-pyrido(3,2-d)pyrimidine derivatives wherein $R_1$ may be hydrogen, methyl, ethyl, n-propyl, n-butyl or phenyl. The chlorine atom at position 6 is then used in step (b) for a wide variety of palladium-catalyzed cross-coupling reactions, such as, but not limited to, a Suzuki reaction (i.e. a reaction with an arylboronic acid, heteroaryl boronic acid or esters thereof leading to the formation of 2-$R_1$-substituted-4-hydroxy-6-(hetero)aryl-pyrido[3,2-d]pyrimidines), a Heck reaction (i.e. a reaction with a terminal alkene affording the corresponding 2-$R_1$-substituted-4-hydroxy-6-alkenyl-pyrido[3,2-d]pyrimidines), or a Sonogashira reaction (i.e. a reaction with a terminal alkyne affording the corresponding 2-$R_1$-substituted-4-hydroxy-6-alkynyl-pyrido[3,2-d]pyrimidine derivative). Activation of the tautomeric hydroxyl group at position 4 of the pyrido[3,2-d]pyrimidine scaffold then occurs in step (c) by introducing a readily leaving group (indicated by the letter L in FIG. 6) at position 4 of the pyrido[3,2-d]pyrimidine scaffold. Suitable leaving groups include, but are not limited to, chlorine and 1,2,4-triazolyl. The 2-$R_1$-substituted-4-(1,2,4-triazolyl)-6-$R_3$-substituted-pyrido[3,2-d]pyrimidine derivative can be obtained for instance by treating the 2-$R_1$-substituted-4-hydroxy-6-$R_3$-substituted pyrido[3,2-d]pyrimidine derivative with $POCl_3$ or 4-chlorophenyl phosphorodichloridate and 1,2,4-triazole in an appropriate solvent such as, but not limited to, pyridine, acetonitrile or dichloromethane. The 2-$R_1$-substituted-4-chloro-6-$R_3$-substituted-pyrido[3,2-d]pyrimidine derivative can be obtained by treating the 2-$R_1$-substituted-4-hydroxy- 6-$R_3$-substituted-pyrido[3,2-d]pyrimidine derivative with thionyl chloride or $POCl_3$. In order to introduce a carbon linker at position 4 of the scaffold, a nucleophilic displacement reaction is effected in step (d) by mixing the 2-$R_1$-substituted-4-chloro-6-$R_3$-substituted or 2-$R_1$-substituted-4-(1,2,4-triazolyl)-6-$R_3$-substituted-pyrido[3,2-d]pyrimidine derivative with an appropriate Grignard reagent in a dry, polar, aprotic solvent. Examples of suitable solvents and suitable Grignard reagents are as detailed hereinabove with respect to the description of FIG. 1. Alternatively, 2-$R_1$-substituted 4-chloro-6-$R_3$-substituted-pyrido[3,2-d]pyrimidine derivatives can also serve as excellent starting materials for a wide variety of organometallic cross-coupling reactions, such as detailed hereinabove with respect to the description of FIG. 1.

Figure 7:
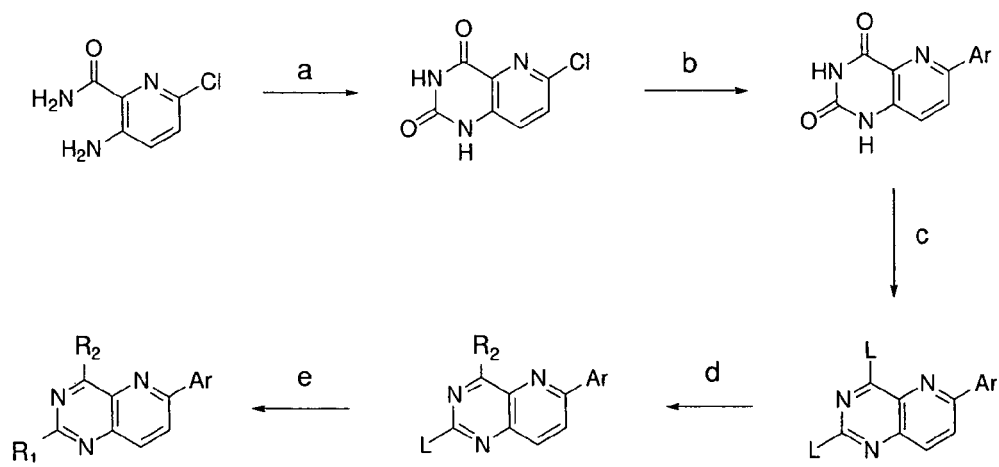
FIG. 7 schematically shows a method for making 2,4,6-trisubstituted pyrido(3,2-d)pyrimidine derivatives represented by the structural formula (I), through a series of intermediates wherein the substituents in positions 2 and 4 may independently be hydroxy or a leaving group L such as, but not limited to, chloro or 1,2,4-triazolyl, and wherein introduction of the substituent at position 6 is performed prior to introduction of the substituent at position 4, according to an embodiment of the present invention.

FIG. 7 schematically shows a method for making 2-$R_1$-substituted-4-$R_2$-substituted-6-$R_3$-substituted-pyrido(3,2-d)pyrimidine derivatives through a series of intermediates wherein the substituents in positions 2 and 4 may independently be hydroxy or a leaving group L such as chloro or triazolyl. Although FIG. 7 shows only an aryl substituent on position 6 ("Ar") of the pyrido[3,2-d]pyrimidine scaffold, the present method is not limited thereto and is also applicable to pyrido[3,2-d]pyrimidine derivatives wherein the 6-substituent is other than aryl, e.g. a heteroaryl, or a C-linked unsaturated substituent such as alkenyl or alkynyl. In step (a), 2-carboxamido-3-amino-6-chloro-pyridine is condensed with triphosgene in order to construct the 2,4-dihydroxy-pyrido[3,2-d]pyrimidine scaffold. The chlorine atom at position 6 is then used in step (b) for a wide variety of palladium-catalyzed cross-coupling reactions, such as, but not limited to, a Suzuki reaction (i.e. a reaction with an arylboronic acid, heteroaryl boronic acid or esters thereof leading to the formation of 2,4-dihydroxy-6-(hetero)aryl-pyrido[3,2-d]pyrimidines as shown in FIG. 7), a Heck reaction (i.e. a reaction with a terminal alkene affording the corresponding 2,4-dihydroxy-6-alkenyl-pyrido[3,2-d]pyrimidines, not shown in FIG. 7), or a Sonogashira reaction (i.e. a reaction with a terminal alkyne affording the corresponding 2,4-dihydroxy-6-alkynyl-pyrido[3,2-d]pyrimidine derivative, not shown in FIG. 7). Activation of the tautomeric hydroxyl groups at positions 2 and 4 of the pyrido[3,2-d]pyrimidine scaffold then occurs in step (c) by introducing a readily leaving group (indicated by the letter L in FIG. 7) at positions 2 and 4 of the pyrido[3,2-d]pyrimidine scaffold. Suitable leaving groups include, but are not limited to, chlorine and 1,2,4-triazolyl, and can be introduced as detailed with respect to the previous figures. The leaving capacity of the L groups at positions 2 and 4 of the pyrido[3,2-d]pyrimidine scaffold is however usually different, which makes it possible to selectively displace the L group (e.g. chlorine or 1,2,4-triazolyl) at position 4, in step (d), by reaction with an appropriate Grignard reagent in an appropriate solvent, as previously described with respect to FIG. 1. In the next step (e), the L group at position 2 (e.g. chlorine or 1,2,4-triazolyl) is displaced by a nucleophilic reagent having the structural formula $R_1H$ wherein $R_1$ is as defined with respect to structural formula (I), being a N-linked residue, such as ammonia, a primary amine, a secondary amine, or a reagent having the structural formula $(R_1)_mM$ wherein:

$R_1$ is as defined with respect to structural formula (I), being an oxide or thiolate, M is a metal selected from the group consisting of lithium, sodium, potassium, magnesium, zinc and aluminium, and m is the valency of the metal M.

In the above structural formula $(R_1)_mM$, m equals 1 when M is selected from the group consisting of lithium, sodium and potassium, m equals 2 when M is magnesium or zinc, and m equals 3 when M is aluminium. Suitable examples of nucleophilic reagents include, but are not limited to, sodium or potassium alkoxides, sodium or potassium alkenyl oxides, sodium or potassium cycloalkyl oxides, sodium or potassium cycloalkenyl oxides, sodium or potassium aryl oxides, sodium or potassium heterocyclic oxides, sodium or potassium heterocyclic-substituted alkyl oxides, and the correspondingly respective sodium or potassium thiolates. The respective oxides and thiolates may be commercially available or may also be prepared in situ using methods known to the skilled person. Alternatively, the chlorine atoms at positions 2 and 4 of the pyrido[3,2-d]pyrimidine scaffold are ideal starting materials for the construction of carbon linkers $R_1$ and $R_2$ by organometallic cross-coupling reactions, such as detailed hereinabove with respect to the description of FIG. 1.

In particular, suitable commercially available reagents for use in step (e) of FIG. 7 include, but are not limited to, 2-chlorobenzylamine, 4-chlorobenzylamine, 2,4-dichlorobenzylamine, 3,4-dichlorobenzylamine, 4-methoxybenzylamine, 4-methylbenzylamine, piperonylamine, 3,4-dimethoxybenzylamine, 3-methylbenzylamine, 3-fluorobenzylamine, 2-methylbenzylamine, 2-methoxybenzylamine, 3-methoxybenzylamine, 2-fluorobenzylamine, 4-fluorobenzylamine, 3,4-dihydroxybenzylamine, 3-chlorobenzylamine, 4-(trifluoromethoxy)benzylamine, 2,6-difluorobenzylamine, 3,5-bis(trifluoromethyl)benzylamine, 2,4-difluorobenzylamine, 2,5-difluoro benzylamine, 3,4-difluorobenzylamine, 2-(trifluoromethyl)benzylamine, 3-(trifluoromethyl)benzylamine, 2-bromobenzylamine, 4-bromobenzylamine, 2-chloro-6-fluorobenzylamine, 2,5-dimethylbenzylamine, 3,4,5-trimethoxybenzylamine, 2,4,6-trimethylbenzylamine, 2,4-dimethylbenzylamine, 2,3-dichlorobenzylamine, 1-naphthalenemethylamine, 3-Iodobenzylamine, 2-hydroxybenzylamine, 3-bromo benzylamine, 2,6-dichlorobenzylamine, 3,4-dihydro-2H-1,5-benzodioxepin-6-ylmethylamine, 2,3-dihydro-1,4-benzodioxin-6-ylmethylamine, 2,3-dihydro-1,4-benzodioxin-5-ylmethylamine, 1-benzofuran-5-ylmethylamine, 4-(2-thienyl)benzylamine, 3,4-dihydro-2H-1,5-benzodioxepin-7-ylmethylamine, 4-morpholino benzylamine, 4-(1H-pyrazol-1-yl)benzylamine, 4-(4-methylpiperazino)benzylamine, 2-piperidinobenzylamine, 3-(1H-Pyrrol-1-yl)benzylamine, 2-Morpholinobenzylamine, 4-(1H-pyrrol-1-yl)benzylamine, 2-chloro-6-phenoxy benzylamine, 2-(methylthio)benzylamine, 2-(trifluoromethoxy)benzylamine, 2,3-dimethylbenzylamine, 4-(trifluoromethyl)benzylamine, 3,5-dichlorobenzylamine, 2-(Aminomethyl)-3-fluoroaniline, 3-chloro-4-fluorobenzylamine, 2,5-dimethoxybenzylamine, 2,5-dichloro benzylamine, 2,6-dimethoxybenzylamine, 2,4-dichloro-6-methylbenzylamine, 3-chloro-4-methylbenzylamine, 4-fluoro-3-(trifluoromethyl)benzylamine, 4-fluoro-2-(trifluoromethyl)benzylamine, 3-piperidin-1-ylmethyl benzylamine, 1-benzothiophen-5-ylmethylamine, 4-(Morpholinomethyl)benzylamine, (3-((4-methylpiperidino)methyl)phenyl)methanamine, (4-Piperidinophenyl)methylamine, (3-piperidinophenyl)methylamine, 1-[2-(4-methylpiperazin-1-yl)phenyl]methanamine, (1,4-dimethyl-1,2,3,4-tetrahydroquinoxalin-6-yl)methylamine, 3-(Trifluoromethoxy)benzylamine, 4-bromo-2-fluorobenzylamine, 2-(1 h-pyrazol-1-yl)benzylamine, tert-butyl 4-(2-(aminomethyl)phenyl)piperazine-1-carboxylate, (3-Morpholinophenyl)methylamine, tert-Butyl N-[4-(aminomethyl)phenyl]carbamate, [2-(1H-Pyrrol-1-yl)phenyl]methylamine, 1-[3-(4-Methylpiperazin-1-yl)phenyl]methanamine, [4-(1- pyrrolidinyl)phenyl]methanamine, (3-pyrrolidin-1-ylphenyl)methylamine, [4-(2-morpholinoethoxy)phenyl]methylamine, [2-(2-Morpholinoethoxy)phenyl]methylamine, [3-(2-Morpholinoethoxy)phenyl]methylamine, [3-(morpholinomethyl)phenyl]methylamine, [4-(piperidinomethyl)phenyl]methylamine, {4-[(4-Methylpiperazin-1-yl)methyl]phenyl}methylamine, [4-(2-furyl)phenyl]methylamine, tert-Butyl 4-[4-(aminomethyl)phenyl]tetrahydro-1(2H)-pyrazinecarboxylate, (2,2-dimethyl-2,3-dihydro-1-benzofuran-7-yl)methylamine, [3-(1h-1,2,4-triazol-1-yl)phenyl]methylamine, (4-thien-3-ylphenyl)methylamine, 1-[2-(morpholin-4-ylmethyl)phenyl]methanamine, {2-[(4-methylpiperazin-1-yl)methyl]phenyl}methylamine, [3-(2-furyl)phenyl]methylamine, (3-thien-2-ylphenyl)methylamine, [2-(2-furyl)phenyl]methylamine, 4-(Pyrrolidin-1-ylmethyl)benzylamine, 4-[(4-methylperhydro-1,4-diazepin-1-yl)methyl]benzylamine, 4-[2-(dimethylamino)ethoxy]benzylamine, (2-Pyrrolidin-1-ylphenyl)methylamine, [3-(1-Pyrrolidinylmethyl)phenyl]methanamine, (3-thien-3-ylphenyl)methylamine, 2-[2-(dimethylamino)ethoxy]benzylamine, 2-(phenoxymethyl)benzylamine, (1-methyl-1h-indol-4-yl)methylamine, 4-(4-methylperhydro-1,4-diazepin-1-yl)benzylamine, (1-methyl-1H-indol-6-yl)methylamine, [3-(1,3-thiazol-2-yl)phenyl]methylamine, 3-(1H-pyrazol-1-ylmethyl)benzylamine, (1-methyl-1H-indol-5-yl)methylamine, 3-(phenoxymethyl)benzylamine, 2-morpholino-5-(trifluoromethyl)benzylamine, [4-(1,3-Thiazol-2-yl)phenyl]methylamine, 3-(1-Methyl-1H-pyrazol-3-yl)benzylamine, 2-(4-Methylperhydro-1,4-diazepin-1-yl)benzylamine, 4-[3-(dimethylamino)propoxy]benzylamine, 3-(2-Methyl-1H-imidazol-1-yl)benzylamine, 4-(2-Methyl-1H-imidazol-1-yl)benzylamine, 2-(2-methyl-1H-imidazol-1-yl)benzylamine, [4-(tetrahydropyran-4-yloxy)phenyl]methylamine, 3-[3-(dimethylamino)propoxy]benzylamine, 2-[3-(dimethylamino)propoxy]benzylamine, 3-pyrimidin-2-ylbenzylamine, 4-(1-methyl-1H-pyrazol-3-yl)benzylamine, 3-(1-methyl-1h-pyrazol-5-yl)benzylamine and 1-(1-benzothien-7-yl)methanamine.

Most of these methods make use of a boronic acid, or a pinacol ester thereof, for introducing a substituent at position 6 of the pyrido(3,2-d)pyrimidine core structure. For this purpose, suitable aryl-boronic acids or pinacol esters thereof include, but are not limited to, the following commercially available materials wherein the aryl group is 3-acetamidophenyl, 4-acetamidophenyl, 4-acetylphenyl, 3-acetylphenyl, 2-acetylphenyl, 5-acetyl-2-chlorophenyl, 4-acetyl-3-fluorophenyl, 5-acetyl-2-fluorophenyl, 4-(4'-allyloxycarbonylpiperazino)phenyl, 3-aminocarbonyl-phenyl, 4-aminocarbonylphenyl, 2-amino-5-chlorophenyl, 4-amino-3-methoxyphenyl, 3-aminophenyl, 2-amino-4-methylphenyl, 2-amino-5-methylphenyl, 4-amino-2-methylphenyl, 5-amino-2-methylphenyl, 4-amino-3-nitrophenyl, 3-aminophenyl, 2-aminophenyl, 4-aminophenyl, 4-benzyloxyphenyl, 3-benzyloxyphenyl, 2-benzyloxyphenyl, 4-benzyloxy-2-fluorophenyl, 4-benzyloxy-3-fluorophenyl, 3-benzyloxy-4-methoxyphenyl, 4-biphenyl, 3,5-bis(trifluoromethyl)benzene, 4-bromophenyl, 3-bromophenyl, 4-bromo-2,5-dimethylphenyl, 2-bromo-5-fluorophenyl, 2-bromo-6-fluorophenyl, 4-n-butylphenyl, 4-isobutylphenyl, 4-carboxyphenyl, 3-carboxyphenyl, 2-carboxyphenyl, 2-carboxy-5-fluorophenyl, 4-carboxy-3-fluorophenyl, 4-carboxy-2-chlorophenyl, 5-carboxy-2-chlorophenyl, 4-carboxy-3-chlorophenyl, 3-carboxyphenyl, 3-(3-carboxypropionylamino)phenyl, 4-(3-carboxypropionylamino)phenyl, 2-chloro-5-formylphenyl, 3-chloro-4-fluorophenyl, 2-chloro-4-fluorophenyl, 4-chloro-2-fluorophenyl, 3-chloro-4-hydroxy-5-methoxyphenyl, 2-chloro-5-hydroxymethylphenyl, 3-chloro-5-methoxyphenyl, 2-chloro-4-methylphenyl, 2-chloro-5-methylphenyl, 2-chloro-5-trifluoromethoxyphenyl, 3-chloro-5-trifluoromethylphenyl, 4-chloro-2-trifluoromethylphenyl, 4-chlorophenyl, 3-chlorophenyl, 2-chlorophenyl, 4-cyanomethoxyphenyl, 3-cyanomethoxyphenyl, 2-cyanomethoxyphenyl, 4-cyanophenyl, 3-cyanophenyl, 2-cyanophenyl, 3,5-dibromophenyl, 3-(N-cyclopropylaminocarbonyl)phenyl, 2,6-dichlorophenyl, 3,4-dichlorophenyl, 2,4-dichlorophenyl, 2,3-dichlorophenyl, 3,5-dichlorophenyl, 3-(N,N-diethylaminocarbonyl)phenyl, 3,5-difluorophenyl, 3,5-difluoro-2-methoxyphenyl, 3,4-difluorophenyl, 2,6-difluorophenyl, 2,5-difluorophenyl, 2,4-difluorophenyl, 2,3-difluorophenyl, 4-(N,N-dimethylamino)phenyl, 3-(N,N-dimethylamino)phenyl, 2-(N,N-dimethylamino)phenyl, 3-(N,N-dimethylaminocarbonyl)phenyl, 3-[(N',N'-dimethylamino)ethylaminocarbonyl]phenyl, 4-[(N',N'-dimethylamino)ethylaminocarbonyl]phenyl, 3,5-dimethylphenyl, 3,4-dimethylphenyl, 2,6-dimethylphenyl, 2,6-dimethoxyphenyl, 2,5-dimethoxyphenyl, 2,4-dimethoxyphenyl, 3-[1,3]dioxolan-2-ylmethoxyphenyl, 4-ethoxyphenyl, 2-ethoxyphenyl, 3-(ethoxycarbonyl)methoxyphenyl, 4-(ethoxycarbonyl)methoxyphenyl, 4-ethoxycarbonylphenyl, 3-ethoxycarbonylphenyl, 2-ethoxy carbonylphenyl, 4-(3-ethoxycarbonylpiperidino)carboxamidophenyl, 4-ethylphenyl, 4-fluorophenyl, 3-fluorophenyl, 2-fluorophenyl, 3-fluoro-4-formylphenyl, 4-fluoro-3-formylphenyl, 4-fluoro-2-methylphenyl, 2-fluoro-5-methylphenyl, 2-fluoro-5-methoxyphenyl, 3-fluoro-4-methoxyphenyl, 5-fluoro-2-methoxycarbonylphenyl, 2-fluoro-4-trifluoromethylphenyl, 2-formylaminophenyl, 3-formylaminophenyl, 4-formylaminophenyl, 2-formyl-5-methoxyphenyl, 3-formyl-4-methoxyphenyl, 5-formyl-2-methoxyphenyl, 2-formyl-5-methylphenyl, 4-formylphenyl, 3-formylphenyl, 2-formylphenyl, 4-hydroxy-3,5-dimethylphenyl, 3-(2-hydroxyethyl)-aminocarbonyl phenyl, 4-(2-hydroxyethyl)-aminocarbonyl-phenyl, 3-hydroxy-4-methoxycarbonyl phenyl, 4-hydroxy-3-methoxyphenyl, 4-(hydroxymethyl)phenyl, 3-(hydroxymethyl)phenyl, 4-hydroxy-3-nitrophenyl, 4-hydroxyphenyl, 3-hydroxyphenyl, 2-hydroxy phenyl, 4-isopropoxyphenyl, 4-(4-isopropylpiperazinyl)phenyl, 4-isopropylphenyl, 4-methanesulfonamido-phenyl, 3-methanesulfonamidophenyl, 2-methane sulfonamidophenyl, 4-methanesulfonylphenyl, 2-methoxy-5-formylphenyl, 5-methoxy-2-formylphenyl, 4-methoxy-2-formylphenyl, 4-methoxycarbonylphenyl, 3-methoxy carbonylphenyl, 2-methoxycarbonylphenyl, 3-methoxy-4-methoxycarbonylphenyl, 4-methoxy-3-nitrophenyl, 4-methoxyphenyl, 3-methoxyphenyl, 2-methoxyphenyl, 2-methoxy-5-methylphenyl, 4-N-methylcarboxamidophenyl, 4-methylphenyl, 3-methylphenyl, 2-methylphenyl, 4-(N-methylamino)phenyl, 3-(4-methylpiperazine-1-carbonyl)phenyl, 4-(4-methylpiperazine-1-carbonyl)phenyl, 4-(methylthio)phenyl, 3-(methylthio)phenyl, 2-(methylthio)phenyl, 4-morpholinophenyl, 4-(morpholinocarbonyl)phenyl, 2-morpholinomethyl)phenyl, 4-nitrophenyl, 3-nitro phenyl, 2-nitrophenyl, 4-phenoxyphenyl, 4-(N-phenylaminomethyl)phenyl, 4-(phenylcarbonyl)phenyl, 4-(piperazine-1-carbonyl)phenyl, 4-piperazinylphenyl, 3-succinamidophenyl, 4-succinamidophenyl, sulfamoylphenyl, 2-(toluene-4-sulfonamido)phenyl, 3-(toluene-4-sulfonamido)phenyl, 4-(toluene-4-sulfonamido) phenyl, 4-(tert-butoxycarbonylamino)-3-methoxyphenyl, 2-(tert-butoxycarbonyl)phenyl, 3-(tert-butoxycarbonyl)phenyl, 4-(tert-butoxycarbonyl)phenyl, 4-tert-butyl phenyl, 4-(tetrahydro-2H-pyran-2-yloxy)phenyl, 4-(2-thienyl)phenyl, 4-trifluoro methoxyphenyl, 4-(trimethylammonium)methylphenyl, 2,4,6-trimethylphenyl, 3,4,5-trifluorophenyl, 2,3,4-trifluorophenyl, 3-trifluoromethylphenyl, 4-trifluoromethoxy phenyl, 3-trifluoromethoxyphenyl, 2-trifluoromethylphenyl, 3-trifluoromethylphenyl, 4-trifluoromethylphenyl, 3,4,5-trimethoxyphenyl, 4-vinylphenyl, 6-benzyloxy-2-naphthyl, 1-naphthalyl, 2-naphthalyl, (O,O-dimethylphosphonyl)methylphenyl or 1-biphenylyl.

For the purpose of making the compounds of the present invention, suitable heterocyclic-boronic acids or pinacol esters thereof include, but are not limited to, the following commercially available materials wherein the heterocyclic group is 3,4-methylenedioxyphenyl (benzodioxolyl), 2-acetamidopyridin-5-yl, 2-aminopyridin-5-yl, 2-aminopyrimidin-5-yl, 1,4-benzodioxan-6-yl, 2-benzothienyl, 1-benzothiophen-3-yl, 1-benzothiophen-2-yl, 2-benzyloxypyridin-5-yl, 1-benzyl-1H-pyrazol-4-yl, 2-bromo-3-chloropyridin-4-yl, 5-bromo-2,3-dihydrobenzo[b]furan-7-yl, 2-bromo-3-methylpyridin-5-yl, 3-bromopyridin-5-yl, 2-bromopyridin-5-yl, 5-bromothien-2-yl, 2-chloro-6-isopropylpyridin-3-yl, 2-chloro-3-methylpyridin-5-yl, 2-[4-(4-chlorophenyl sulfonyl)-piperazin-1-yl]pyridin-5-yl, 2-chloropyrid-4-yl, 2-chloropyrid-5-yl, 5-chloro thien-2-yl, dibenzo[b,d]furan-4-yl, 2-chloro-3-fluoropyridin-4-yl, dibenzo[b,d]thien-4-yl, 3,4-dihydro-2H-1,5-benzodioxepin-7-yl, 3,6-dihydro-2H-pyridine-1-tert-butoxy carbonyl, 2,5-dibromo-3-pyridinyl, 2,6-dichloro-pyridin-3-yl, 2,3-dihydro-1-benzofuran-5-yl, 2,6-dimethoxypyridin-5-yl, 2,6-dimethoxypyridin-3-yl, 2,4-dimethoxypyrimidin-5-yl, 3,5-dimethylisoxazol-4-yl, 2-(3-N,N-dimethylaminopropoxy)pyridin-5-yl, 3,5-dimethyl-pyrazol-4-yl, 1-[1,3]dioxolan-2-ylmethyl-1H-pyrazol-4-yl, 2,4-dioxo-1,2,3,4-tetrahydro-5-pyrimidinyl, 2,4-di(tert-butoxy)pyrimidin-5-yl, 2-ethoxypyridin-3-yl, 2-fluoro-3-methylpyridin-5-yl, 2-fluoropyridin-3-yl, 2-fluoropyridin-5-yl, 5-formyl-2-furyl, 5-formylthien-2-yl, furan-3-yl, furan-2-yl, 2-hydroxypyridin-5-yl, 5-indolyl, 1-isobutyl-1H-pyrazol-4-yl, isoquinolin-4-yl, 2-methoxypyridin-3-yl, 2-methoxypyrimidin-5-yl, 5-methyl-1-benzothiophen-2-yl, 1-(3-methylbutyl)-1H-pyrazol-4-yl, 5-methylfuran-2-yl, 1-methylindol-5-yl, 5-methyl-3-phenyl-4-isoxazolyl, 5-(methylthio)thien-2-yl, 2-(4-methylpiperazinyl)pyridin-4-yl, 2-(4-methylpiperazinyl)pyridin-5-yl, 1-methyl-1H-pyrazol-4-yl, 3-methylpyridin-2-yl, 5-methylpyridin-2-yl, 5-methylpyridin-3-yl, 4-methylthien-2-yl, 5-methylthien-2-yl, 2-methoxypyridin-5-yl, 2-(2-morpholino-ethylamino)-pyridin-5-yl, 2-(2-morpholinoethyl)-1H-pyrazol-4-yl, 2-(morpholin-1-yl)-pyridin-5-yl, 1-(phenylsulfonyl)-1H-indol-3-yl, 5-phenyl-2-thienyl, 2-(piperazin-1-yl)-pyridin-5-yl, 2-(piperazin-1-yl)-pyridin-4-yl, 1-propyl-1H-pyrazol-4-yl, pyrazol-4-yl, pyridin-4-yl, pyridin-3-yl, pyrimidin-5-yl, 4-phenoxathiinyl, quinolin-8-yl, quinolin-3-yl, 2-(4-tert-butoxycarbonylpiperazinyl)-pyrid-4-yl, 1-tert-butoxycarbonyl-1H-pyrazol-4-yl, 1-tert-butoxycarbonyl-2-pyrrolyl, 1-(tert-butoxycarbonyl)-5-bromo-1H-indol-2-yl, 1-(tert-butoxycarbonyl)-1H-indol-5-yl, 1-(tert-butoxycarbonyl)-5-methoxy-1H-indol-2-yl, 1-thianthrenylthien-3-yl, thien-3-yl, thien-2-yl or 1,3,5-trimethyl-1H-pyrazol-4-yl.

Surprisingly, in another aspect of the present invention, it has been found that the reaction of certain pyrido(3,2-d)pyrimidine substrates with different types of organometallic reagents can be efficiently catalyzed by iron salts or complexes under certain conditions specified below. This aspect exhibits substantial advantages over prior art methodologies. Most notable aspects are the fact that (i) inexpensive, stable, commercially available and toxicologically acceptable iron salts or iron complexes as the catalysts or pre-catalysts afford excellent yields for the derivatives of the invention, (ii) the reaction can be performed under "ligand-free" conditions, and (iii) the reaction times are usually very short.

This embodiment provides a method of making a pyrido(3,2-d)pyrimidine derivative according to the first embodiment of the invention, comprising a step of reacting a pyrido(3,2-d)pyrimidine intermediate represented by the structural formula:

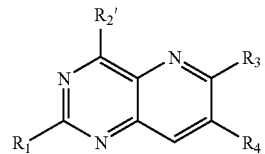

wherein:
$R_1$, $R_3$, $R_4$, $R_6$, $R_7$, $R_8$, $R_8'$, $R_9$, $R_9'$, $R_{10}$, $R_{11}$, $R_{12}$, $R_{13}$ and $R_{14}$ are defined above for formula (I); and
$R_2'$ is a nitrogen-containing aromatic heterocyclyl group attached through the nitrogen atom to position 4 of the pyrido(3,2-d)pyrimidinyl moiety,
with at least one organometallic reagent of the formula $R_2MZ$ wherein $R_2$ is defined as above, M is a metal selected from the group consisting of magnesium, calcium, zinc and manganese, and Z is an anionic ligand, in the presence of at least one catalyst comprising one or more iron salts or complexes.

In particular, $R_2'$ may be 1,2,4-triazolyl, 1,2,3-triazolyl, 1H-tetrazolyl, 4-dimethylaminopyridyl or 2-diethylaminopyridyl. In particular, the anionic ligand Z may be halogen, $C_{1-7}$ alkyl or aryl.

Preferably, the reaction step of this embodiment is performed in a solvent medium containing one or more ethers and/or hydrocarbons and/or aprotic dipolar solvents. Suitable components for the solvent medium include, but are not limited to, diethyl ether, tetrahydrofuran, tetrahydropyran, methyl-tetrahydrofuran, 1,4-dioxane, tert-butyl methyl ether, dibutyl ether, di-isopropyl ether, dimethoxyethane, dimethoxymethane, pentane, hexane, heptane, octane, isooctane, cyclohexane, benzene, toluene, xylene, cymene, petrol ether, decaline, dimethylformamide, dimethylacetamide, dimethylsulfoxide, N-methylpyrrolidinone, tetramethylurea, sulfolane, diethyl carbonate, 1,3-dimethyltetrahydro-2(1H)-pyrimidinone, hexamethylphosphoric acid triamide, N,N,N',N'-tetramethylethylenediamine, and mixtures thereof.

In particular the organometallic reagent may be a Grignard reagent wherein M is magnesium and Z is halogen, preferably chloro or bromo. Alternatively, the organometallic reagent may be a diorganomagnesium reagent wherein M is magnesium, $R_2$ is $C_{1-7}$ alkyl and Z is $C_{1-7}$ alkyl. Alternatively, the organometallic reagent may be a diorganozinc reagent wherein M is zinc, $R_2$ is $C_{1-7}$ alkyl or aryl, and Z is $C_{1-7}$ alkyl or aryl, such as but not limited to diphenylzinc.

The active iron catalyst used in this method may be formed in situ under suitable conditions from suitable iron catalyst precursors. The iron salts or complexes used as a catalyst usually contain iron in an oxidation state of −2, −1, 0, +1, +2 or +3. Suitable examples include, but are not limited to, $FeF_2$, $FeF_3$, $FeCl_3$, $FeCl_3[P(phenyl)_3]$, $Fe(ethoxy)_2$, $Fe(ethoxy)_3$, $FeCl_2[P(phenyl)_3]_2$, $FeCl_2[1,2-bis-(diphenylphosphino)-ethane]$, $Fe(acetylacetonate)_2$, $Fe(acetylacetonate)_3$, tris-(trifluoroacetylacetonato)iron (III), tris-(hexafluoroacetylacetonato)iron (III), tris-(dibenzoylmethido)iron (III), tris-(2,2,6,6-tetramethyl-3,5-diheptanedionato)iron (III), $FeBr_2$, $FeBr_3$, $FeI_2$, Fe(II)acetate, Fe(II)oxalate, Fe(II)stearate, Fe(III)citrate, Fe(III)pivalate, Fe(II)-D-gluconate, $FePO_4$, $Fe(NO_3)_3$, FeSO$_4$, K$_3$Fe(CN)$_6$, ferrocene, bis(pentamethylcyclopentadienyl)iron, bis(indenyl)iron, Fe(II)phthalocyanin, Fe(III) phthalocyanin chloride, Fe(III)-2,2,6,6-tetramethyl-3,5-heptanedioate, Fe(CO)$_5$, Fe[N,N-ethylenebis(salicylidenamidato)]Cl, 5,10,15,20-tetraphenyl-21H,23H-porphin-iron(III) halides and 5,10,15,20-tetrakis (pentafluorophenyl)-21H,23H-porphin-iron(III) halides. Preferred catalysts are those being at least partly soluble in the solvent medium. The effective amount of catalyst to be used in the method of this embodiment can be varied within a wide range, preferably from about 0.1 mole % to about 10 mole % with respect to the pyrido(3,2-d)pyrimidine intermediate.

In particular, the invention relates to specific pyrido(3,2-d) pyrimidine derivatives selected from the group consisting of:
1-[4-(2-amino-4-cyclopropyl-pyrido[3,2-d]pyrimidin-6-yl)-phenyl]-pyrrolidin-2-one,
4-Cyclopropyl-6-(4-fluoro-phenyl)-pyrido[3,2-d]pyrimidin-2-ylamine,
6-(4-Fluoro-phenyl)-4-isopropyl-pyrido[3,2-d]pyrimidin-2-ylamine,
4-methyl-6-(4-fluorophenyl)-pyrido[3,2-d]pyrimidin-2-ylamine,
4-(2-[1,3]Dioxan-2-yl-ethyl)-6-(4-fluoro-phenyl)-pyrido[3,2-d]pyrimidin-2-ylamine,
6-(5-Amino-pyrazin-2-yl)-4-ethyl-pyrido[3,2-d]pyrimidin-2-ylamine,
1-[4-(2-Amino-4-ethyl-pyrido[3,2-d]pyrimidin-6-yl)-phenyl]-pyrrolidin-2-one,
4-but-3-enyl-6-(4-fluoro-phenyl)-pyrido[3,2-d]pyrimidin-2-ylamine,
6-(4-fluoro-phenyl)-4-isobutyl-pyrido[3,2-d]pyrimidin-2-ylamine,
4-ethyl-6-(4-fluoro-phenyl)-pyrido[3,2-d]pyrimidin-2-ylamine,
6-(4-fluoro-phenyl)-4-n-propyl-pyrido[3,2-d]pyrimidine,
N-[4-(2-amino-4-n-propyl-pyrido[3,2-d]pyrimidin-6-yl)-phenyl]-acetamide, and
6-(4-fluorophenyl)-4-propyl-pyrido[3,2-d]pyrimidin-2-ylamine.

In another particular embodiment, the invention relates to a group of di-, tri- and tetra-substituted pyrido(3,2-d)pyrimidine derivatives, as well as pharmaceutical compositions comprising such pyrido(3,2-d)pyrimidine derivatives as a biologically active principle, having the above general formula (I) and being in the form of a pharmaceutically acceptable salt. The latter include any therapeutically active non-toxic addition salt which di-, tri- and tetra-substituted pyrido (3,2-d)pyrimidine derivatives having the structural formula (I) are able to form with a salt-forming agent. Such addition salts may conveniently be obtained by treating the di-, tri- and tetra-substituted pyrido(3,2-d)pyrimidine derivatives of the present invention with an appropriate salt-forming acid or base. For instance, di-, tri- and tetra-substituted pyrido(3,2-d)pyrimidine derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as, but not limited to, hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzene-sulfonate, p-toluenesulfonate, salicylate, p-aminosalicylate, pamoate, bitartrate, camphorsulfonate, edetate, 1,2-ethanedisulfonate, fumarate, glucoheptonate, gluconate, glutamate, hexylresorcinate, hydroxynaphtoate, hydroxyethanesulfonate, mandelate, methylsulfate, pantothenate, stearate, as well as salts derived from ethanedioic, propanedioic, butanedioic, (Z)-2-butenedioic, (E)2-butenedioic, 2-hydroxybutanedioic, 2,3-dihydroxybutane-dioic, 2-hydroxy-1,2,3-propanetricarboxylic and cyclohexanesulfamic acids and the like.

Di-, tri- and tetra-substituted pyrido(3,2-d)pyrimidine derivatives represented by the structural formula (I) and having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chloroprocaine, choline, diethanolamine, ethylene-diamine, N-methylglucamine, procaine and the like.

Reaction conditions for treating the di-, tri- and tetra-substituted pyrido(3,2-d)pyrimidine derivatives having the structural formula (I) of this invention with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water-solubility, lower toxicity, greater stability and/or slower dissolution rate to the di-, tri- or tetra-substituted pyrido(3,2-d)pyrimidine derivative of this invention.

The present invention further provides the use of a di-, tri- or tetra-substituted pyrido(3,2-d)pyrimidine derivative represented by the structural formula (I), or a pharmaceutically acceptable salt or a solvate thereof, as a biologically-active ingredient, i.e. an active principle, especially as a medicine or a diagnostic agent or for the manufacture of a medicament or a diagnostic kit. In particular the said medicament may be for the prevention or treatment of viral infections, especially infections due to Flaviridae, and pathologic conditions associated therewith such as, but not limited to, hepatitis C.

The invention further relates to a pharmaceutical composition comprising:
(a) one or more di-, tri- or tetra-substituted pyrido(3,2-d) pyrimidine derivatives represented by the structural formula (I), and
(b) one or more pharmaceutically acceptable carriers.

In another embodiment, this invention provides combinations, preferably synergistic combinations, of one or more di-, tri- or tetra-substituted pyrido(3,2-d)pyrimidine derivatives represented by the structural formula (I) with one or more other antiviral agents. As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein below, this principle may be applied to a number of desirable effects such as, but not limited to, an activity against viral infection.

The present invention thus further relates to a pharmaceutical composition or combined preparation having synergistic effects against a viral infection and containing:
(a) one or more anti-viral agents, and
(b) at least one di-, tri- or tetra-substituted pyrido(3,2-d)pyrimidine derivative represented by the structural formula (I), and
(c) optionally one or more pharmaceutical excipients or pharmaceutically acceptable carriers,
for simultaneous, separate or sequential use in the treatment or prevention of a viral infection.

Suitable anti-viral agents for inclusion into the synergistic antiviral compositions or combined preparations of this invention include, for instance, retroviral enzyme inhibitors belonging to categories well known in the art, such as HIV-1 IN inhibitors, nucleoside reverse transcriptase inhibitors (e.g. zidovudine, lamivudine, didanosine, stavudine, zalcitabine and the like), non-nucleoside reverse transcriptase inhibitors (e.g. nevirapine, delavirdine and the like), other reverse transcriptase inhibitors (e.g. foscarnet sodium and the like), and HIV-1 protease inhibitors (e.g. saquinavir, ritonavir, indinavir, nelfinavir and the like). Other suitable antiviral agents include for instance acemannan, acyclovir, adefovir, alovudine, alvircept, amantadine, aranotin, arildone, atevirdine, pyridine, cidofovir, cipamfylline, cytarabine, desciclovir, disoxaril, edoxudine, enviradene, enviroxime, famciclovir, famotine, fiacitabine, fialuridine, floxuridine, fosarilate, fosfonet, ganciclovir, idoxuridine, kethoxal, lobucavir, memotine, methisazone, penciclovir, pirodavir, somantadine, sorivudine, tilorone, trifluridine, valaciclovir, vidarabine, viroxime, zinviroxime, moroxydine, podophyllotoxin, ribavirine, rimantadine, stallimycine, statolon, tromantadine and xenazoic acid, and their pharmaceutically acceptable salts.

Especially relevant to this aspect of the invention is the inhibition of the replication of hepatitis C virus, in particular in human beings and other mammals such as primates. Therefore, of particular relevance in the context of HCV prevention or treatment is co-administration with one or more other agents aiming at HCV inhibition well known in the art, such as but not limited to, (pegylated) interferon alpha, ribavirin, an NS3 protease inhibitor (such as VX-950), or nucleoside- or non-nucleoside-based inhibitors of NS5B polymerase. Synergistic activity of the pharmaceutical compositions or combined preparations of this invention against viral infection may be readily determined by means of one or more tests such as, but not limited to, the isobologram method, as previously described by Elion et al. in *J. Biol. Chem*. (1954) 208:477-488 and by Baba et al. in *Antimicrob. Agents Chemother*. (1984) 25:515-517, using $EC_{50}$ for calculating the fractional inhibitory concentration (hereinafter referred as FIC). When the minimum FIC index corresponding to the FIC of combined compounds (e.g., $FIC_x + FIC_y$) is equal to 1.0, the combination is said to be additive; when it is between 1.0 and 0.5, the combination is defined as sub-synergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

The pharmaceutical composition or combined preparation with synergistic activity against viral infection, especially HCV, according to the present invention may contain the di-, tri- or tetra-substituted pyrido(3,2-d)pyrimidine derivative having the structural formula (I) over a broad content range depending on the contemplated use and the expected effect of the preparation. Generally, the di-, tri- or tetra-substituted pyrido(3,2-d)pyrimidine derivative content of the combined preparation is within the range of from 0.1 to 99.9% by weight, preferably from 1 to 99% by weight, more preferably from about 5 to 95% by weight.

The pharmaceutical compositions and combined preparations according to this invention may be administered orally or in any other suitable fashion. Oral administration is preferred and the pharmaceutical composition or preparation may have the form of a tablet, aqueous dispersion, dispersable powder or granule, emulsion, hard or soft capsule, syrup, elixir or gel. The dosing forms may be prepared using any method known in the art for manufacturing these pharmaceutical compositions and may comprise as additives sweeteners, flavoring agents, coloring agents, preservatives and the like. Carrier materials and excipients are detailed hereinbelow and may include, inter alia, calcium carbonate, sodium carbonate, lactose, calcium phosphate or sodium phosphate; granulating and disintegrating agents, binding agents and the like. The pharmaceutical composition or combined preparation of this invention may be included in a gelatin capsule mixed with any inert solid diluent or carrier material, or has the form of a soft gelatin capsule, in which the ingredient is mixed with a water or oil medium. Aqueous dispersions may comprise the biologically active composition or combined preparation in combination with a suspending agent, dispersing agent or wetting agent. Oil dispersions may comprise suspending agents such as a vegetable oil. Rectal administration is also applicable, for instance in the form of suppositories or gels. Injection (e.g. intramuscularly or intraperiteneously) is also applicable as a mode of administration, for instance in the form of injectable solutions or dispersions, depending upon the disorder to be treated and the condition of the patient.

The term "pharmaceutically acceptable carrier or excipient" as used herein in relation to pharmaceutical compositions and combined preparations means any material or substance with which the active principle, i.e. the di-, tri- or tetra-substituted pyrido(3,2-d)pyrimidine derivative having the structural formula (I), and optionally the additional antiviral agent, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions or preparations of the present invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the di-, tri- or tetra-substituted pyrido(3,2-d)pyrimidine derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. They may also be prepared by micronisation, for instance in view to obtain them in the form of microspheres usually having a diameter of about 1 to 10 µm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates include, but are not limited to, the sodium, calcium or alcanolamine salts of dodecylbenzene sulphonic acid or dibutyl-naphthalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphoshatidyl-choline and their mixtures.

Suitable non-ionic surfactants include, but are not limited to, polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants include, but are not limited to, water-soluble adducts of polyethylene oxide with poylypropylene glycol, ethylenediamino-polypropylene glycol containing 1 to 10 carbon atoms in the alkyl chain, which adducts preferably contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants include, but are not limited to, nonylphenol-polyethoxyethanol, castor oil polyglycolic ethers, polypropylene/polyethylene oxide adducts, tributylphenoxypolyethoxyethanol, polyethyleneglycol and octylphenoxy-polyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include, but are not limited to, quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-$C_{1-4}$ alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions and combined preparations of the invention. Control release compositions may thus be achieved by selecting appropriate pharmaceutically acceptable polymer carriers such as for example polyesters, polyamino-acids, polyvinyl-pyrrolidone, ethylene-vinyl acetate copolymers, methylcellulose, carboxy-methylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

Other modes of local drug administration can also be used. For example, the selected active agent may be administered topically, in an ointment, gel or the like, or transdermally, using a conventional transdermal drug delivery system.

Since, in the case of combined preparations including the di-, tri- or tetra-substituted pyrido(3,2-d)pyrimidine derivative of the present invention and an additional antiviral agent, both active ingredients do not necessarily bring out their synergistic therapeutic effect directly at the same time in the patient to be treated, the said combined preparation may be in the form of a medical kit or package containing the two ingredients in separate but adjacent form. In the latter context, each ingredient may therefore be formulated in a way suitable for an administration route different from that of the other ingredient, e.g. one of them may be in the form of an oral or parenteral formulation whereas the other is in the form of an ampoule for intravenous injection or an aerosol.

The present invention further relates to a method for preventing or treating a viral infection or a pathologic condition associated therewith, including hepatitis C in a patient, preferably a mammal such as a primate, more preferably a human being. The method of this invention consists of administering to the patient in need thereof a therapeutically effective amount of a di-, tri- or tetra-substituted pyrido(3,2-d)pyrimidine derivative having the structural formula (I), optionally together with an effective amount of another antiviral agent, or a pharmaceutical composition comprising the same, such as disclosed above in extensive details. The therapeutically effective amount is usually in the range of about 0.01 mg to 20 mg, preferably about 0.1 mg to 5 mg, per day per kg bodyweight for humans. Depending upon the pathologic condition to be treated, the severity of infection, and the patient's condition, the said therapeutically effective amount may be divided into several sub-units per day or may be administered at more than one day intervals. The patient to be treated may be any warm-blooded animal, preferably a mammal, more preferably a human being, suffering from said viral infection or associated pathologic condition.

The preferred di-, tri- or tetra-substituted pyrido(3,2-d) pyrimidine derivatives of the present invention are non-sedating. In other words, a dose of such compounds that is twice the minimum dose sufficient to provide analgesia in an animal model for determining pain relief causes only transient (i.e. lasting for no more than half the time that pain relief lasts) or preferably no statistically significant sedation in an animal model assay of sedation (using the method described by Fitzgerald et al. in *Toxicology* (1988) 49:433-9). Preferably, a dose that is five times the minimum dose sufficient to provide analgesia does not produce statistically significant sedation. More preferably, a compound provided herein does not produce sedation at intravenous doses of less than 10 mg/kg per day or at oral doses of less than 30 mg/kg per day.

If desired, di-, tri- or tetra-substituted pyrido(3,2-d)pyrimidine derivatives provided herein may be evaluated for toxicity (a preferred compound is non-toxic when an anti-viral amount is administered to a patient) and/or side effects (a preferred compound produces side effects comparable to placebo when a therapeutically effective amount of the compound is administered to a patient). Toxicity and side effects may be assessed by using any standard method known in the art. In general, the term "non-toxic" as used herein shall be understood as referring to any substance that, in keeping with established criteria, is susceptible to approval by the United States Federal Drug Administration for administration to mammals, preferably human beings.

Toxicity may be also evaluated using assays including bacterial reverse mutation assays, such as an Ames test, as well as standard teratogenicity and tumorogenicity assays. Preferably, administration of di-, tri- or tetra-substituted pyrido(3,2-d)pyrimidine derivatives provided herein within the therapeutic dose ranges disclosed hereinabove does not result in prolongation of heart QT intervals (e.g. as determined by electrocardiography in guinea pigs, minipigs or dogs). When administered daily, such doses also do not cause liver enlargement resulting in an increase of liver to body weight ratio of more than 50% over matched controls in laboratory rodents (e.g. mice or rats). Such doses also preferably do not cause liver enlargement resulting in an increase of liver to body weight ratio of more than 10% over matched untreated controls in dogs or other non-rodent mammals. The preferred di-, tri- or tetra-substituted pyrido(3,2-d)pyrimidine derivatives of the present invention also do not promote substantial release of liver enzymes from hepatocytes in vivo, i.e. the therapeutic doses do not elevate serum levels of such enzymes by more than 50% over matched untreated controls in vivo in laboratory rodents.

Another embodiment of this invention includes the various precursor or "pro-drug" forms of the di-, tri- or tetra-substituted pyrido(3,2-d)pyrimidine derivatives of the present invention. It may be desirable to formulate the compounds of the present invention in the form of a chemical species which itself is not significantly biologically active, but which when delivered to the body of a human being or higher mammal will undergo a chemical reaction catalyzed by the normal function of the body, inter alia, enzymes present in the stomach or in blood serum, said chemical reaction having the effect of releasing a compound as defined herein. The term "pro-drug" thus relates to these species which are converted in vivo into the active pharmaceutical ingredient.

The pro-drugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used.

For the purposes of the present invention the term "therapeutically suitable pro-drug" is defined herein as a compound modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome.

The present invention will be further described with reference to certain more specific embodiments and examples, but the present invention is not limited thereto, but only by the attached claims. The following examples are given by way of illustration only. HPLC methods referred to below are as follows:

Method A
Column: Phenomenex Synergi 4μ C18 Hydro RP
Dimensions: 30×4.6 mm
Mobile Phase: A) Water with 0.1% Formic Acid
   B) Acetonitrile with 0.1% Formic Acid
Gradient: A/B (95:5) to B (100%) in 5 minutes
Flow Rate: 2 ml/minute
Temperature: 30° C.
Detection: UV at 254 nm
Method B
Column: Phenomenex Gemini 5μ C18
Dimensions: 30×4.6 mm
Mobile Phase: A) Water with 0.1% Formic Acid
   B) Acetonitrile with 0.1% Formic Acid
Gradient: A/B (95:5) to B (100%) in 3 minutes
Flow Rate: 2 ml/minute
Temperature: 30° C.
Detection: UV at 254 nm Example 1

Synthesis of 6-chloro-4-[1,2,4]triazol-1-yl-pyrido[3,2-d]pyrimidin-2-yl-amine

A solution of 1,2,4-triazole (1.4 g, 20 mmol) and phosphorus oxychloride (1.4 mL, 15 mmol) in dry acetonitrile (40 mL) was adder to a stirred suspension of 2-amino-6-chloro-3H-pyrido[3,2-d]pyrimidin-4-one (1 g, 5 mmol) and N-N-diisopropyl-ethyl-amine (DIEA; 4.4 ml, 25 mmol) in dry acetonitrile (30 ml). The mixture was stirred at room temperature for 24 hours. 2 molar equivalents of 1,2,4-triazole (0.7 g, 10 mmol), 1.5 equivalent of phosphorus oxychloride (0.7 ml, 7.5 mmol) and 2.5 equivalents of DIEA (2.2 ml, 12.5 mmol) were added to the mixture. After stirring at room temperature for 48 hours, the same amount of the above reagents was added again. The reaction mixture was stirred for 7 full days and the yellow precipitate was filtered off, washed successively with acetonitrile, DCM and ether. The solid was dried under vacuum, providing the pure title compound as a yellow solid (667 mg, yield 53%) which was characterised as follows: MS (m/z) 248.8 [M+H]$^+$.

Example 2

Synthesis of 6-(4-fluorophenyl)-4-n-propyl-pyrido[3,2-d]pyrimidin-2-yl-amine

The following scheme shows the sequence of reactions:

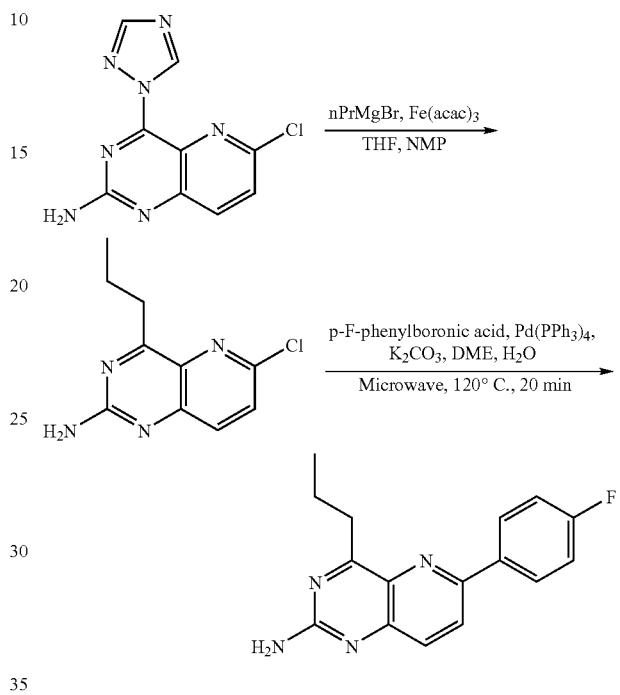

To a suspension of the intermediate of example 1 (0.47 g, 1.9 mmol) and iron tris(acetylacetonate) (34 mg, 0.095 mmol) in tetrahydrofuran (50 ml, hereinafter THF) and N-methylpyrrolidone (20 ml, hereinafter NMP) was added n-propylmagnesium bromide (1.9 ml, 3.8 mmol as a 2.0 M solution in THF). After stirring at room temperature for 40 minutes, the solution was diluted with THF and then quenched by adding a solution of 1N HCl. The mixture was extracted with ethyl acetate (150 ml), then dried over Na$_2$SO$_4$ and concentrated to afford 6-chloro-4-n-propyl-pyrido[3,2-d]pyrimidin-2-ylamine as a brown solid (0.32 g), which was used in the next step without purification. Its mass spectrum data was as follows: MS (m/z) 223.1 [M+H]$^+$.

A mixture of crude 6-chloro-4-n-propyl-pyrido[3,2-d]pyrimidin-2-ylamine (320 mg, 1.4 mmol), potassium carbonate (387 mg, 2.8 mmol), tetrakis-(triphenylphosphine) palladium (49 mg) and 4-fluorophenylboronic acid (160 mg, 1.12 mmol) in dimethylether (9 ml) and water (3 ml) was heated to 110° C. for 20 minutes under microwave irradiation. Solvents were concentrated in vacuo and the residue was purified by high performance liquid chromatography (hereinafter referred as HPLC) using a C18 column with a gradient of H$_2$O and acetonitrile, to provide the title compound as a white solid (80 mg, yield: 15% over the sequence of 2 steps) which was characterised by mass spectrum, HPLC and proton nuclear magnetic resonance as follows:

MS (m/z): 283.0 [M+H]$^+$;

HPLC R$_t$=4.01 minutes (Method A).

$^1$H-NMR (300 MHz, DMSO-$d_6$): peaks at 0.94 (t, 3H), 1.81 (m, 2H), 3.22 (t, 2H), 6.93 (bs, 2H), 7.31 (dd, 2H), 7.80 (d, 1H), and 8.16-8.22 (m, 3H) ppm.

Example 3

Synthesis of N-[4-(2-amino-4-n-propyl-pyrido[3,2-d]pyrimidin-6-yl)-phenyl]-acetamide

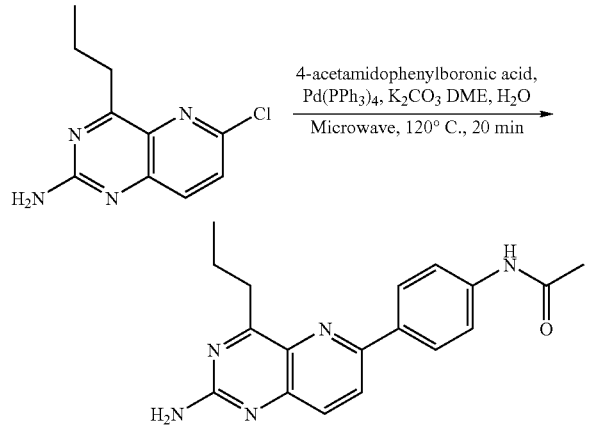

As indicated in the above scheme, the procedure of example 2 was repeated, except for the use of 4-acetamidophenylboronic acid instead of 4-fluorophenylboronic acid. The resulting compound was characterised by its mass spectrum and HPLC as follows: MS (m/z) 321.9 [M+H]$^+$; HPLC $R_t$=2.85 minutes (Method A).

Example 4

Synthesis of 6-(4-fluorophenyl)-4-n-propyl-pyrido[3,2-d]pyrimidine

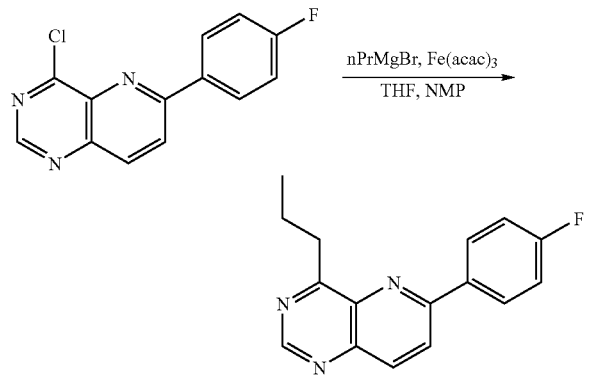

The procedure of example 2 was repeated, except for the use of 4-chloro-6-(4-fluorophenyl)-pyrido[3,2-d]pyrimidine (the synthesis of which has been disclosed in WO2006/135993) instead of 6-chloro-4-[1,2,4]triazol-1-yl-pyrido[3,2-d]pyrimidin-2-yl-amine as a starting material. The resulting compound was characterised by its mass spectrum as follows: MS (m/z) 268.0 [M+H]$^+$; HPLC $R_t$=5.13 minutes (Method A).

Example 5

Synthesis of 4-ethyl-6-(4-fluoro-phenyl)-pyrido[3,2-d]pyrimidin-2-ylamine

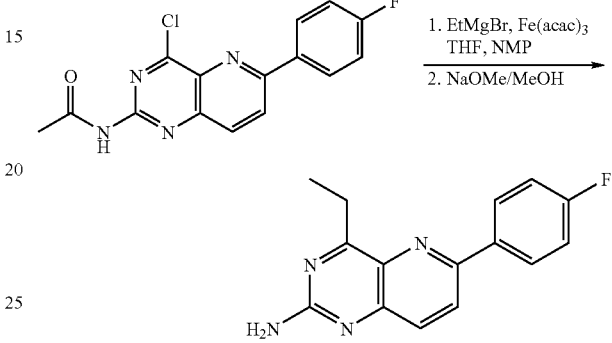

A mixture of N-[4-chloro-6-(4-fluoro-phenyl)-pyrido[3,2-d]pyrimidin-2-yl]-acetamide (63 mg, 0.2 mmol; the synthesis of which has been disclosed in WO 2006/135993) and iron tris(acetylacetonate) (10 mg, 0.028 mmol) in THF (2 ml) and NMP (1 ml) was added ethylmagnesium bromide (0.6 ml, 0.6 mmol; 1.0 M solution in THF). After stirring at room temperature for 10 minutes, the solution was diluted with THF and quenched by adding a solution of 0.2 N HCl. The mixture was extracted with ethyl acetate, then dried over $Na_2SO_4$ and concentrated. The residue was dissolved in methanol (1 ml) and then sodium methoxide (0.2 ml; 0.5 N solution in methanol) was added. The mixture was heated to 120° C. for 10 minutes under microwave irradiation. Solvents were concentrated in vacuo and the residue was purified by HPLC using a C18 column with a gradient of $H_2O$ and 0.1% TFA-acetonitrile, to provide the pure title compound as a white solid (1 mg, yield: 2%) which was characterised by its mass spectrum as follows: MS (m/z) 269.0 [M+H]$^+$; HPLC $R_t$=4.14 minutes (Method A).

Example 6

Synthesis of 6-(4-fluorophenyl)-4-isobutyl-pyrido[3,2-d]pyrimidin-2-ylamine

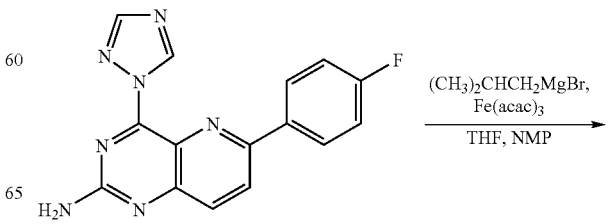

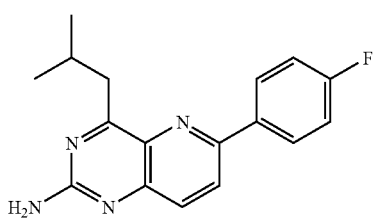

To a solution of 6-(4-fluorophenyl)-4-[1,2,4]triazol-1-yl-pyrido[3,2-d]pyrimidin-2-ylamine (0.15 g, 0.49 mmol; obtained from the 2-acetamido analogue described as example 155 of WO 2006/135993 through non-basic, e.g. acidic, cleavage of the N-acetyl group according to methods known to the skilled person) and iron tris(acetylacetonate) (17 mg, 0.048 mmol) in THF (15 ml) and NMP (15 ml) was added isobutylmagnesium bromide (1.0 ml, 0.5 mmol; 2.0 M solution in ether). After stirring at room temperature for 20 minutes, the solution was diluted with THF and quenched by adding a solution of 1N HCl. The mixture was extracted with ethyl acetate (80 ml), and then dried over $Na_2SO_4$. Solvents were concentrated in vacuo and the residue was purified by HPLC using a C18 column with a gradient of $H_2O$ and 0.1% TFA-acetonitrile, to provide pure the title compound as a white solid (32 mg, yield: 22%) which was characterised by its mass spectrum as follows: MS (m/z) 297.1 $[M+H]^+$; HPLC $R_t$=5.01 minutes (Method A).

Example 7

Synthesis of 4-but-3-enyl-6-(4-fluorophenyl)-pyrido[3,2-d]pyrimidin-2-ylamine

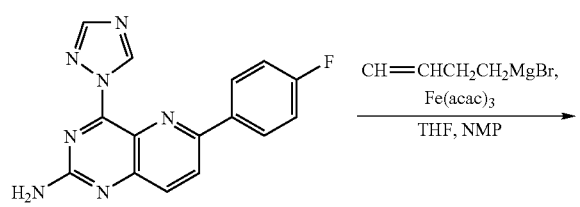

The procedure of example 6 was repeated, except for the use of 3-butenylmagnesium bromide instead of isobutylmagnesium bromide. The resulting pure title compound was characterized as follows: MS (m/z) 295.0 $[M+H]^+$; HPLC $R_t$=4.79 minutes (Method A).

Example 8

Synthesis of 1-[4-(2-amino-4-ethyl-pyrido[3,2-d]pyrimidin-6-yl)-phenyl]-pyrrolidin-2-one

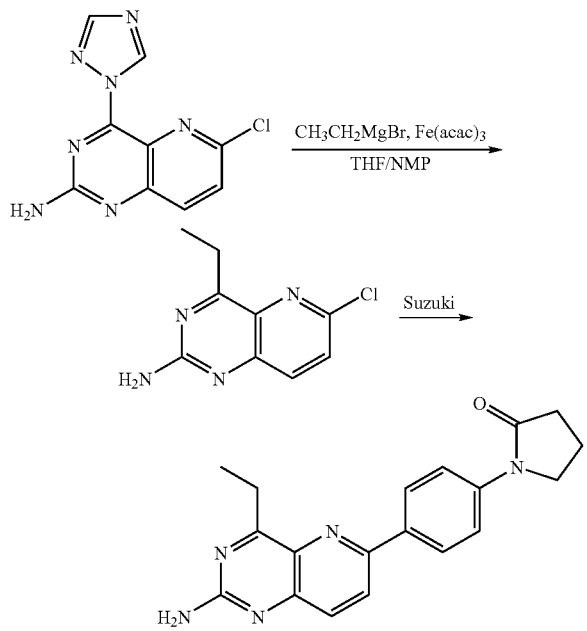

The experimental procedure of example 2 was repeated, except for the use of ethylmagnesium bromide instead of n-propylmagnesium bromide and 1-[4-(4,4,5,5-tetramethyl-[1,3,2]dioxaborolan-2-yl)-phenyl]-pyrrolidin-2-one instead of 4-fluoro-phenylboronic acid. The resulting title compound was characterised as follows: MS (m/z) 334.2 $[M+H]^+$; HPLC $R_t$=2.64 minutes (Method A).

Example 9

Synthesis of 6-(5-Amino-pyrazin-2-yl)-4-ethyl-pyrido[3,2-d]pyrimidin-2-ylamine

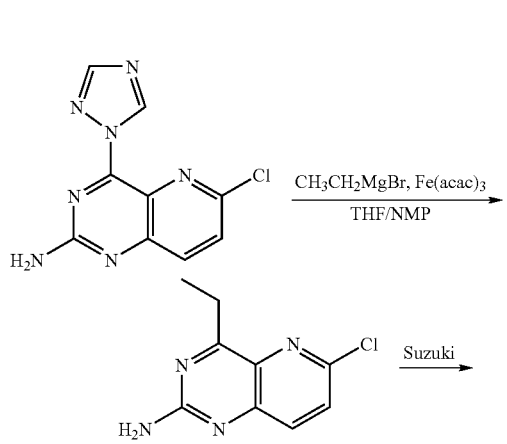

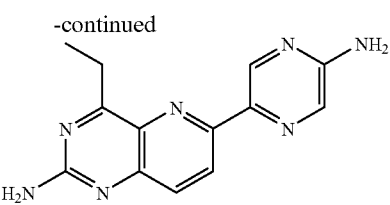

The experimental procedure of example 2 was repeated, except for the use of ethylmagnesium bromide instead of n-propylmagnesium bromide and 5-(4,4,5,5-Tetramethyl-[1,3,2]dioxaborolan-2-yl)-pyrazin-2-ylamine instead of 4-fluorophenylboronic acid. The resulting title compound was characterised as follows: MS (m/z) 268.1 [M+H]$^+$; HPLC R$_t$=1.88 minutes (Method B).

Example 10

Synthesis of 4-(2-[1,3]dioxan-2-yl-ethyl)-6-(4-fluoro-phenyl)-pyrido[3,2-d]pyrimidin-2-ylamine

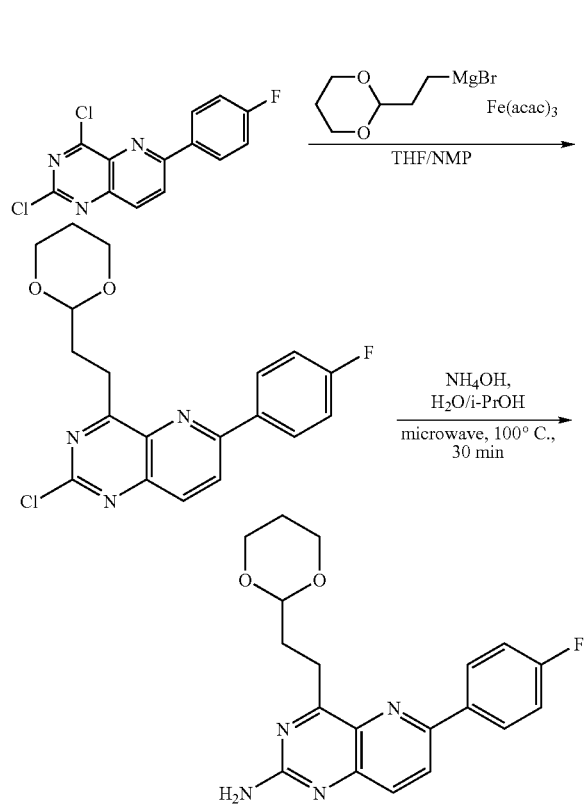

2-chloro-4-(2-[1,3]dioxan-2-yl-ethyl)-6-(4-fluorophenyl)-pyrido[3,2-d]pyrimidine The procedure for the synthesis of 4-ethyl-6-(4-fluorophenyl)-pyrido[3,2-d]pyrimidin-2-ylamine was repeated, except for the use of (1,3-dioxan-2-ylethyl)magnesium bromide instead of ethylmagnesium bromide and 2,4-Dichloro-6-(4-fluoro-phenyl)-pyrido[3,2-d]pyrimidine (see WO2006135993) instead of N-[4-chloro-6-(4-fluoro-phenyl)-pyrido[3,2-d]pyrimidin-2-yl]-acetamide. The resulting title compound was characterised as follows: MS (m/z) 374.0 [M+H]$^+$; HPLC R$_t$=4.46 minutes (Method A).

4-(2-[1,3]dioxan-2-yl-ethyl)-6-(4-fluoro-phenyl)-pyrido[3,2-d]pyrimidin-2-ylamine A suspension of 2-chloro-4-(2-[1,3]dioxan-2-yl-ethyl)-6-(4-fluorophenyl)-pyrido[3,2-d]pyrimidine (9 mg, 0.024 mmol) in iPrOH (0.5 mL) and 30% ammonium hydroxide (4 mL) was heated at 100° C. for 30 minutes. Solvents were concentrated in vacuo and the residue was purified by RP HPLC using a C18 column with a gradient of H$_2$O and 0.1% TFA-acetonitrile, to provide the title compound as a white solid (6 mg, yield: 70%). The resulting title compound was characterised as follows: MS (m/z) 355.0 [M+H]$^+$; HPLC R$_t$=3.34 minutes (Method A).

Example 11

Synthesis of 4-methyl-6-(4-fluorophenyl)-pyrido[3,2-d]pyrimidin-2-ylamine

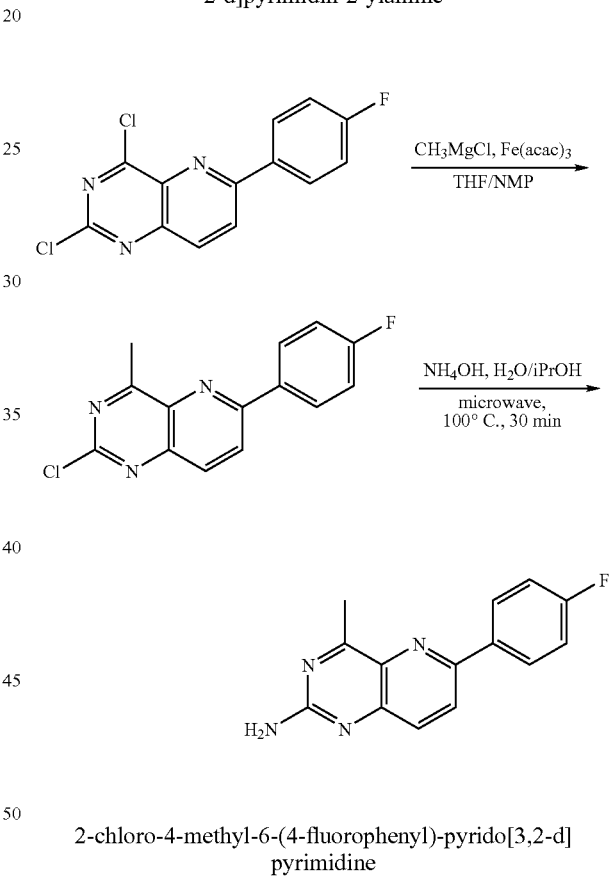

2-chloro-4-methyl-6-(4-fluorophenyl)-pyrido[3,2-d]pyrimidine

The experimental procedure of example 5 was repeated, except for the use of methylmagnesium chloride instead of ethylmagnesium bromide and 2,4-dichloro-6-(4-fluorophenyl)-pyrido[3,2-d]pyrimidine instead of N-[4-chloro-6-(4-fluoro-phenyl)-pyrido[3,2-d]pyrimidin-2-yl]-acetamide.

4-methyl-6-(4-fluorophenyl)-pyrido[3,2-d]pyrimidin-2-ylamine

The experimental procedure of example 10 was repeated, except for the use of 2-chloro-4-methyl-6-(4-fluoro-phenyl)-pyrido[3,2-d]pyrimidine instead of 2-chloro-4-(2-[1,3]dioxan-2-yl-ethyl)-6-(4-fluoro-phenyl)-pyrido[3,2-d]pyrimidine The resulting title compound was characterised as follows: MS (m/z) 255.0 [M+H]+; HPLC R$_t$=2.83 minutes (Method A).

Example 12

Synthesis of 6-(4-fluorophenyl)-4-isopropyl-pyrido[3,2-d]pyrimidin-2-ylamine

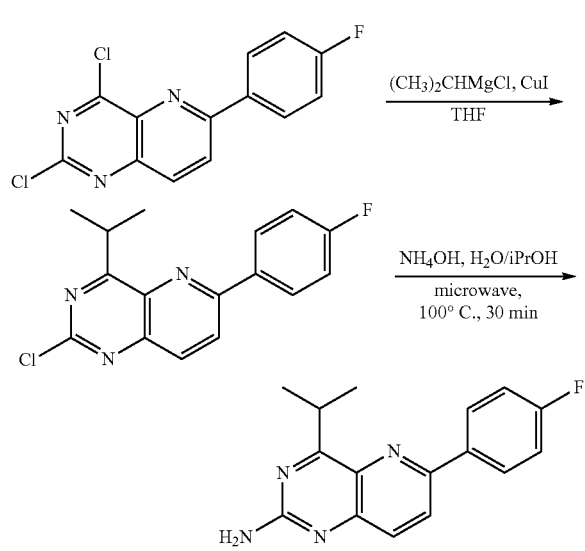

2-chloro-6-(4-fluorophenyl)-4-isopropyl-pyrido[3,2-d]pyrimidine

A mixture of CuI (152 mg, 0.8 mmol) and isopropylmagnesium bromide (1.6 ml, 1.6 mmol; 1.0M in THF) in anhydrous THF (5 ml) was stirred at −78° C. for 30 minutes. To this mixture was added a solution of 2,4-dichloro-6-(4-fluorophenyl)-pyrido[3,2-d]pyrimidine (60 mg, 0.2 mmol) in THF (4 ml). The resulting mixture was stirred at −78° C. for another 2 hours before warming up to room temperature. The reaction was quenched by adding a solution of saturated aqueous ammonium chloride and concentrated ammonia (4:1 ratio; 5 ml). The mixture was extracted with EtOAc and the extracts dried over Na$_2$SO$_4$. Solvents were concentrated in vacuo and the crude residue was used in the next step without further purification. The resulting compound was characterized as follows: MS (m/z) 302.1 [M+H]+; HPLC R$_t$=4.72 minutes (Method A).

6-(4-fluorophenyl)-4-isopropyl-pyrido[3,2-d]pyrimidin-2-ylamine

The procedure for the synthesis of 4-(2-[1,3]dioxan-2-yl-ethyl)-6-(4-fluoro-phenyl)-pyrido[3,2-d]pyrimidin-2-ylamine was repeated, except for the use of 2-chloro-6-(4-fluoro-phenyl)-4-isopropyl-pyrido[3,2-d]pyrimidine instead of 2-chloro-4-(2-[1,3]dioxan-2-yl-ethyl)-6-(4-fluoro-phenyl)-pyrido[3,2-d]pyrimidine. The resulting title compound was characterized as follows: MS (m/z) 283.0 [M+H]+; HPLC R$_t$=3.42 minutes (Method A).

Example 13

Synthesis of 4-Cyclopropyl-6-(4-fluoro-phenyl)-pyrido[3,2-d]pyrimidin-2-ylamine

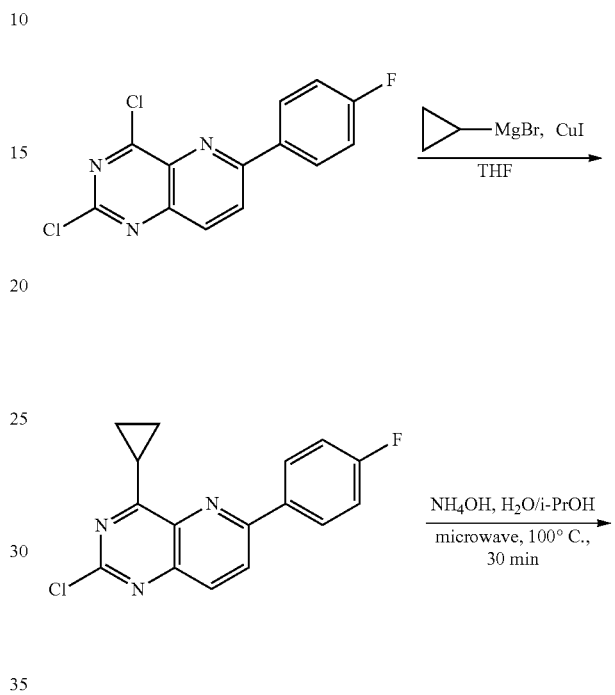

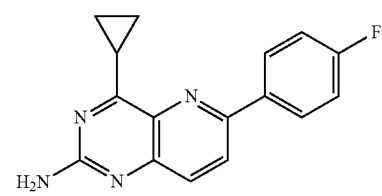

2-chloro-4-cyclopropyl-6-(4-fluorophenyl)-pyrido[3,2-d]pyrimidine

The experimental procedure of example 12 was repeated, except for the use of cyclopropylmagnesium bromide instead of isopropylmagnesium bromide. The resulting compound was characterized as follows: MS (m/z) 300.1 [M+H]+; HPLC R$_t$=4.58 minutes (Method B).

4-cyclopropyl-6-(4-fluorophenyl)-pyrido[3,2-d]pyrimidin-2-ylamine

The procedure for the synthesis of 4-(2-[1,3]dioxan-2-yl-ethyl)-6-(4-fluoro-phenyl)-pyrido[3,2-d]pyrimidin-2-ylamine was repeated, except for the use of 2-chloro-4-cyclopropyl-6-(4-fluoro-phenyl)-pyrido[3,2-d]pyrimidine instead of 2-chloro-4-(2-[1,3]dioxan-2-yl-ethyl)-6-(4-fluoro-phenyl)-pyrido[3,2-d]pyrimidine. The compound was characterized as follows: MS (m/z) 281.0 [M+H]$^+$; HPLC R$_t$=2.96 minutes (Method A).

Example 14

Synthesis of 1-[4-(2-amino-4-cyclopropyl-pyrido[3,2-d]pyrimidin-6-yl)-phenyl]-pyrrolidin-2-one

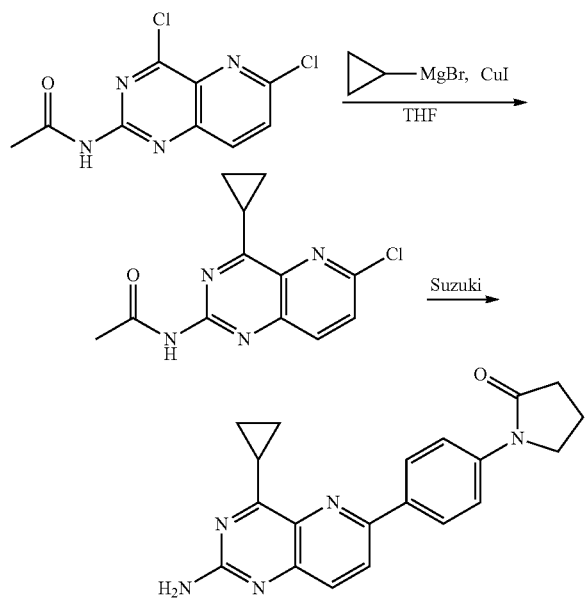

N-(6-chloro-4-cyclopropyl-pyrido[3,2-d]pyrimidin-2-yl)-acetamide

The experimental procedure of example 12 was repeated, except for the use of N-(4,6-dichloro-pyrido[3,2-d]pyrimidin-2-yl)-acetamide (a compound described in WO 2006/135993) instead of 2,4-dichloro-6-(4-fluoro-phenyl)-pyrido[3,2-d]pyrimidine. The resulting compound was characterized as follows: MS (m/z) 263.0 [M+H]$^+$; HPLC R$_t$=2.24 minutes (Method B).

1-[4-(2-amino-4-cyclopropyl-pyrido[3,2-d]pyrimidin-6-yl)-phenyl]-pyrrolidin-2-one The experimental procedure of example 2 was repeated, except for the use of 1-[4-(4,4,5,5-tetramethyl-[1,3,2]dioxaborolan-2-yl)-phenyl]-pyrrolidin-2-one instead of 4-fluorophenylboronic acid and N-(6-chloro-4-cyclopropyl-pyrido[3,2-d]pyrimidin-2-yl)-acetamide instead of 6-chloro-4-propyl-pyrido[3,2-d]pyrimidin-2-ylamine. The resulting compound was characterized as follows: MS (m/z) 346.2 [M+H]$^+$; HPLC R$_t$=2.67 minutes (Method B).

Example 15

Anti-HCV Assay/Replicon Assay

The anti-HCV activity of certain pyrido[3,2-d]pyrimidine derivatives of this invention was tested in a human hepatoma Huh-7 cell line harbouring a HCV replicon. The assay comprised the following steps:

Step 1: Compound Preparation and Serial Dilution
1. for water soluble pyrido[3,2-d]pyrimidine derivatives, a volume of 500 µL of solution in cell media (DMEM, 10% FBS, P/S, L-Glutamine) was prepared with a concentration being twice the concentration of the starting final serial dilution concentration. A volume of 150 µL of the solution was added to the pre-specified wells in column 1 of a 96-well cell culture plate (PerkinElmer, white plate, cat. #6005181, for EC$_{50}$ assay; black plate, cat. #6005182 for CC$_{50}$ assay). The rest of the plate, columns 2-12, was filled with 100 µL of cell media. The plate was then placed on a Precision 2000 Workstation to start the serial dilution. Compounds were diluted three times each step from column 1 to column 10. Column 11 was used as a blank control (no compound added).
2. for pyrido[3,2-d]pyrimidine derivatives requiring DMSO to dissolve, serial dilution is performed in 50% DMSO in a 384-well plate. A solution containing a compound at 100-fold concentration of the starting final serial dilution concentration was prepared in 50% DMSO and added to the pre-specified wells in column 1 of a polypropylene 384-well plate. The plate was then placed on a Precision 2000 Workstation to start the serial dilution. After the serial dilution, a volume of 2 µL of the solution was transferred from the 384-well plate to a 96-well cell culture plate containing 100 µL of cell media on a Biomek FX Workstation. The DMSO concentration in the final assay condition was 0.5% after cells are added to the plate and the total volume in each well is brought to 200 µL.

Step 2: to each well of the serial dilution plate prepared above, 100 µL of cell media containing 6000 suspended Huh-7 HCV replicon cells was added with a Multidrop workstation. The plates were incubated for 3 days at 37° C. with 5% CO$_2$.

Step 3: Detection:
a) for the EC$_{50}$ assay, the media in a 96-well cell culture plate was aspirated with a Biotek EL405 plate-washer. A volume of 200 µL of a solution containing a 1:1 mixture of cell-lysis buffer (Promega, Luciferase Cell Culture Lysis 5× Reagent, cat. #E1531) and luciferase substrate solution (Promega, Luciferase Assay, cat. # E4550) was added to each well of the plate with Multidrop. The plate was incubated for 30 minutes at room temperature before the luminescence signal was measured with a TopCount plate-reader.
b) for the CC$_{50}$ assay, a volume of 100 µL of pre-mixed CellTiter-Glo (Promega, cat. # G7572) solution is added directly to the cell culture in each well of the plate and the luminescence signal is measured with a TopCount plate-reader after 10 minutes of incubation at room temperature.

The table below shows EC$_{50}$ and CC$_{50}$ values (expressed in nM and µM respectively, i.e. nmol/l and pmol/l) of a few pyrido[3,2-d]pyrimidine derivatives tested in this assay. Results in the table below are expressed by the following data:
the 50% cytostatic concentration (CC$_{50}$). i.e. the concentration that results in 50% inhibition of cell growth, and
the 50% effective concentration (EC$_{50}$), i.e. the concentration that protects 50% of the cell monolayer from virus-induced cythopathic effect.

TABLE

| Example | EC$_{50}$<br>(A < 300 nM; B 300-1,000 nM;<br>C > 1,000 nM) | CC$_{50}$<br>(A < 10 µM; B 10-20 µM;<br>C > 20 µM) |
| --- | --- | --- |
| 2 | A | C |
| 3 | B | C |

TABLE-continued

| Example | EC$_{50}$ (A < 300 nM; B 300-1,000 nM; C > 1,000 nM) | CC$_{50}$ (A < 10 µM; B 10-20 µM; C > 20 µM) |
| --- | --- | --- |
| 5 | A | A |
| 6 | A | C |
| 7 | A | C |
| 8 | A | C |
| 9 | B | A |
| 10 | B | C |
| 11 | A | A |
| 12 | A | C |
| 13 | A | B |
| 14 | A | B |

Examples 16 to 85

Synthesis of 6-(4-fluorophenyl)-4-n-propyl-pyrido[3,2-d]pyrimidine analogues

The experimental procedure of example 4 is repeated, except for the use of a different organomagnesium halide. In this way, the following compounds are obtained in similar yields:

6-(4-fluorophenyl)-4-methyl-pyrido[3,2-d]pyrimidine,
6-(4-fluorophenyl)-4-ethyl-pyrido[3,2-d]pyrimidine,
6-(4-fluorophenyl)-4-isopropyl-pyrido[3,2-d]pyrimidine,
6-(4-fluorophenyl)-4-isobutyl-pyrido[3,2-d]pyrimidine,
6-(4-fluorophenyl)-4-pentyl-pyrido[3,2-d]pyrimidine,
6-(4-fluorophenyl)-4-tert-butyl-pyrido[3,2-d]pyrimidine,
6-(4-fluorophenyl)-4-hexyl-pyrido[3,2-d]pyrimidine,
6-(4-fluorophenyl)-4-heptyl-pyrido[3,2-d]pyrimidine,
6-(4-fluorophenyl)-4-octyl-pyrido[3,2-d]pyrimidine,
6-(4-fluorophenyl)-4-decyl-pyrido[3,2-d]pyrimidine,
6-(4-fluorophenyl)-4-allyl-pyrido[3,2-d]pyrimidine,
6-(4-fluorophenyl)-4-ethynyl-pyrido[3,2-d]pyrimidine,
6-(4-fluorophenyl)-4-phenyl-pyrido[3,2-d]pyrimidine,
6-(4-fluorophenyl)-4-(4-methoxyphenyl)-pyrido[3,2-d]pyrimidine,
6-(4-fluorophenyl)-4-(4-chlorophenyl)-pyrido[3,2-d]pyrimidine,
6-(4-fluorophenyl)-4-(4-fluorophenyl)-pyrido[3,2-d]pyrimidine,
6-(4-fluorophenyl)-4-(4-methylphenyl)-pyrido[3,2-d]pyrimidine,
6-(4-fluorophenyl)-4-(3-methylphenyl)-pyrido[3,2-d]pyrimidine,
6-(4-fluorophenyl)-4-(2-methylphenyl)-pyrido[3,2-d]pyrimidine,
6-(4-fluorophenyl)-4-vinyl-pyrido[3,2-d]pyrimidine,
6-(4-fluorophenyl)-4-cyclohexyl-pyrido[3,2-d]pyrimidine,
6-(4-fluorophenyl)-4-cyclopentyl-pyrido[3,2-d]pyrimidine,
6-(4-fluorophenyl)-4-cyclopropyl-pyrido[3,2-d]pyrimidine,
6-(4-fluorophenyl)-4-(4-but-3-enyl)-pyrido[3,2-d]pyrimidine,
6-(4-fluorophenyl)-4-(pyrid-2-yl)-pyrido[3,2-d]pyrimidine,
6-(4-fluorophenyl)-4-(1,3-dioxan-2-ylmethyl)-pyrido[3,2-d]pyrimidine,
6-(4-fluorophenyl)-4-benzyl-pyrido[3,2-d]pyrimidine,
6-(4-fluorophenyl)-4-(thien-3-yl)-pyrido[3,2-d]pyrimidine,
6-(4-fluorophenyl)-4-(naphth-1-yl)-pyrido[3,2-d]pyrimidine,
6-(4-fluorophenyl)-4-(naphth-2-yl)-pyrido[3,2-d]pyrimidine,
6-(4-fluorophenyl)-4-(4-methylbenzyl)-pyrido[3,2-d]pyrimidine,
6-(4-fluorophenyl)-4-(3-methylbenzyl)-pyrido[3,2-d]pyrimidine,
6-(4-fluorophenyl)-4-(2-methylbenzyl)-pyrido[3,2-d]pyrimidine,
6-(4-fluorophenyl)-4-(4-methoxybenzyl)-pyrido[3,2-d]pyrimidine,
6-(4-fluorophenyl)-4-(3-methoxybenzyl)-pyrido[3,2-d]pyrimidine,
6-(4-fluorophenyl)-4-(2-methoxybenzyl)-pyrido[3,2-d]pyrimidine,
6-(4-fluorophenyl)-4-(4-chlorobenzyl)-pyrido[3,2-d]pyrimidine,
6-(4-fluorophenyl)-4-(3-chlorobenzyl)-pyrido[3,2-d]pyrimidine,
6-(4-fluorophenyl)-4-(2-chlorobenzyl)-pyrido[3,2-d]pyrimidine,
6-(4-fluorophenyl)-4-(4-fluorobenzyl)-pyrido[3,2-d]pyrimidine,
6-(4-fluorophenyl)-4-(3-fluorobenzyl)-pyrido[3,2-d]pyrimidine,
6-(4-fluorophenyl)-4-(2-fluorobenzyl)-pyrido[3,2-d]pyrimidine,
6-(4-fluorophenyl)-4-(4-bromobenzyl)-pyrido[3,2-d]pyrimidine,
6-(4-fluorophenyl)-4-(3-bromobenzyl)-pyrido[3,2-d]pyrimidine,
6-(4-fluorophenyl)-4-(2-bromobenzyl)-pyrido[3,2-d]pyrimidine,
6-(4-fluorophenyl)-4-(2-biphenyl)-pyrido[3,2-d]pyrimidine,
6-(4-fluorophenyl)-4-(4-biphenyl)-pyrido[3,2-d]pyrimidine,
6-(4-fluorophenyl)-4-(3-fluoro-4-biphenyl)-pyrido[3,2-d]pyrimidine,
6-(4-fluorophenyl)-4-(3,4-dichlorophenyl)-pyrido[3,2-d]pyrimidine,
6-(4-fluorophenyl)-4-(3,5-dichlorophenyl)-pyrido[3,2-d]pyrimidine,
6-(4-fluorophenyl)-4-(3,4-difluorophenyl)-pyrido[3,2-d]pyrimidine,
6-(4-fluorophenyl)-4-(3,5-difluorophenyl)-pyrido[3,2-d]pyrimidine,
6-(4-fluorophenyl)-4-(3-chloro-4-fluorophenyl)-pyrido[3,2-d]pyrimidine,
6-(4-fluorophenyl)-4-(3-chloro-5-fluorophenyl)-pyrido[3,2-d]pyrimidine,
6-(4-fluorophenyl)-4-(4-chloro-3-fluorophenyl)-pyrido[3,2-d]pyrimidine,
6-(4-fluorophenyl)-4-(3,5-dimethylphenyl)-pyrido[3,2-d]pyrimidine,
6-(4-fluorophenyl)-4-(3,4-dimethylphenyl)-pyrido[3,2-d]pyrimidine,
6-(4-fluorophenyl)-4-(2,3-dimethylphenyl)-pyrido[3,2-d]pyrimidine,
6-(4-fluorophenyl)-4-(2,4-dimethylphenyl)-pyrido[3,2-d]pyrimidine,
6-(4-fluorophenyl)-4-(2,5-dimethylphenyl)-pyrido[3,2-d]pyrimidine,
6-(4-fluorophenyl)-4-(2,6-dimethylphenyl)-pyrido[3,2-d]pyrimidine,
6-(4-fluorophenyl)-4-(2,4-dimethoxyphenyl)-pyrido[3,2-d]pyrimidine,
6-(4-fluorophenyl)-4-(2,5-dimethoxyphenyl)-pyrido[3,2-d]pyrimidine,
6-(4-fluorophenyl)-4-(3,4-dimethoxyphenyl)-pyrido[3,2-d]pyrimidine,
6-(4-fluorophenyl)-4-(3,5-dimethoxyphenyl)-pyrido[3,2-d]pyrimidine, 6-(4-fluorophenyl)-4-(3,4,5-trimethoxyphenyl)-pyrido[3,2-d]pyrimidine,
6-(4-fluorophenyl)-4-(2,4,5-trimethylphenyl)-pyrido[3,2-d]pyrimidine,
6-(4-fluorophenyl)-4-(2,4,6-trimethylphenyl)-pyrido[3,2-d]pyrimidine,
6-(4-fluorophenyl)-4-(4-ethylphenyl)-pyrido[3,2-d]pyrimidine, and
6-(4-fluorophenyl)-4-(4-ethoxyphenyl)-pyrido[3,2-d]pyrimidine.

Examples 86 to 225

Synthesis of 6-(4-fluorophenyl)-4-n-propyl-pyrido[3,2-d]pyrimidine analogues

The two-steps experimental procedure of example 2 is repeated, except for the use of a different organomagnesium halide in the first step. In this way, the following intermediate compounds (examples 86 to 155) are obtained:
6-chloro-4-methyl-pyrido[3,2-d]pyrimidin-2-ylamine,
6-chloro-4-ethyl-pyrido[3,2-d]pyrimidin-2-ylamine,
6-chloro-4-isopropyl-pyrido[3,2-d]pyrimidin-2-ylamine,
6-chloro-4-isobutyl-pyrido[3,2-d]pyrimidin-2-ylamine,
6-chloro-4-pentyl-pyrido[3,2-d]pyrimidin-2-ylamine,
6-chloro-4-tert-butyl-pyrido[3,2-d]pyrimidin-2-ylamine,
6-chloro-4-hexyl-pyrido[3,2-d]pyrimidin-2-ylamine,
6-chloro-4-heptyl-pyrido[3,2-d]pyrimidin-2-ylamine,
6-chloro-4-octyl-pyrido[3,2-d]pyrimidin-2-ylamine,
6-chloro-4-decyl-pyrido[3,2-d]pyrimidin-2-ylamine,
6-chloro-4-allyl-pyrido[3,2-d]pyrimidin-2-ylamine,
6-chloro-4-ethynyl-pyrido[3,2-d]pyrimidin-2-ylamine,
6-chloro-4-phenyl-pyrido[3,2-d]pyrimidin-2-ylamine,
6-chloro-4-(4-methoxyphenyl)-pyrido[3,2-d]pyrimidin-2-ylamine,
6-chloro-4-(4-chlorophenyl)-pyrido[3,2-d]pyrimidin-2-ylamine,
6-chloro-4-(4-fluorophenyl)-pyrido[3,2-d]pyrimidin-2-ylamine,
6-chloro-4-(4-methylphenyl)-pyrido[3,2-d]pyrimidin-2-ylamine,
6-chloro-4-(3-methylphenyl)-pyrido[3,2-d]pyrimidin-2-ylamine,
6-chloro-4-(2-methylphenyl)-pyrido[3,2-d]pyrimidin-2-ylamine,
6-chloro-4-vinyl-pyrido[3,2-d]pyrimidin-2-ylamine,
6-chloro-4-cyclohexyl-pyrido[3,2-d]pyrimidin-2-ylamine,
6-chloro-4-cyclopentyl-pyrido[3,2-d]pyrimidin-2-ylamine,
6-chloro-4-cyclopropyl-pyrido[3,2-d]pyrimidin-2-ylamine,
6-chloro-4-(4-but-3-enyl)-pyrido[3,2-d]pyrimidin-2-ylamine,
6-chloro-4-(pyrid-2-yl)-pyrido[3,2-d]pyrimidin-2-ylamine,
6-chloro-4-(1,3-dioxan-2-ylmethyl)-pyrido[3,2-d]pyrimidin-2-ylamine,
6-chloro-4-benzyl-pyrido[3,2-d]pyrimidin-2-ylamine,
6-chloro-4-(thien-3-yl)-pyrido[3,2-d]pyrimidin-2-ylamine,
6-chloro-4-(naphth-1-yl)-pyrido[3,2-d]pyrimidin-2-ylamine,
6-chloro-4-(naphth-2-yl)-pyrido[3,2-d]pyrimidin-2-ylamine,
6-chloro-4-(4-methylbenzyl)-pyrido[3,2-d]pyrimidin-2-ylamine,
6-chloro-4-(3-methylbenzyl)-pyrido[3,2-d]pyrimidin-2-ylamine,
6-chloro-4-(2-methylbenzyl)-pyrido[3,2-d]pyrimidin-2-ylamine,
6-chloro-4-(4-methoxybenzyl)-pyrido[3,2-d]pyrimidin-2-ylamine,
6-chloro-4-(3-methoxybenzyl)-pyrido[3,2-d]pyrimidin-2-ylamine,
6-chloro-4-(2-methoxybenzyl)-pyrido[3,2-d]pyrimidin-2-ylamine,
6-chloro-4-(4-chlorobenzyl)-pyrido[3,2-d]pyrimidin-2-ylamine,
6-chloro-4-(3-chlorobenzyl)-pyrido[3,2-d]pyrimidin-2-ylamine,
6-chloro-4-(2-chlorobenzyl)-pyrido[3,2-d]pyrimidin-2-ylamine,
6-chloro-4-(4-fluorobenzyl)-pyrido[3,2-d]pyrimidin-2-ylamine,
6-chloro-4-(3-fluorobenzyl)-pyrido[3,2-d]pyrimidin-2-ylamine,
6-chloro-4-(2-fluorobenzyl)-pyrido[3,2-d]pyrimidin-2-ylamine,
6-chloro-4-(4-bromobenzyl)-pyrido[3,2-d]pyrimidin-2-ylamine,
6-chloro-4-(3-bromobenzyl)-pyrido[3,2-d]pyrimidin-2-ylamine,
6-chloro-4-(2-bromobenzyl)-pyrido[3,2-d]pyrimidin-2-ylamine,
6-chloro-4-(2-biphenyl)-pyrido[3,2-d]pyrimidin-2-ylamine,
6-chloro-4-(4-biphenyl)-pyrido[3,2-d]pyrimidin-2-ylamine,
6-chloro-4-(3-fluoro-4-biphenyl)-pyrido[3,2-d]pyrimidin-2-ylamine,
6-chloro-4-(3,4-dichlorophenyl)-pyrido[3,2-d]pyrimidin-2-ylamine,
6-chloro-4-(3,5-dichlorophenyl)-pyrido[3,2-d]pyrimidin-2-ylamine,
6-chloro-4-(3,4-difluorophenyl)-pyrido[3,2-d]pyrimidin-2-ylamine,
6-chloro-4-(3,5-difluorophenyl)-pyrido[3,2-d]pyrimidin-2-ylamine,
6-chloro-4-(3-chloro-4-fluorophenyl)-pyrido[3,2-d]pyrimidin-2-ylamine,
6-chloro-4-(3-chloro-5-fluorophenyl)-pyrido[3,2-d]pyrimidin-2-ylamine,
6-chloro-4-(4-chloro-3-fluorophenyl)-pyrido[3,2-d]pyrimidin-2-ylamine,
6-chloro-4-(3,5-dimethylphenyl)-pyrido[3,2-d]pyrimidin-2-ylamine,
6-chloro-4-(3,4-dimethylphenyl)-pyrido[3,2-d]pyrimidin-2-ylamine,
6-chloro-4-(2,3-dimethylphenyl)-pyrido[3,2-d]pyrimidin-2-ylamine,
6-chloro-4-(2,4-dimethylphenyl)-pyrido[3,2-d]pyrimidin-2-ylamine,
6-chloro-4-(2,5-dimethylphenyl)-pyrido[3,2-d]pyrimidin-2-ylamine,
6-chloro-4-(2,6-dimethylphenyl)-pyrido[3,2-d]pyrimidin-2-ylamine,
6-chloro-4-(2,4-dimethoxyphenyl)-pyrido[3,2-d]pyrimidin-2-ylamine,
6-chloro-4-(2,5-dimethoxyphenyl)-pyrido[3,2-d]pyrimidin-2-ylamine,
6-chloro-4-(3,4-dimethoxyphenyl)-pyrido[3,2-d]pyrimidin-2-ylamine,
6-chloro-4-(3,5-dimethoxyphenyl)-pyrido[3,2-d]pyrimidin-2-ylamine,
6-chloro-4-(3,4,5-trimethoxyphenyl)-pyrido[3,2-d]pyrimidin-2-ylamine,
6-chloro-4-(2,4,5-trimethylphenyl)-pyrido[3,2-d]pyrimidin-2-ylamine, 6-chloro-4-(2,4,6-trimethylphenyl)-pyrido[3,2-d]pyrimidin-2-ylamine,
6-chloro-4-(4-ethylphenyl)-pyrido[3,2-d]pyrimidin-2-ylamine, and
6-chloro-4-(4-ethoxyphenyl)-pyrido[3,2-d]pyrimidin-2-ylamine.

Performance of the second step of the synthetic method then achieves the following final compounds (examples 156 to 225):

6-(4-fluorophenyl)-4-methyl-pyrido[3,2-d]pyrimidin-2-ylamine,
6-(4-fluorophenyl)-4-ethyl-pyrido[3,2-d]pyrimidin-2-ylamine,
6-(4-fluorophenyl)-4-isopropyl-pyrido[3,2-d]pyrimidin-2-ylamine,
6-(4-fluorophenyl)-4-isobutyl-pyrido[3,2-d]pyrimidin-2-ylamine,
6-(4-fluorophenyl)-4-pentyl-pyrido[3,2-d]pyrimidin-2-ylamine,
6-(4-fluorophenyl)-4-tert-butyl-pyrido[3,2-d]pyrimidin-2-ylamine,
6-(4-fluorophenyl)-4-hexyl-pyrido[3,2-d]pyrimidin-2-ylamine,
6-(4-fluorophenyl)-4-heptyl-pyrido[3,2-d]pyrimidin-2-ylamine,
6-(4-fluorophenyl)-4-octyl-pyrido[3,2-d]pyrimidin-2-ylamine,
6-(4-fluorophenyl)-4-decyl-pyrido[3,2-d]pyrimidin-2-ylamine,
6-(4-fluorophenyl)-4-allyl-pyrido[3,2-d]pyrimidin-2-ylamine,
6-(4-fluorophenyl)-4-ethynyl-pyrido[3,2-d]pyrimidin-2-ylamine,
6-(4-fluorophenyl)-4-phenyl-pyrido[3,2-d]pyrimidin-2-ylamine,
6-(4-fluorophenyl)-4-(4-methoxyphenyl)-pyrido[3,2-d]pyrimidin-2-ylamine,
6-(4-fluorophenyl)-4-(4-chlorophenyl)-pyrido[3,2-d]pyrimidin-2-ylamine,
6-(4-fluorophenyl)-4-(4-fluorophenyl)-pyrido[3,2-d]pyrimidin-2-ylamine,
6-(4-fluorophenyl)-4-(4-methylphenyl)-pyrido[3,2-d]pyrimidin-2-ylamine,
6-(4-fluorophenyl)-4-(3-methylphenyl)-pyrido[3,2-d]pyrimidin-2-ylamine,
6-(4-fluorophenyl)-4-(2-methylphenyl)-pyrido[3,2-d]pyrimidin-2-ylamine,
6-(4-fluorophenyl)-4-vinyl-pyrido[3,2-d]pyrimidin-2-ylamine,
6-(4-fluorophenyl)-4-cyclohexyl-pyrido[3,2-d]pyrimidin-2-ylamine,
6-(4-fluorophenyl)-4-cyclopentyl-pyrido[3,2-d]pyrimidin-2-ylamine,
6-(4-fluorophenyl)-4-cyclopropyl-pyrido[3,2-d]pyrimidin-2-ylamine,
6-(4-fluorophenyl)-4-(4-but-3-enyl)-pyrido[3,2-d]pyrimidin-2-ylamine,
6-(4-fluorophenyl)-4-(pyrid-2-yl)-pyrido[3,2-d]pyrimidin-2-ylamine,
6-(4-fluorophenyl)-4-(1,3-dioxan-2-ylmethyl)-pyrido[3,2-d]pyrimidin-2-ylamine,
6-(4-fluorophenyl)-4-benzyl-pyrido[3,2-d]pyrimidin-2-ylamine,
6-(4-fluorophenyl)-4-(thien-3-yl)-pyrido[3,2-d]pyrimidin-2-ylamine,
6-(4-fluorophenyl)-4-(naphth-1-yl)-pyrido[3,2-d]pyrimidin-2-ylamine,
6-(4-fluorophenyl)-4-(naphth-2-yl)-pyrido[3,2-d]pyrimidin-2-ylamine,
6-(4-fluorophenyl)-4-(4-methylbenzyl)-pyrido[3,2-d]pyrimidin-2-ylamine,
6-(4-fluorophenyl)-4-(3-methylbenzyl)-pyrido[3,2-d]pyrimidin-2-ylamine,
6-(4-fluorophenyl)-4-(2-methylbenzyl)-pyrido[3,2-d]pyrimidin-2-ylamine,
6-(4-fluorophenyl)-4-(4-methoxybenzyl)-pyrido[3,2-d]pyrimidin-2-ylamine,
6-(4-fluorophenyl)-4-(3-methoxybenzyl)-pyrido[3,2-d]pyrimidin-2-ylamine,
6-(4-fluorophenyl)-4-(2-methoxybenzyl)-pyrido[3,2-d]pyrimidin-2-ylamine,
6-(4-fluorophenyl)-4-(4-chlorobenzyl)-pyrido[3,2-d]pyrimidin-2-ylamine,
6-(4-fluorophenyl)-4-(3-chlorobenzyl)-pyrido[3,2-d]pyrimidin-2-ylamine,
6-(4-fluorophenyl)-4-(2-chlorobenzyl)-pyrido[3,2-d]pyrimidin-2-ylamine,
6-(4-fluorophenyl)-4-(4-fluorobenzyl)-pyrido[3,2-d]pyrimidin-2-ylamine,
6-(4-fluorophenyl)-4-(3-fluorobenzyl)-pyrido[3,2-d]pyrimidin-2-ylamine,
6-(4-fluorophenyl)-4-(2-fluorobenzyl)-pyrido[3,2-d]pyrimidin-2-ylamine,
6-(4-fluorophenyl)-4-(4-bromobenzyl)-pyrido[3,2-d]pyrimidin-2-ylamine,
6-(4-fluorophenyl)-4-(3-bromobenzyl)-pyrido[3,2-d]pyrimidin-2-ylamine,
6-(4-fluorophenyl)-4-(2-bromobenzyl)-pyrido[3,2-d]pyrimidin-2-ylamine,
6-(4-fluorophenyl)-4-(2-biphenyl)-pyrido[3,2-d]pyrimidin-2-ylamine,
6-(4-fluorophenyl)-4-(4-biphenyl)-pyrido[3,2-d]pyrimidin-2-ylamine,
6-(4-fluorophenyl)-4-(3-fluoro-4-biphenyl)-pyrido[3,2-d]pyrimidin-2-ylamine,
6-(4-fluorophenyl)-4-(3,4-dichlorophenyl)-pyrido[3,2-d]pyrimidin-2-ylamine,
6-(4-fluorophenyl)-4-(3,5-dichlorophenyl)-pyrido[3,2-d]pyrimidin-2-ylamine,
6-(4-fluorophenyl)-4-(3,4-difluorophenyl)-pyrido[3,2-d]pyrimidin-2-ylamine,
6-(4-fluorophenyl)-4-(3,5-difluorophenyl)-pyrido[3,2-d]pyrimidin-2-ylamine,
6-(4-fluorophenyl)-4-(3-chloro-4-fluorophenyl)-pyrido[3,2-d]pyrimidin-2-ylamine,
6-(4-fluorophenyl)-4-(3-chloro-5-fluorophenyl)-pyrido[3,2-d]pyrimidin-2-ylamine,
6-(4-fluorophenyl)-4-(4-chloro-3-fluorophenyl)-pyrido[3,2-d]pyrimidin-2-ylamine,
6-(4-fluorophenyl)-4-(3,5-dimethylphenyl)-pyrido[3,2-d]pyrimidin-2-ylamine,
6-(4-fluorophenyl)-4-(3,4-dimethylphenyl)-pyrido[3,2-d]pyrimidin-2-ylamine,
6-(4-fluorophenyl)-4-(2,3-dimethylphenyl)-pyrido[3,2-d]pyrimidin-2-ylamine,
6-(4-fluorophenyl)-4-(2,4-dimethylphenyl)-pyrido[3,2-d]pyrimidin-2-ylamine,
6-(4-fluorophenyl)-4-(2,5-dimethylphenyl)-pyrido[3,2-d]pyrimidin-2-ylamine,
6-(4-fluorophenyl)-4-(2,6-dimethylphenyl)-pyrido[3,2-d]pyrimidin-2-ylamine,
6-(4-fluorophenyl)-4-(2,4-dimethoxyphenyl)-pyrido[3,2-d]pyrimidin-2-ylamine, 6-(4-fluorophenyl)-4-(2,5-dimethoxyphenyl)-pyrido[3,2-d]pyrimidin-2-ylamine,
6-(4-fluorophenyl)-4-(3,4-dimethoxyphenyl)-pyrido[3,2-d]pyrimidin-2-ylamine,
6-(4-fluorophenyl)-4-(3,5-dimethoxyphenyl)-pyrido[3,2-d]pyrimidin-2-ylamine,
6-(4-fluorophenyl)-4-(3,4,5-trimethoxyphenyl)-pyrido[3,2-d]pyrimidin-2-ylamine,
6-(4-fluorophenyl)-4-(2,4,5-trimethylphenyl)-pyrido[3,2-d]pyrimidin-2-ylamine,
6-(4-fluorophenyl)-4-(2,4,6-trimethylphenyl)-pyrido[3,2-d]pyrimidin-2-ylamine,
6-(4-fluorophenyl)-4-(4-ethylphenyl)-pyrido[3,2-d]pyrimidin-2-ylamine, and
6-(4-fluorophenyl)-4-(4-ethoxyphenyl)-pyrido[3,2-d]pyrimidin-2-ylamine.

Examples 226 to 421

Synthesis of 6-(4-fluorophenyl)-4-n-propyl-pyrido[3,2-d]pyrimidin-2-ylamine analogues The second step of the experimental procedure of example 2 is repeated, except for the use of a different arylboronic acid or heteroarylboronic acid, or a pinacol ester thereof. In this way, the following compounds are obtained in similar yields:
4-n-propyl-6-(4-(4'-allyloxycarbonylpiperazino)phenyl)pyrido[3,2-d]pyrimidin-2-ylamine,
4-n-propyl-6-(3-aminocarbonylphenyl)pyrido[3,2-d]pyrimidin-2-ylamine,
4-n-propyl-6-(4-aminocarbonylphenyl)pyrido[3,2-d]pyrimidin-2-ylamine,
4-n-propyl-6-(2-amino-5-chlorophenyl)pyrido[3,2-d]pyrimidin-2-ylamine,
4-n-propyl-6-(4-amino-3-methoxyphenyl)pyrido[3,2-d]pyrimidin-2-ylamine,
4-n-propyl-6-(2-amino-4-methylphenyl)pyrido[3,2-d]pyrimidin-2-ylamine,
4-n-propyl-6-(2-amino-5-methylphenyl)pyrido[3,2-d]pyrimidin-2-ylamine,
4-n-propyl-6-(4-amino-2-methyl phenyl)pyrido[3,2-d]pyrimidin-2-ylamine,
4-n-propyl-6-(5-amino-2-methyl phenyl)pyrido[3,2-d]pyrimidin-2-ylamine,
4-n-propyl-6-(4-amino-3-nitrophenyl)pyrido[3,2-d]pyrimidin-2-ylamine,
4-n-propyl-6-(2-benzyloxyphenyl)pyrido[3,2-d]pyrimidin-2-ylamine,
4-n-propyl-6-(3-benzyloxy-4-methoxyphenyl)pyrido[3,2-d]pyrimidin-2-ylamine,
4-n-propyl-6-(4-biphenyl)pyrido[3,2-d]pyrimidin-2-ylamine,
4-n-propyl-6-(4-n-butyl phenyl)pyrido[3,2-d]pyrimidin-2-ylamine,
4-n-propyl-6-(4-isobutylphenyl)pyrido[3,2-d]pyrimidin-2-ylamine,
4-n-propyl-6-(4-carboxy-3-fluorophenyl)pyrido[3,2-d]pyrimidin-2-ylamine,
4-n-propyl-6-(3-(3-carboxypropionylamino)phenyl)pyrido[3,2-d]pyrimidin-2-ylamine,
4-n-propyl-6-(4-(3-carboxypropionylamino)phenyl)pyrido[3,2-d]pyrimidin-2-ylamine,
4-n-propyl-6-(3-chloro-4-hydroxy-5-methoxyphenyl)pyrido[3,2-d]pyrimidin-2-ylamine,
4-n-propyl-6-(2-chloro-5-hydroxymethylphenyl)pyrido[3,2-d]pyrimidin-2-ylamine,
4-n-propyl-6-(4-cyanomethoxyphenyl)pyrido[3,2-d]pyrimidin-2-ylamine,
4-n-propyl-6-(3-cyanomethoxyphenyl)pyrido[3,2-d]pyrimidin-2-ylamine,
4-n-propyl-6-(2-cyanomethoxyphenyl)pyrido[3,2-d]pyrimidin-2-ylamine,
4-n-propyl-6-(4-cyanophenyl)pyrido[3,2-d]pyrimidin-2-ylamine,
4-n-propyl-6-(3-cyanophenyl)pyrido[3,2-d]pyrimidin-2-ylamine,
4-n-propyl-6-(2-cyanophenyl)pyrido[3,2-d]pyrimidin-2-ylamine,
4-n-propyl-6-(3-(N-cyclopropylaminocarbonyl)phenyl)pyrido[3,2-d]pyrimidin-2-ylamine,
4-n-propyl-6-(3-(N,N-diethylaminocarbonyl)phenyl)pyrido[3,2-d]pyrimidin-2-ylamine,
4-n-propyl-6-(3-(N,N-dimethylamino)phenyl)pyrido[3,2-d]pyrimidin-2-ylamine,
4-n-propyl-6-(2-(N,N-dimethylamino)phenyl)pyrido[3,2-d]pyrimidin-2-ylamine,
4-n-propyl-6-(3-(N,N-dimethylaminocarbonyl)phenyl)pyrido[3,2-d]pyrimidin-2-ylamine,
4-n-propyl-6-(3-[(N',N'-dimethylamino)ethylaminocarbonyl]phenyl)-pyrido[3,2-d]pyrimidin-2-ylamine,
4-n-propyl-6-(4-[(N',N'-dimethylamino)ethylaminocarbonyl]phenyl)-pyrido[3,2-d]pyrimidin-2-ylamine,
4-n-propyl-6-(3-[1,3]dioxolan-2-ylmethoxyphenyl)pyrido[3,2-d]pyrimidin-2-ylamine,
4-n-propyl-6-(3-(ethoxycarbonyl)methoxyphenyl)pyrido[3,2-d]pyrimidin-2-ylamine,
4-n-propyl-6-(4-(ethoxycarbonyl)methoxyphenyl)pyrido[3,2-d]pyrimidin-2-ylamine,
4-n-propyl-6-(4-ethoxycarbonylphenyl)pyrido[3,2-d]pyrimidin-2-ylamine,
4-n-propyl-6-(3-ethoxycarbonylphenyl)pyrido[3,2-d]pyrimidin-2-ylamine,
4-n-propyl-6-(2-ethoxycarbonylphenyl)pyrido[3,2-d]pyrimidin-2-ylamine,
4-n-propyl-6-(4-(3-ethoxycarbonylpiperidino)carboxamidophenyl)-pyrido[3,2-d]pyrimidin-2-ylamine,
4-n-propyl-6-(4-formylaminophenyl)pyrido[3,2-d]pyrimidin-2-ylamine,
4-n-propyl-6-(3-formylaminophenyl)pyrido[3,2-d]pyrimidin-2-ylamine,
4-n-propyl-6-(2-formylaminophenyl)pyrido[3,2-d]pyrimidin-2-ylamine,
4-n-propyl-6-(2-formyl-5-methoxyphenyl)pyrido[3,2-d]pyrimidin-2-ylamine,
4-n-propyl-6-(3-formyl-4-methoxyphenyl)pyrido[3,2-d]pyrimidin-2-ylamine,
4-n-propyl-6-(5-formyl-2-methoxyphenyl)pyrido[3,2-d]pyrimidin-2-ylamine,
4-n-propyl-6-(2-formyl-5-methylphenyl)pyrido[3,2-d]pyrimidin-2-ylamine,
4-n-propyl-6-(4-formylphenyl)pyrido[3,2-d]pyrimidin-2-ylamine,
4-n-propyl-6-(3-formylphenyl)pyrido[3,2-d]pyrimidin-2-ylamine,
4-n-propyl-6-(2-formylphenyl)pyrido[3,2-d]pyrimidin-2-ylamine,
4-n-propyl-6-(4-hydroxy-3,5-dimethylphenyl)pyrido[3,2-d]pyrimidin-2-ylamine,
4-n-propyl-6-(3-(2-hydroxyethyl)-aminocarbonylphenyl)pyrido[3,2-d]pyrimidin-2-ylamine,
4-n-propyl-6-(4-(2-hydroxyethyl)aminocarbonyl)phenyl)pyrido[3,2-d]pyrimidin-2-ylamine, 4-n-propyl-6-(3-hydroxy-4-methoxycarbonylphenyl)pyrido[3,2-d]pyrimidin-2-ylamine,
4-n-propyl-6-(4-hydroxy-3-methoxyphenyl)pyrido[3,2-d]pyrimidin-2-ylamine,
4-n-propyl-6-(4-(hydroxymethyl)phenyl)pyrido[3,2-d]pyrimidin-2-ylamine,
4-n-propyl-6-(3-(hydroxymethyl)phenyl)pyrido[3,2-d]pyrimidin-2-ylamine,
4-n-propyl-6-(4-hydroxy-3-nitrophenyl)pyrido[3,2-d]pyrimidin-2-ylamine,
4-n-propyl-6-(4-isopropoxyphenyl)pyrido[3,2-d]pyrimidin-2-ylamine,
4-n-propyl-6-(4-(4-isopropylpiperazinyl)phenyl)pyrido[3,2-d]pyrimidin-2-ylamine,
4-n-propyl-6-(4-isopropylphenyl)pyrido[3,2-d]pyrimidin-2-ylamine,
4-n-propyl-6-(4-methanesulfonamidophenyl)pyrido[3,2-d]pyrimidin-2-ylamine,
4-n-propyl-6-(3-methanesulfonamidophenyl)pyrido[3,2-d]pyrimidin-2-ylamine,
4-n-propyl-6-(2-methanesulfonamido phenyl)pyrido[3,2-d]pyrimidin-2-ylamine,
4-n-propyl-6-(4-methoxycarbonylphenyl)pyrido[3,2-d]pyrimidin-2-ylamine,
4-n-propyl-6-(3-methoxycarbonylphenyl)pyrido[3,2-d]pyrimidin-2-ylamine,
4-n-propyl-6-(2-methoxycarbonylphenyl)pyrido[3,2-d]pyrimidin-2-ylamine,
4-n-propyl-6-(3-methoxy-4-methoxycarbonylphenyl)pyrido[3,2-d]pyrimidin-2-ylamine,
4-n-propyl-6-(2-methoxy-5-methylphenyl)pyrido[3,2-d]pyrimidin-2-ylamine,
4-n-propyl-6-(4-methoxy-3-nitrophenyl)pyrido[3,2-d]pyrimidin-2-ylamine,
4-n-propyl-6-(4-methoxyphenyl)pyrido[3,2-d]pyrimidin-2-ylamine,
4-n-propyl-6-(3-methoxyphenyl)pyrido[3,2-d]pyrimidin-2-ylamine,
4-n-propyl-6-(4-N-methylcarboxamidophenyl)pyrido[3,2-d]pyrimidin-2-ylamine,
4-n-propyl-6-(4-(N-methylamino)phenyl)pyrido[3,2-d]pyrimidin-2-ylamine,
4-n-propyl-6-(3-(4-methylpiperazine-1-carbonyl)phenyl)pyrido[3,2-d]pyrimidin-2-ylamine,
4-n-propyl-6-(4-(4-methylpiperazine-1-carbonyl)phenyl)pyrido[3,2-d]pyrimidin-2-ylamine,
4-n-propyl-6-(4-(methylthio)phenyl)pyrido[3,2-d]pyrimidin-2-ylamine,
4-n-propyl-6-(3-(methylthio)phenyl)pyrido[3,2-d]pyrimidin-2-ylamine,
4-n-propyl-6-(2-(methylthio)phenyl)pyrido[3,2-d]pyrimidin-2-ylamine,
4-n-propyl-6-(4-(morpholinocarbonyl)phenyl)pyrido[4,2-d]pyrimidin-2-ylamine,
4-n-propyl-6-(4-morpholinophenyl)pyrido[3,2-d]pyrimidin-2-ylamine,
4-n-propyl-6-(2-(morpholinomethyl)phenyl)pyrido[3,2-d]pyrimidin-2-ylamine,
4-n-propyl-6-(4-nitrophenyl)pyrido[3,2-d]pyrimidin-2-ylamine,
4-n-propyl-6-(3-nitrophenyl)pyrido[3,2-d]pyrimidin-2-ylamine,
4-n-propyl-6-(2-nitrophenyl)pyrido[3,2-d]pyrimidin-2-ylamine,
4-n-propyl-6-(4-phenoxyphenyl)pyrido[3,2-d]pyrimidin-2-ylamine,
4-n-propyl-6-(4-(N-phenylaminomethyl)phenyl)pyrido[3,2-d]pyrimidin-2-ylamine,
4-n-propyl-6-(4-(phenylcarbonyl)phenyl)pyrido[3,2-d]pyrimidin-2-ylamine,
4-n-propyl-6-(4-(piperazine-1-carbonyl)phenyl)pyrido[3,2-d]pyrimidin-2-ylamine,
4-n-propyl-6-(4-piperazinylphenyl)pyrido[3,2-d]pyrimidin-2-ylamine,
4-n-propyl-6-(4-succinamidophenyl)pyrido[3,2-d]pyrimidin-2-ylamine,
4-n-propyl-6-(3-succinamidophenyl)pyrido[3,2-d]pyrimidin-2-ylamine,
4-n-propyl-6-(sulfamoylphenyl)pyrido[3,2-d]pyrimidin-2-ylamine,
4-n-propyl-6-(2-(toluene-4-sulfonamido)phenyl)pyrido[3,2-d]pyrimidin-2-ylamine,
4-n-propyl-6-(4-(toluene-4-sulfonamido)phenyl)pyrido[3,2-d]pyrimidin-2-ylamine,
4-n-propyl-6-(4-(tert-butoxycarbonylamino)-3-methoxyphenyl)pyrido[3,2-d]pyrimidin-2-ylamine,
4-n-propyl-6-(2-(tert-butoxycarbonyl)phenyl)pyrido[3,2-d]pyrimidin-2-ylamine,
4-n-propyl-6-(3-(tert-butoxycarbonyl)phenyl)pyrido[3,2-d]pyrimidin-2-ylamine,
4-n-propyl-6-(4-(tert-butoxycarbonyl)phenyl)pyrido[3,2-d]pyrimidin-2-ylamine,
4-n-propyl-6-(2,3,4-trifluorophenyl)pyrido[3,2-d]pyrimidin-2-ylamine,
4-n-propyl-6-(4-tert-butylphenyl)pyrido[3,2-d]pyrimidin-2-ylamine,
4-n-propyl-6-(4-(tetrahydro-2H-pyran-2-yloxy)phenyl)pyrido[3,2-d]pyrimidin-2-ylamine,
4-n-propyl-6-(4-(2-thienyl)phenyl)pyrido[3,2-d]pyrimidin-2-ylamine,
4-n-propyl-6-(2,4,6-trimethylphenyl)pyrido[3,2-d]pyrimidin-2-ylamine,
4-n-propyl-6-(3,4,5-trimethoxyphenyl)pyrido[3,2-d]pyrimidin-2-ylamine,
4-n-propyl-6-(4-vinylphenyl)pyrido[3,2-d]pyrimidin-2-ylamine,
4-n-propyl-6-(4-(2-hydroxyethoxy)phenyl)pyrido[3,2-d]pyrimidin-2-ylamine,
4-n-propyl-6-(6-benzyloxynaphth-2-yl)pyrido[3,2-d]pyrimidin-2-ylamine,
4-n-propyl-6-(naphth-1-yl)pyrido[3,2-d]pyrimidin-2-ylamine,
4-n-propyl-6-(naphth-2-yl)pyrido[3,2-d]pyrimidin-2-ylamine,
4-n-propyl-6-(4'-benzoyl[1,1'-biphenyl]-4-yl)pyrido[3,2-d]pyrimidin-2-ylamine,
4-n-propyl-6-(1-biphenylyl)pyrido[3,2-d]pyrimidin-2-ylamine,
4-n-propyl-6-(oxoindan-5-yl)pyrido[3,2-d]pyrimidin-2-ylamine,
4-n-propyl-6-(benzodioxolyl)pyrido[3,2-d]pyrimidin-2-ylamine,
4-n-propyl-6-(2-acetamidopyridin-5-yl)pyrido[3,2-d]pyrimidin-2-ylamine,
4-n-propyl-6-(2-aminopyridin-5-yl)pyrido[3,2-d]pyrimidin-2-ylamine,
4-n-propyl-6-(2-aminopyrido[3,2-d]pyrimidin-5-yl)pyrido[3,2-d]pyrimidin-2-ylamine,
4-n-propyl-6-(1,4-benzodioxan-6-yl)pyrido[3,2-d]pyrimidin-2-ylamine,
4-n-propyl-6-(1-benzothien-3-yl)pyrido[3,2-d]pyrimidin-2-ylamine, 4-n-propyl-6-(2-benzyloxypyridin-5-yl)pyrido[3,2-d]pyrimidin-2-ylamine,
4-n-propyl-6-(1-benzyl-1H-pyrazol-4-yl)pyrido[3,2-d]pyrimidin-2-ylamine,
4-n-propyl-6-(2-bromo-3-chloropyridin-4-yl)pyrido[3,2-d]pyrimidin-2-ylamine,
4-n-propyl-6-(5-bromo-2,3-dihydrobenzo[b]furan-7-yl)pyrido[3,2-d]pyrimidin-2-ylamine,
4-n-propyl-6-(2-bromo-3-methylpyridin-5-yl)pyrido[3,2-d]pyrimidin-2-ylamine,
4-n-propyl-6-(2-bromopyridin-5-yl)pyrido[3,2-d]pyrimidin-2-ylamine,
4-n-propyl-6-(3-bromopyridin-5-yl)pyrido[3,2-d]pyrimidin-2-ylamine,
4-n-propyl-6-(5-bromothien-2-yl)pyrido[3,2-d]pyrimidin-2-ylamine,
4-n-propyl-6-(2-chloro-6-isopropylpyridin-3-yl)pyrido[3,2-d]pyrimidin-2-ylamine,
4-n-propyl-6-(2-chloro-3-methylpyridin-5-yl)pyrido[3,2-d]pyrimidin-2-ylamine,
4-n-propyl-6-(2-[4-(4-chlorophenylsulfonyl)piperazin-1-yl]pyridin-5-yl)pyrido[3,2-d]pyrimidin-2-ylamine,
4-n-propyl-6-(2-chloropyrid-4-yl)pyrido[3,2-d]pyrimidin-2-ylamine,
4-n-propyl-6-(2-chloropyrid-5-yl)pyrido[3,2-d]pyrimidin-2-ylamine,
4-n-propyl-6-(dibenzo[b,d]furan-4-yl)pyrido[3,2-d]pyrimidin-2-ylamine,
4-n-propyl-6-(2-chloro-3-fluoropyridin-4-yl)pyrido[3,2-d]pyrimidin-2-ylamine,
4-n-propyl-6-(dibenzo[b,d]thien-4-yl)pyrido[3,2-d]pyrimidin-2-ylamine,
4-n-propyl-6-(3,4-dihydro-2H-1,5-benzodioxepin-7-yl)pyrido[3,2-d]pyrimidin-2-ylamine,
4-n-propyl-6-(3,6-dihydro-2H-pyridine-1-tert-butoxycarbonyl)pyrido[3,2-d]pyrimidin-2-ylamine,
4-n-propyl-6-(2,5-dibromopyridin-3-yl)pyrido[3,2-d]pyrimidin-2-ylamine,
4-n-propyl-6-(2,6-dichloropyridin-3-yl)pyrido[3,2-d]pyrimidin-2-ylamine,
4-n-propyl-6-(2,3-dihydro-1-benzofuran-5-yl)pyrido[3,2-d]pyrimidin-2-ylamine,
4-n-propyl-6-(2,6-dimethoxypyridin-5-yl)pyrido[3,2-d]pyrimidin-2-ylamine,
4-n-propyl-6-(2,6-dimethoxypyridin-3-yl)pyrido[3,2-d]pyrimidin-2-ylamine,
4-n-propyl-6-(2,4-dimethoxypyrido[3,2-d]pyrimidin-5-yl)pyrido[3,2-d]pyrimidin-2-ylamine,
4-n-propyl-6-(3,5-dimethylisoxazol-4-yl)pyrido[3,2-d]pyrimidin-2-ylamine,
4-n-propyl-6-(2-(3-N,N-dimethylaminopropoxy)pyridin-5-yl)pyrido[3,2-d]pyrimidin-2-ylamine,
4-n-propyl-6-(3,5-dimethylpyrazol-4-yl)pyrido[3,2-d]pyrimidin-2-ylamine,
4-n-propyl-6-(1-[1,3]dioxolan-2-ylmethyl-1H-pyrazol-4-yl)pyrido[3,2-d]pyrimidin-2-ylamine,
4-n-propyl-6-(2,4-dioxo-1,2,3,4-tetrahydro-5-pyrido[3,2-d]pyrimidinyl)pyrido[3,2-d]pyrimidin-2-ylamine,
4-n-propyl-6-(2,4-di(tert-butoxy)pyrido[3,2-d]pyrimidin-5-yl)pyrido[3,2-d]pyrimidin-2-ylamine,
4-n-propyl-6-(2-ethoxypyridin-3-yl)pyrido[3,2-d]pyrimidin-2-ylamine,
4-n-propyl-6-(2-fluoro-3-methylpyridin-5-yl)pyrido[3,2-d]pyrimidin-2-ylamine,
4-n-propyl-6-(2-fluoropyridin-5-yl)pyrido[3,2-d]pyrimidin-2-ylamine,
4-n-propyl-6-(5-formyl-2-furyl)pyrido[3,2-d]pyrimidin-2-ylamine,
4-n-propyl-6-(5-formylthien-2-yl)pyrido[3,2-d]pyrimidin-2-ylamine,
4-n-propyl-6-(furan-2-yl)pyrido[3,2-d]pyrimidin-2-ylamine,
4-n-propyl-6-(2-hydroxypyridin-5-yl)pyrido[3,2-d]pyrimidin-2-ylamine,
4-n-propyl-6-(1-isobutyl-1H-pyrazol-4-yl)pyrido[3,2-d]pyrimidin-2-ylamine,
4-n-propyl-6-(isoquinolin-4-yl)pyrido[3,2-d]pyrimidin-2-ylamine,
4-n-propyl-6-(2-methoxypyridin-3-yl)pyrido[3,2-d]pyrimidin-2-ylamine,
4-n-propyl-6-(2-methoxypyrido[3,2-d]pyrimidin-5-yl)pyrido[3,2-d]pyrimidin-2-ylamine,
4-n-propyl-6-(5-methyl-1-benzothien-2-yl)pyrido[3,2-d]pyrimidin-2-ylamine,
4-n-propyl-6-(1-(3-methylbutyl)-1H-pyrazol-4-yl)pyrido[3,2-d]pyrimidin-2-ylamine,
4-n-propyl-6-(5-methylfuran-2-yl)pyrido[3,2-d]pyrimidin-2-ylamine,
4-n-propyl-6-(1-methylindol-5-yl)pyrido[3,2-d]pyrimidin-2-ylamine,
4-n-propyl-6-(5-methyl-3-phenyl-4-isoxazolyl)pyrido[3,2-d]pyrimidin-2-ylamine,
4-n-propyl-6-(5-(methylthio)thien-2-yl)pyrido[3,2-d]pyrimidin-2-ylamine,
4-n-propyl-6-(2-(4-methylpiperazinyl)pyridin-4-yl)pyrido[3,2-d]pyrimidin-2-ylamine,
4-n-propyl-6-(2-(4-methylpiperazinyl)pyridin-5-yl)pyrido[3,2-d]pyrimidin-2-ylamine,
4-n-propyl-6-(1-methyl-1H-pyrazol-4-yl)pyrido[3,2-d]pyrimidin-2-ylamine,
4-n-propyl-6-(3-methylpyridin-2-yl)pyrido[3,2-d]pyrimidin-2-ylamine,
4-n-propyl-6-(5-methylpyridin-2-yl)pyrido[3,2-d]pyrimidin-2-ylamine,
4-n-propyl-6-(5-methylpyridin-3-yl)pyrido[3,2-d]pyrimidin-2-ylamine,
4-n-propyl-6-(2-methoxypyridin-5-yl)pyrido[3,2-d]pyrimidin-2-ylamine,
4-n-propyl-6-(4-methylthien-2-yl)pyrido[3,2-d]pyrimidin-2-ylamine,
4-n-propyl-6-(5-methylthien-2-yl)pyrido[3,2-d]pyrimidin-2-ylamine,
4-n-propyl-6-(2-(2-morpholinoethylamino)-pyridin-5-yl)pyrido[3,2-d]pyrimidin-2-ylamine,
4-n-propyl-6-(2-(2-morpholinoethyl)-1H-pyrazol-4-yl)pyrido[3,2-d]pyrimidin-2-ylamine,
4-n-propyl-6-(2-(morpholin-1-yl)-pyridin-5-yl)pyrido[3,2-d]pyrimidin-2-ylamine,
4-n-propyl-6-(1-(phenylsulfonyl)-1H-indol-3-yl)pyrido[3,2-d]pyrimidin-2-ylamine,
4-n-propyl-6-(5-phenyl-2-thienyl)pyrido[3,2-d]pyrimidin-2-ylamine,
4-n-propyl-6-(2-(piperazin-1-yl)-pyridin-5-yl)pyrido[3,2-d]pyrimidin-2-ylamine,
4-n-propyl-6-(2-(piperazin-1-yl)-pyridin-4-yl)pyrido[3,2-d]pyrimidin-2-ylamine,
4-n-propyl-6-(1-propyl-1H-pyrazol-4-yl)pyrido[3,2-d]pyrimidin-2-ylamine,
4-n-propyl-6-(pyrazol-4-yl)pyrido[3,2-d]pyrimidin-2-ylamine,
4-n-propyl-6-(pyridin-4-yl)pyrido[3,2-d]pyrimidin-2-ylamine, 4-n-propyl-6-(4-phenoxathiinyl)pyrido[3,2-d]pyrimidin-2-ylamine,
4-n-propyl-6-(quinolin-8-yl)pyrido[3,2-d]pyrimidin-2-ylamine,
4-n-propyl-6-(quinolin-3-yl)pyrido[3,2-d]pyrimidin-2-ylamine,
4-n-propyl-6-(2-(4-tert-butoxycarbonylpiperazinyl)-pyrid-4-yl)pyrido[3,2-d]pyrimidin-2-ylamine,
4-n-propyl-6-(1-tert-butoxycarbonyl-1H-pyrazol-4-yl)pyrido[3,2-d]pyrimidin-2-ylamine,
4-n-propyl-6-(1-tert-butoxycarbonyl-2-pyrrolyl)pyrido[3,2-d]pyrimidin-2-ylamine,
4-n-propyl-6-(1-(tert-butoxycarbonyl)-5-bromo-1H-indol-2-yl)pyrido[3,2-d]pyrimidin-2-ylamine,
4-n-propyl-6-(1-(tert-butoxycarbonyl)-1H-indol-5-yl)pyrido[3,2-d]pyrimidin-2-ylamine,
4-n-propyl-6-(1-(tert-butoxycarbonyl)-5-methoxy-1H-indol-2-yl)pyrido[3,2-d]pyrimidin-2-ylamine,
4-n-propyl-6-(1-thianthrenylthien-3-yl)pyrido[3,2-d]pyrimidin-2-ylamine, and
4-n-propyl-6-(1,3,5-trimethyl-1H-pyrazol-4-yl)pyrido[3,2-d]pyrimidin-2-ylamine.

Examples 422 to 617

Synthesis of 1-[4-(2-amino-4-ethyl-pyrido[3,2-d]pyrimidin-6-yl)-phenyl]-pyrrolidin-2-one analogues The two-steps experimental procedure of example 8 is repeated, except for the use of phenylmagnesium chloride in the first step, and the use of a different arylboronic acid or heteroarylboronic acid, or a pinacol ester thereof, in the second step. In this way, the following compounds are obtained in similar yields:
4-phenyl-6-(4-(4'-allyloxycarbonylpiperazino)phenyl)pyrimidin-2-ylamine,
4-phenyl-6-(3-aminocarbonylphenyl)pyrimidin-2-ylamine,
4-phenyl-6-(4-aminocarbonylphenyl)pyrido[3,2-d]pyrimidin-2-ylamine,
4-phenyl-6-(2-amino-5-chlorophenyl)pyrido[3,2-d]pyrimidin-2-ylamine,
4-phenyl-6-(4-amino-3-methoxyphenyl)pyrido[3,2-d]pyrimidin-2-ylamine,
4-phenyl-6-(2-amino-4-methylphenyl)pyrido[3,2-d]pyrimidin-2-ylamine,
4-phenyl-6-(2-amino-5-methylphenyl)pyrido[3,2-d]pyrimidin-2-ylamine,
4-phenyl-6-(4-amino-2-methyl phenyl)pyrido[3,2-d]pyrimidin-2-ylamine,
4-phenyl-6-(5-amino-2-methyl phenyl)pyrido[3,2-d]pyrimidin-2-ylamine,
4-phenyl-6-(4-amino-3-nitrophenyl)pyrido[3,2-d]pyrimidin-2-ylamine,
4-phenyl-6-(2-benzyloxyphenyl)pyrido[3,2-d]pyrimidin-2-ylamine,
4-phenyl-6-(3-benzyloxy-4-methoxyphenyl)pyrido[3,2-d]pyrimidin-2-ylamine,
4-phenyl-6-(4-biphenyl)pyrido[3,2-d]pyrimidin-2-ylamine,
4-phenyl-6-(4-n-butyl phenyl)pyrido[3,2-d]pyrimidin-2-ylamine,
4-phenyl-6-(4-isobutylphenyl)pyrido[3,2-d]pyrimidin-2-ylamine,
4-phenyl-6-(4-carboxy-3-fluorophenyl)pyrido[3,2-d]pyrimidin-2-ylamine,
4-phenyl-6-(3-(3-carboxypropionylamino)phenyl)pyrido[3,2-d]pyrimidin-2-ylamine,
4-phenyl-6-(4-(3-carboxypropionylamino)phenyl)pyrido[3,2-d]pyrimidin-2-ylamine,
4-phenyl-6-(3-chloro-4-hydroxy-5-methoxyphenyl)pyrido[3,2-d]pyrimidin-2-ylamine,
4-phenyl-6-(2-chloro-5-hydroxymethylphenyl)pyrido[3,2-d]pyrimidin-2-ylamine,
4-phenyl-6-(4-cyanomethoxyphenyl)pyrido[3,2-d]pyrimidin-2-ylamine,
4-phenyl-6-(3-cyanomethoxyphenyl)pyrido[3,2-d]pyrimidin-2-ylamine,
4-phenyl-6-(2-cyanomethoxyphenyl)pyrido[3,2-d]pyrimidin-2-ylamine,
4-phenyl-6-(4-cyanophenyl)pyrido[3,2-d]pyrimidin-2-ylamine,
4-phenyl-6-(3-cyanophenyl)pyrido[3,2-d]pyrimidin-2-ylamine,
4-phenyl-6-(2-cyanophenyl)pyrido[3,2-d]pyrimidin-2-ylamine,
4-phenyl-6-(3-(N-cyclopropylaminocarbonyl)phenyl)pyrido[3,2-d]pyrimidin-2-ylamine,
4-phenyl-6-(3-(N,N-diethylaminocarbonyl)phenyl)pyrido[3,2-d]pyrimidin-2-ylamine,
4-phenyl-6-(3-(N,N-dimethylamino)phenyl)pyrido[3,2-d]pyrimidin-2-ylamine,
4-phenyl-6-(2-(N,N-dimethylamino)phenyl)pyrido[3,2-d]pyrimidin-2-ylamine,
4-phenyl-6-(3-(N,N-dimethylaminocarbonyl)phenyl)pyrido[3,2-d]pyrimidin-2-ylamine,
4-phenyl-6-(3-[(N',N'-dimethylamino)ethylaminocarbonyl]phenyl)-pyrido[3,2-d]pyrimidin-2-ylamine,
4-phenyl-6-(4-[(N',N'-dimethylamino)ethylaminocarbonyl]phenyl)-pyrido[3,2-d]pyrimidin-2-ylamine,
4-phenyl-6-(3-[1,3]dioxolan-2-ylmethoxyphenyl)pyrido[3,2-d]pyrimidin-2-ylamine,
4-phenyl-6-(3-(ethoxycarbonyl)methoxyphenyl)pyrido[3,2-d]pyrimidin-2-ylamine,
4-phenyl-6-(4-(ethoxycarbonyl)methoxyphenyl)pyrido[3,2-d]pyrimidin-2-ylamine,
4-phenyl-6-(4-ethoxycarbonylphenyl)pyrido[3,2-d]pyrimidin-2-ylamine,
4-phenyl-6-(3-ethoxycarbonylphenyl)pyrido[3,2-d]pyrimidin-2-ylamine,
4-phenyl-6-(2-ethoxycarbonylphenyl)pyrido[3,2-d]pyrimidin-2-ylamine,
4-phenyl-6-(4-(3-ethoxycarbonylpiperidino)carboxamidophenyl)-pyrido[3,2-d]pyrimidin-2-ylamine,
4-phenyl-6-(4-formylaminophenyl)pyrido[3,2-d]pyrimidin-2-ylamine,
4-phenyl-6-(3-formylaminophenyl)pyrido[3,2-d]pyrimidin-2-ylamine,
4-phenyl-6-(2-formylaminophenyl)pyrido[3,2-d]pyrimidin-2-ylamine,
4-phenyl-6-(2-formyl-5-methoxyphenyl)pyrido[3,2-d]pyrimidin-2-ylamine,
4-phenyl-6-(3-formyl-4-methoxyphenyl)pyrido[3,2-d]pyrimidin-2-ylamine,
4-phenyl-6-(5-formyl-2-methoxyphenyl)pyrido[3,2-d]pyrimidin-2-ylamine,
4-phenyl 6-(2-formyl-5-methylphenyl)pyrido[3,2-d]pyrimidin-2-ylamine,
4-phenyl-6-(4-formylphenyl)pyrido[3,2-d]pyrimidin-2-ylamine,
4-phenyl-6-(3-formylphenyl)pyrido[3,2-d]pyrimidin-2-ylamine,
4-phenyl-6-(2-formylphenyl)pyrido[3,2-d]pyrimidin-2-ylamine, 4-phenyl-6-(4-hydroxy-3,5-dimethylphenyl)pyrido[3,2-d]pyrimidin-2-ylamine,
4-phenyl-6-(3-(2-hydroxyethyl)-aminocarbonylphenyl)pyrido[3,2-d]pyrimidin-2-ylamine,
4-phenyl-6-(4-(2-hydroxyethyl)aminocarbonyl)phenyl)pyrido[3,2-d]pyrimidin-2-ylamine,
4-phenyl-6-(3-hydroxy-4-methoxycarbonylphenyl)pyrido[3,2-d]pyrimidin-2-ylamine,
4-phenyl-6-(4-hydroxy-3-methoxyphenyl)pyrido[3,2-d]pyrimidin-2-ylamine,
4-phenyl-6-(4-(hydroxymethyl)phenyl)pyrido[3,2-d]pyrimidin-2-ylamine,
4-phenyl-6-(3-(hydroxymethyl)phenyl)pyrido[3,2-d]pyrimidin-2-ylamine,
4-phenyl-6-(4-hydroxy-3-nitrophenyl)pyrido[3,2-d]pyrimidin-2-ylamine,
4-phenyl-6-(4-isopropoxyphenyl)pyrido[3,2-d]pyrimidin-2-ylamine,
4-phenyl-6-(4-(4-isopropylpiperazinyl)phenyl)pyrido[3,2-d]pyrimidin-2-ylamine,
4-phenyl-6-(4-isopropylphenyl)pyrido[3,2-d]pyrimidin-2-ylamine,
4-phenyl-6-(4-methanesulfonamidophenyl)pyrido[3,2-d]pyrimidin-2-ylamine,
4-phenyl-6-(3-methanesulfonamidophenyl)pyrido[3,2-d]pyrimidin-2-ylamine,
4-phenyl-6-(2-methanesulfonamido phenyl)pyrido[3,2-d]pyrimidin-2-ylamine,
4-phenyl-6-(4-methoxycarbonylphenyl)pyrido[3,2-d]pyrimidin-2-ylamine,
4-phenyl-6-(3-methoxycarbonylphenyl)pyrido[3,2-d]pyrimidin-2-ylamine,
4-phenyl-6-(2-methoxycarbonylphenyl)pyrido[3,2-d]pyrimidin-2-ylamine,
4-phenyl-6-(3-methoxy-4-methoxycarbonylphenyl)pyrido[3,2-d]pyrimidin-2-ylamine,
4-phenyl-6-(2-methoxy-5-methylphenyl)pyrido[3,2-d]pyrimidin-2-ylamine,
4-phenyl-6-(4-methoxy-3-nitrophenyl)pyrido[3,2-d]pyrimidin-2-ylamine,
4-phenyl-6-(4-methoxyphenyl)pyrido[3,2-d]pyrimidin-2-ylamine,
4-phenyl-6-(3-methoxyphenyl)pyrido[3,2-d]pyrimidin-2-ylamine,
4-phenyl-6-(4-N-methylcarboxamidophenyl)pyrido[3,2-d]pyrimidin-2-ylamine,
4-phenyl-6-(4-(N-methylamino)phenyl)pyrido[3,2-d]pyrimidin-2-ylamine,
4-phenyl-6-(3-(4-methylpiperazine-1-carbonyl)phenyl)pyrido[3,2-d]pyrimidin-2-ylamine,
4-phenyl-6-(4-(4-methylpiperazine-1-carbonyl)phenyl)pyrido[3,2-d]pyrimidin-2-ylamine,
4-phenyl-6-(4-(methylthio)phenyl)pyrido[3,2-d]pyrimidin-2-ylamine,
4-phenyl-6-(3-(methylthio)phenyl)pyrido[3,2-d]pyrimidin-2-ylamine,
4-phenyl-6-(2-(methylthio)phenyl)pyrido[3,2-d]pyrimidin-2-ylamine,
4-phenyl-6-(4-(morpholinocarbonyl)phenyl)pyrido[3,2-d]pyrimidin-2-ylamine,
4-phenyl-6-(4-morpholinophenyl)pyrido[3,2-d]pyrimidin-2-ylamine,
4-phenyl-6-(2-(morpholinomethyl)phenyl)pyrido[3,2-d]pyrimidin-2-ylamine,
4-phenyl-6-(4-nitrophenyl)pyrido[3,2-d]pyrimidin-2-ylamine,
4-phenyl-6-(3-nitrophenyl)pyrido[3,2-d]pyrimidin-2-ylamine,
4-phenyl-6-(2-nitrophenyl)pyrido[3,2-d]pyrimidin-2-ylamine,
4-phenyl-6-(4-phenoxyphenyl)pyrido[3,2-d]pyrimidin-2-ylamine,
4-phenyl-6-(4-(N-phenylaminomethyl)phenyl)pyrido[3,2-d]pyrimidin-2-ylamine,
4-phenyl-6-(4-(phenylcarbonyl)phenyl)pyrido[3,2-d]pyrimidin-2-ylamine,
4-phenyl-6-(4-(piperazine-1-carbonyl)phenyl)pyrido[3,2-d]pyrimidin-2-ylamine,
4-phenyl-6-(4-piperazinylphenyl)pyrido[3,2-d]pyrimidin-2-ylamine,
4-phenyl-6-(4-succinamidophenyl)pyrido[3,2-d]pyrimidin-2-ylamine,
4-phenyl-6-(3-succinamidophenyl)pyrido[3,2-d]pyrimidin-2-ylamine,
4-phenyl-6-(sulfamoylphenyl)pyrido[3,2-d]pyrimidin-2-ylamine,
4-phenyl-6-(2-(toluene-4-sulfonamido)phenyl)pyrido[3,2-d]pyrimidin-2-ylamine,
4-phenyl-6-(4-(toluene-4-sulfonamido)phenyl)pyrido[3,2-d]pyrimidin-2-ylamine,
4-phenyl-6-(4-(tert-butoxycarbonylamino)-3-methoxyphenyl)pyrido[3,2-d]pyrimidin-2-ylamine,
4-phenyl-6-(2-(tert-butoxycarbonyl)phenyl)pyrido[3,2-d]pyrimidin-2-ylamine,
4-phenyl-6-(3-(tert-butoxycarbonyl)phenyl)pyrido[3,2-d]pyrimidin-2-ylamine,
4-phenyl-6-(4-(tert-butoxycarbonyl)phenyl)pyrido[3,2-d]pyrimidin-2-ylamine,
4-phenyl-6-(2,3,4-trifluorophenyl)pyrido[3,2-d]pyrimidin-2-ylamine,
4-phenyl-6-(4-tert-butylphenyl)pyrido[3,2-d]pyrimidin-2-ylamine,
4-phenyl-6-(4-(tetrahydro-2H-pyran-2-yloxy)phenyl)pyrido[3,2-d]pyrimidin-2-ylamine,
4-phenyl-6-(4-(2-thienyl)phenyl)pyrido[3,2-d]pyrimidin-2-ylamine,
4-phenyl-6-(2,4,6-trimethylphenyl)pyrido[3,2-d]pyrimidin-2-ylamine,
4-phenyl-6-(3,4,5-trimethoxyphenyl)pyrido[3,2-d]pyrimidin-2-ylamine,
4-phenyl-6-(4-vinylphenyl)pyrido[3,2-d]pyrimidin-2-ylamine,
4-phenyl-6-(4-(2-hydroxyethoxy)phenyl)pyrido[3,2-d]pyrimidin-2-ylamine,
4-phenyl-6-(6-benzyloxynaphth-2-yl)pyrido[3,2-d]pyrimidin-2-ylamine,
4-phenyl-6-(naphth-1-yl)pyrido[3,2-d]pyrimidin-2-ylamine,
4-phenyl-6-(naphth-2-yl)pyrido[3,2-d]pyrimidin-2-ylamine,
4-phenyl-6-(4'-benzoyl[1,1'-biphenyl]-4-yl)pyrido[3,2-d]pyrimidin-2-ylamine,
4-phenyl-6-(1-biphenylyl)pyrido[3,2-d]pyrimidin-2-ylamine,
4-phenyl-6-(oxoindan-5-yl)pyrido[3,2-d]pyrimidin-2-ylamine,
4-phenyl-6-(benzodioxolyl)pyrido[3,2-d]pyrimidin-2-ylamine,
4-phenyl-6-(2-acetamidopyridin-5-yl)pyrido[3,2-d]pyrimidin-2-ylamine,
4-phenyl-6-(2-aminopyridin-5-yl)pyrido[3,2-d]pyrimidin-2-ylamine,
4-phenyl-6-(2-aminopyrido[3,2-d]pyrimidin-5-yl)pyrido[3,2-d]pyrimidin-2-ylamine, 4-phenyl-6-(1,4-benzodioxan-6-yl)pyrido[3,2-d]pyrimidin-2-ylamine,
4-phenyl-6-(1-benzothien-3-yl)pyrido[3,2-d]pyrimidin-2-ylamine,
4-phenyl-6-(2-benzyloxypyridin-5-yl)pyrido[3,2-d]pyrimidin-2-ylamine,
4-phenyl-6-(1-benzyl-1H-pyrazol-4-yl)pyrido[3,2-d]pyrimidin-2-ylamine,
4-phenyl-6-(2-bromo-3-chloropyridin-4-yl)pyrido[3,2-d]pyrimidin-2-ylamine,
4-phenyl-6-(5-bromo-2,3-dihydrobenzo[b]furan-7-yl)pyrido[3,2-d]pyrimidin-2-ylamine,
4-phenyl-6-(2-bromo-3-methylpyridin-5-yl)pyrido[3,2-d]pyrimidin-2-ylamine,
4-phenyl-6-(2-bromopyridin-5-yl)pyrido[3,2-d]pyrimidin-2-ylamine,
4-phenyl-6-(3-bromopyridin-5-yl)pyrido[3,2-d]pyrimidin-2-ylamine,
4-phenyl-6-(5-bromothien-2-yl)pyrido[3,2-d]pyrimidin-2-ylamine,
4-phenyl-6-(2-chloro-6-isopropylpyridin-3-yl)pyrido[3,2-d]pyrimidin-2-ylamine,
4-phenyl-6-(2-chloro-3-methylpyridin-5-yl)pyrido[3,2-d]pyrimidin-2-ylamine,
4-phenyl-6-(2-[4-(4-chlorophenylsulfonyl)piperazin-1-yl]pyridin-5-yl)pyrido[3,2-d]pyrimidin-2-ylamine,
4-phenyl-6-(2-chloropyrid-4-yl)pyrido[3,2-d]pyrimidin-2-ylamine,
4-phenyl-6-(2-chloropyrid-5-yl)pyrido[3,2-d]pyrimidin-2-ylamine,
4-phenyl-6-(dibenzo[b,d]furan-4-yl)pyrido[3,2-d]pyrimidin-2-ylamine,
4-phenyl-6-(2-chloro-3-fluoropyridin-4-yl)pyrido[3,2-d]pyrimidin-2-ylamine,
4-phenyl-6-(dibenzo[b,d]thien-4-yl)pyrido[3,2-d]pyrimidin-2-ylamine,
4-phenyl-6-(3,4-dihydro-2H-1,5-benzodioxepin-7-yl)pyrido[3,2-d]pyrimidin-2-ylamine,
4-phenyl-6-(3,6-dihydro-2H-pyridine-1-tert-butoxycarbonyl)pyrido[3,2-d]pyrimidin-2-ylamine,
4-phenyl-6-(2,5-dibromopyridin-3-yl)pyrido[3,2-d]pyrimidin-2-ylamine,
4-phenyl-6-(2,6-dichloropyridin-3-yl)pyrido[3,2-d]pyrimidin-2-ylamine,
4-phenyl-6-(2,3-dihydro-1-benzofuran-5-yl)pyrido[3,2-d]pyrimidin-2-ylamine,
4-phenyl-6-(2,6-dimethoxypyridin-5-yl)pyrido[3,2-d]pyrimidin-2-ylamine,
4-phenyl-6-(2,6-dimethoxypyridin-3-yl)pyrido[3,2-d]pyrimidin-2-ylamine,
4-phenyl-6-(2,4-dimethoxypyrimidin-5-yl)pyrido[3,2-d]pyrimidin-2-ylamine,
4-phenyl-6-(3,5-dimethylisoxazol-4-yl)pyrido[3,2-d]pyrimidin-2-ylamine,
4-phenyl-6-(2-(3-N,N-dimethylaminopropoxy)pyridin-5-yl)pyrido[3,2-d]pyrimidin-2-ylamine,
4-phenyl-6-(3,5-dimethylpyrazol-4-yl)pyrido[3,2-d]pyrimidin-2-ylamine,
4-phenyl-6-(1-[1,3]dioxolan-2-ylmethyl-1H-pyrazol-4-yl)pyrido[3,2-d]pyrimidin-2-ylamine,
4-phenyl-6-(2,4-dioxo-1,2,3,4-tetrahydro-5-pyrimidinyl)pyrido[3,2-d]pyrimidin-2-ylamine,
4-phenyl-6-(2,4-di(tert-butoxy)pyrimidin-5-yl)pyrido[3,2-d]pyrimidin-2-ylamine,
4-phenyl-6-(2-ethoxypyridin-3-yl)pyrido[3,2-d]pyrimidin-2-ylamine,
4-phenyl-6-(2-fluoro-3-methylpyridin-5-yl)pyrido[3,2-d]pyrimidin-2-ylamine,
4-phenyl-6-(2-fluoropyridin-5-yl)pyrido[3,2-d]pyrimidin-2-ylamine,
4-phenyl-6-(5-formyl-2-furyl)pyrido[3,2-d]pyrimidin-2-ylamine,
4-phenyl-6-(5-formylthien-2-yl)pyrido[3,2-d]pyrimidin-2-ylamine,
4-phenyl-6-(furan-2-yl)pyrido[3,2-d]pyrimidin-2-ylamine,
4-phenyl-6-(2-hydroxypyridin-5-yl)pyrido[3,2-d]pyrimidin-2-ylamine,
4-phenyl-6-(1-isobutyl-1H-pyrazol-4-yl)pyrido[3,2-d]pyrimidin-2-ylamine,
4-phenyl-6-(isoquinolin-4-yl)pyrido[3,2-d]pyrimidin-2-ylamine,
4-phenyl-6-(2-methoxypyridin-3-yl)pyrido[3,2-d]pyrimidin-2-ylamine,
4-phenyl-6-(2-methoxypyrimidin-5-yl)pyrido[3,2-d]pyrimidin-2-ylamine,
4-phenyl-6-(5-methyl-1-benzothien-2-yl)pyrido[3,2-d]pyrimidin-2-ylamine,
4-phenyl-6-(1-(3-methylbutyl)-1H-pyrazol-4-yl)pyrido[3,2-d]pyrimidin-2-ylamine,
4-phenyl-6-(5-methylfuran-2-yl)pyrido[3,2-d]pyrimidin-2-ylamine,
4-phenyl-6-(1-methylindol-5-yl)pyrido[3,2-d]pyrimidin-2-ylamine,
4-phenyl-6-(5-methyl-3-phenyl-4-isoxazolyl)pyrido[3,2-d]pyrimidin-2-ylamine,
4-phenyl-6-(5-(methylthio)thien-2-yl)pyrido[3,2-d]pyrimidin-2-ylamine,
4-phenyl-6-(2-(4-methylpiperazinyl)pyridin-4-yl)pyrido[3,2-d]pyrimidin-2-ylamine,
4-phenyl-6-(2-(4-methylpiperazinyl)pyridin-5-yl)pyrido[3,2-d]pyrimidin-2-ylamine,
4-phenyl-6-(1-methyl-1H-pyrazol-4-yl)pyrido[3,2-d]pyrimidin-2-ylamine,
4-phenyl-6-(3-methylpyridin-2-yl)pyrido[3,2-d]pyrimidin-2-ylamine,
4-phenyl-6-(5-methylpyridin-2-yl)pyrido[3,2-d]pyrimidin-2-ylamine,
4-phenyl-6-(5-methylpyridin-3-yl)pyrido[3,2-d]pyrimidin-2-ylamine,
4-phenyl-6-(2-methoxypyridin-5-yl)pyrido[3,2-d]pyrimidin-2-ylamine,
4-phenyl-6-(4-methylthien-2-yl)pyrido[3,2-d]pyrimidin-2-ylamine,
4-phenyl-6-(5-methylthien-2-yl)pyrido[3,2-d]pyrimidin-2-ylamine,
4-phenyl-6-(2-(2-morpholinoethylamino)-pyridin-5-yl)pyrido[3,2-d]pyrimidin-2-ylamine,
4-phenyl-6-(2-(2-morpholinoethyl)-1H-pyrazol-4-yl)pyrido[3,2-d]pyrimidin-2-ylamine,
4-phenyl-6-(2-(morpholin-1-yl)-pyridin-5-yl)pyrido[3,2-d]pyrimidin-2-ylamine,
4-phenyl-6-(1-(phenylsulfonyl)-1H-indol-3-yl)pyrido[3,2-d]pyrimidin-2-ylamine,
4-phenyl-6-(5-phenyl-2-thienyl)pyrido[3,2-d]pyrimidin-2-ylamine,
4-phenyl-6-(2-(piperazin-1-yl)-pyridin-5-yl)pyrido[3,2-d]pyrimidin-2-ylamine,
4-phenyl-6-(2-(piperazin-1-yl)-pyridin-4-yl)pyrido[3,2-d]pyrimidin-2-ylamine,
4-phenyl-6-(1-propyl-1H-pyrazol-4-yl)pyrido[3,2-d]pyrimidin-2-ylamine,
4-phenyl-6-(pyrazol-4-yl)pyrido[3,2-d]pyrimidin-2-ylamine, 4-phenyl-6-(pyridin-4-yl)pyrido[3,2-d]pyrimidin-2-ylamine,
4-phenyl-6-(4-phenoxathiinyl)pyrido[3,2-d]pyrimidin-2-ylamine,
4-phenyl-6-(quinolin-8-yl)pyrido[3,2-d]pyrimidin-2-ylamine,
4-phenyl-6-(quinolin-3-yl)pyrido[3,2-d]pyrimidin-2-ylamine,
4-phenyl-6-(2-(4-tert-butoxycarbonylpiperazinyl)-pyrid-4-yl)pyrido[3,2-d]pyrimidin-2-ylamine,
4-phenyl-6-(1-tert-butoxycarbonyl-1H-pyrazol-4-yl)pyrido[3,2-d]pyrimidin-2-ylamine,
4-phenyl-6-(1-tert-butoxycarbonyl-2-pyrrolyl)pyrido[3,2-d]pyrimidin-2-ylamine,
4-phenyl-6-(1-(tert-butoxycarbonyl)-5-bromo-1H-indol-2-yl)pyrido[3,2-d]pyrimidin-2-ylamine,
4-phenyl-6-(1-(tert-butoxycarbonyl)-1H-indol-5-yl)pyrido[3,2-d]pyrimidin-2-ylamine,
4-phenyl-6-(1-(tert-butoxycarbonyl)-5-methoxy-1H-indol-2-yl)pyrido[3,2-d]pyrimidin-2-ylamine,
4-phenyl-6-(1-thianthrenylthien-3-yl)pyrido[3,2-d]pyrimidin-2-ylamine, and
4-phenyl-6-(1,3,5-trimethyl-1H-pyrazol-4-yl)pyrido[3,2-d]pyrimidin-2-ylamine.

Examples 618 to 813

Synthesis of 1-[4-(2-amino-4-ethyl-pyrido[3,2-d]pyrimidin-6-yl)-phenyl]-pyrrolidin-2-one analogues The two-steps experimental procedure of example 8 is repeated, except for the use of benzylmagnesium chloride in the first step, and the use of a different arylboronic acid or heteroarylboronic acid, or a pinacol ester thereof, in the second step. In this way, the following compounds are obtained in similar yields:
4-benzyl-6-(4-(4'-allyloxycarbonylpiperazino)phenyl)pyrido[3,2-d]pyrimidin-2-ylamine,
4-benzyl-6-(3-aminocarbonylphenyl)pyrido[3,2-d]pyrimidin-2-ylamine,
4-benzyl-6-(4-aminocarbonylphenyl)pyrido[3,2-d]pyrimidin-2-ylamine,
4-benzyl-6-(2-amino-5-chlorophenyl)pyrido[3,2-d]pyrimidin-2-ylamine,
4-benzyl-6-(4-amino-3-methoxyphenyl)pyrido[3,2-d]pyrimidin-2-ylamine,
4-benzyl-6-(2-amino-4-methylphenyl)pyrido[3,2-d]pyrimidin-2-ylamine,
4-benzyl-6-(2-amino-5-methylphenyl)pyrido[3,2-d]pyrimidin-2-ylamine,
4-benzyl-6-(4-amino-2-methyl phenyl)pyrido[3,2-d]pyrimidin-2-ylamine,
4-benzyl-6-(5-amino-2-methyl phenyl)pyrido[3,2-d]pyrimidin-2-ylamine,
4-benzyl-6-(4-amino-3-nitrophenyl)pyrido[3,2-d]pyrimidin-2-ylamine,
4-benzyl-6-(2-benzyloxyphenyl)pyrido[3,2-d]pyrimidin-2-ylamine,
4-benzyl-6-(3-benzyloxy-4-methoxyphenyl)pyrido[3,2-d]pyrimidin-2-ylamine,
4-benzyl-6-(4-biphenyl)pyrido[3,2-d]pyrimidin-2-ylamine,
4-benzyl-6-(4-n-butyl phenyl)pyrido[3,2-d]pyrimidin-2-ylamine,
4-benzyl-6-(4-isobutylphenyl)pyrido[3,2-d]pyrimidin-2-ylamine,
4-benzyl-6-(4-carboxy-3-fluorophenyl)pyrido[3,2-d]pyrimidin-2-ylamine,
4-benzyl-6-(3-(3-carboxypropionylamino)phenyl)pyrido[3,2-d]pyrimidin-2-ylamine,
4-benzyl-6-(4-(3-carboxypropionylamino)phenyl)pyrido[3,2-d]pyrimidin-2-ylamine,
4-benzyl-6-(3-chloro-4-hydroxy-5-methoxyphenyl)pyrido[3,2-d]pyrimidin-2-ylamine,
4-benzyl-6-(2-chloro-5-hydroxymethylphenyl)pyrido[3,2-d]pyrimidin-2-ylamine,
4-benzyl-6-(4-cyanomethoxyphenyl)pyrido[3,2-d]pyrimidin-2-ylamine,
4-benzyl-6-(3-cyanomethoxyphenyl)pyrido[3,2-d]pyrimidin-2-ylamine,
4-benzyl-6-(2-cyanomethoxyphenyl)pyrido[3,2-d]pyrimidin-2-ylamine,
4-benzyl-6-(4-cyanophenyl)pyrido[3,2-d]pyrimidin-2-ylamine,
4-benzyl-6-(3-cyanophenyl)pyrido[3,2-d]pyrimidin-2-ylamine,
4-benzyl-6-(2-cyanophenyl)pyrido[3,2-d]pyrimidin-2-ylamine,
4-benzyl-6-(3-(N-cyclopropylaminocarbonyl)phenyl)pyrido[3,2-d]pyrimidin-2-ylamine,
4-benzyl-6-(3-(N,N-diethylaminocarbonyl)phenyl)pyrido[3,2-d]pyrimidin-2-ylamine,
4-benzyl-6-(3-(N,N-dimethylamino)phenyl)pyrido[3,2-d]pyrimidin-2-ylamine,
4-benzyl-6-(2-(N,N-dimethylamino)phenyl)pyrido[3,2-d]pyrimidin-2-ylamine,
4-benzyl-6-(3-(N,N-dimethylaminocarbonyl)phenyl)pyrido[3,2-d]pyrimidin-2-ylamine,
4-benzyl-6-(3-[(N',N'-dimethylamino)ethylaminocarbonyl]phenyl)-pyrido[3,2-d]pyrimidin-2-ylamine,
4-benzyl-6-(4-[(N',N'-dimethylamino)ethylaminocarbonyl]phenyl)-pyrido[3,2-d]pyrimidin-2-ylamine,
4-benzyl-6-(3-[1,3]dioxolan-2-ylmethoxyphenyl)pyrido[3,2-d]pyrimidin-2-ylamine,
4-benzyl-6-(3-(ethoxycarbonyl)methoxyphenyl)pyrido[3,2-d]pyrimidin-2-ylamine,
4-benzyl-6-(4-(ethoxycarbonyl)methoxyphenyl)pyrido[3,2-d]pyrimidin-2-ylamine,
4-benzyl-6-(4-ethoxycarbonylphenyl)pyrido[3,2-d]pyrimidin-2-ylamine,
4-benzyl-6-(3-ethoxycarbonylphenyl)pyrido[3,2-d]pyrimidin-2-ylamine,
4-benzyl-6-(2-ethoxycarbonylphenyl)pyrido[3,2-d]pyrimidin-2-ylamine,
4-benzyl-6-(4-(3-ethoxycarbonylpiperidino)carboxamidophenyl)-pyrido[3,2-d]pyrimidin-2-ylamine,
4-benzyl-6-(4-formylaminophenyl)pyrido[3,2-d]pyrimidin-2-ylamine,
4-benzyl-6-(3-formylaminophenyl)pyrido[3,2-d]pyrimidin-2-ylamine,
4-benzyl-6-(2-formylaminophenyl)pyrido[3,2-d]pyrimidin-2-ylamine,
4-benzyl-6-(2-formyl-5-methoxyphenyl)pyrido[3,2-d]pyrimidin-2-ylamine,
4-benzyl-6-(3-formyl-4-methoxyphenyl)pyrido[3,2-d]pyrimidin-2-ylamine,
4-benzyl-6-(5-formyl-2-methoxyphenyl)pyrido[3,2-d]pyrimidin-2-ylamine,
4-benzyl-6-(2-formyl-5-methylphenyl)pyrido[3,2-d]pyrimidin-2-ylamine,
4-benzyl-6-(4-formylphenyl)pyrido[3,2-d]pyrimidin-2-ylamine,
4-benzyl-6-(3-formylphenyl)pyrido[3,2-d]pyrimidin-2-ylamine, 4-benzyl-6-(2-formylphenyl)pyrido[3,2-d]pyrimidin-2-ylamine,
4-benzyl-6-(4-hydroxy-3,5-dimethylphenyl)pyrido[3,2-d]pyrimidin-2-ylamine,
4-benzyl-6-(3-(2-hydroxyethyl)-aminocarbonylphenyl)pyrido[3,2-d]pyrimidin-2-ylamine,
4-benzyl-6-(4-(2-hydroxyethyl)aminocarbonyl)phenyl)pyrido[3,2-d]pyrimidin-2-ylamine,
4-benzyl-6-(3-hydroxy-4-methoxycarbonylphenyl)pyrido[3,2-d]pyrimidin-2-ylamine,
4-benzyl-6-(4-hydroxy-3-methoxyphenyl)pyrido[3,2-d]pyrimidin-2-ylamine,
4-benzyl-6-(4-(hydroxymethyl)phenyl)pyrido[3,2-d]pyrimidin-2-ylamine,
4-benzyl-6-(3-(hydroxymethyl)phenyl)pyrido[3,2-d]pyrimidin-2-ylamine,
4-benzyl-6-(4-hydroxy-3-nitrophenyl)pyrido[3,2-d]pyrimidin-2-ylamine,
4-benzyl-6-(4-isopropoxyphenyl)pyrido[3,2-d]pyrimidin-2-ylamine,
4-benzyl-6-(4-(4-isopropylpiperazinyl)phenyl)pyrido[3,2-d]pyrimidin-2-ylamine,
4-benzyl-6-(4-isopropylphenyl)pyrido[3,2-d]pyrimidin-2-ylamine,
4-benzyl-6-(4-methanesulfonamidophenyl)pyrido[3,2-d]pyrimidin-2-ylamine,
4-benzyl-6-(3-methanesulfonamidophenyl)pyrido[3,2-d]pyrimidin-2-ylamine,
4-benzyl-6-(2-methanesulfonamido phenyl)pyrido[3,2-d]pyrimidin-2-ylamine,
4-benzyl-6-(4-methoxycarbonylphenyl)pyrido[3,2-d]pyrimidin-2-ylamine,
4-benzyl-6-(3-methoxycarbonylphenyl)pyrido[3,2-d]pyrimidin-2-ylamine,
4-benzyl-6-(2-methoxycarbonylphenyl)pyrido[3,2-d]pyrimidin-2-ylamine,
4-benzyl-6-(3-methoxy-4-methoxycarbonylphenyl)pyrido[3,2-d]pyrimidin-2-ylamine,
4-benzyl-6-(2-methoxy-5-methylphenyl)pyrido[3,2-d]pyrimidin-2-ylamine,
4-benzyl-6-(4-methoxy-3-nitrophenyl)pyrido[3,2-d]pyrimidin-2-ylamine,
4-benzyl-6-(4-methoxyphenyl)pyrido[3,2-d]pyrimidin-2-ylamine,
4-benzyl-6-(3-methoxyphenyl)pyrido[3,2-d]pyrimidin-2-ylamine,
4-benzyl-6-(4-N-methylcarboxamidophenyl)pyrido[3,2-d]pyrimidin-2-ylamine,
4-benzyl-6-(4-(N-methylamino)phenyl)pyrido[3,2-d]pyrimidin-2-ylamine,
4-benzyl-6-(3-(4-methylpiperazine-1-carbonyl)phenyl)pyrido[3,2-d]pyrimidin-2-ylamine,
4-benzyl-6-(4-(4-methylpiperazine-1-carbonyl)phenyl)pyrido[3,2-d]pyrimidin-2-ylamine,
4-benzyl-6-(4-(methylthio)phenyl)pyrido[3,2-d]pyrimidin-2-ylamine,
4-benzyl-6-(3-(methylthio)phenyl)pyrido[3,2-d]pyrimidin-2-ylamine,
4-benzyl-6-(2-(methylthio)phenyl)pyrido[3,2-d]pyrimidin-2-ylamine,
4-benzyl-6-(4-(morpholinocarbonyl)phenyl)pyrido[3,2-d]pyrimidin-2-ylamine,
4-benzyl-6-(4-morpholinophenyl)pyrido[3,2-d]pyrimidin-2-ylamine,
4-benzyl-6-(2-(morpholinomethyl)phenyl)pyrido[3,2-d]pyrimidin-2-ylamine,
4-benzyl-6-(4-nitrophenyl)pyrido[3,2-d]pyrimidin-2-ylamine,
4-benzyl-6-(3-nitrophenyl)pyrido[3,2-d]pyrimidin-2-ylamine,
4-benzyl-6-(2-nitrophenyl)pyrido[3,2-d]pyrimidin-2-ylamine,
4-benzyl-6-(4-phenoxyphenyl)pyrido[3,2-d]pyrimidin-2-ylamine,
4-benzyl-6-(4-(N-phenylaminomethyl)phenyl)pyrido[3,2-d]pyrimidin-2-ylamine,
4-benzyl-6-(4-(phenylcarbonyl)phenyl)pyrido[3,2-d]pyrimidin-2-ylamine,
4-benzyl-6-(4-(piperazine-1-carbonyl)phenyl)pyrido[3,2-d]pyrimidin-2-ylamine,
4-benzyl-6-(4-piperazinylphenyl)pyrido[3,2-d]pyrimidin-2-ylamine,
4-benzyl-6-(4-succinamidophenyl)pyrido[3,2-d]pyrimidin-2-ylamine,
4-benzyl-6-(3-succinamidophenyl)pyrido[3,2-d]pyrimidin-2-ylamine,
4-benzyl-6-(sulfamoylphenyl)pyrido[3,2-d]pyrimidin-2-ylamine,
4-benzyl-6-(2-(toluene-4-sulfonamido)phenyl)pyrido[3,2-d]pyrimidin-2-ylamine,
4-benzyl-6-(4-(toluene-4-sulfonamido)phenyl)pyrido[3,2-d]pyrimidin-2-ylamine,
4-benzyl-6-(4-(tert-butoxycarbonylamino)-3-methoxyphenyl)pyrido[3,2-d]pyrimidin-2-ylamine,
4-benzyl-6-(2-(tert-butoxycarbonyl)phenyl)pyrido[3,2-d]pyrimidin-2-ylamine,
4-benzyl-6-(3-(tert-butoxycarbonyl)phenyl)pyrido[3,2-d]pyrimidin-2-ylamine,
4-benzyl-6-(4-(tert-butoxycarbonyl)phenyl)pyrido[3,2-d]pyrimidin-2-ylamine,
4-benzyl-6-(2,3,4-trifluorophenyl)pyrido[3,2-d]pyrimidin-2-ylamine,
4-benzyl-6-(4-tert-butylphenyl)pyrido[3,2-d]pyrimidin-2-ylamine,
4-benzyl-6-(4-(tetrahydro-2H-pyran-2-yloxy)phenyl)pyrido[3,2-d]pyrimidin-2-ylamine,
4-benzyl-6-(4-(2-thienyl)phenyl)pyrido[3,2-d]pyrimidin-2-ylamine,
4-benzyl-6-(2,4,6-trimethylphenyl)pyrido[3,2-d]pyrimidin-2-ylamine,
4-benzyl-6-(3,4,5-trimethoxyphenyl)pyrido[3,2-d]pyrimidin-2-ylamine,
4-benzyl-6-(4-vinylphenyl)pyrido[3,2-d]pyrimidin-2-ylamine,
4-benzyl-6-(4-(2-hydroxyethoxy)phenyl)pyrido[3,2-d]pyrimidin-2-ylamine,
4-benzyl-6-(6-benzyloxynaphth-2-yl)pyrido[3,2-d]pyrimidin-2-ylamine,
4-benzyl-6-(naphth-1-yl)pyrido[3,2-d]pyrimidin-2-ylamine,
4-benzyl-6-(naphth-2-yl)pyrido[3,2-d]pyrimidin-2-ylamine,
4-benzyl-6-(4'-benzoyl[1,1'-biphenyl]-4-yl)pyrido[3,2-d]pyrimidin-2-ylamine,
4-benzyl-6-(1-biphenylyl)pyrido[3,2-d]pyrimidin-2-ylamine,
4-benzyl-6-(oxoindan-5-yl)pyrido[3,2-d]pyrimidin-2-ylamine,
4-benzyl-6-(benzodioxolyl)pyrido[3,2-d]pyrimidin-2-ylamine,
4-benzyl-6-(2-acetamidopyridin-5-yl)pyrido[3,2-d]pyrimidin-2-ylamine,
4-benzyl-6-(2-aminopyridin-5-yl)pyrido[3,2-d]pyrimidin-2-ylamine, 4-benzyl-6-(2-aminopyrido[3,2-d]pyrimidin-5-yl)pyrido[3,2-d]pyrimidin-2-ylamine,
4-benzyl-6-(1,4-benzodioxan-6-yl)pyrido[3,2-d]pyrimidin-2-ylamine,
4-benzyl-6-(1-benzothien-3-yl)pyrido[3,2-d]pyrimidin-2-ylamine,
4-benzyl-6-(2-benzyloxypyridin-5-yl)pyrido[3,2-d]pyrimidin-2-ylamine,
4-benzyl-6-(1-benzyl-1H-pyrazol-4-yl)pyrido[3,2-d]pyrimidin-2-ylamine,
4-benzyl-6-(2-bromo-3-chloropyridin-4-yl)pyrido[3,2-d]pyrimidin-2-ylamine,
4-benzyl-6-(5-bromo-2,3-dihydrobenzo[b]furan-7-yl)pyrido[3,2-d]pyrimidin-2-ylamine,
4-benzyl-6-(2-bromo-3-methylpyridin-5-yl)pyrido[3,2-d]pyrimidin-2-ylamine,
4-benzyl-6-(2-bromopyridin-5-yl)pyrido[3,2-d]pyrimidin-2-ylamine,
4-benzyl-6-(3-bromopyridin-5-yl)pyrido[3,2-d]pyrimidin-2-ylamine,
4-benzyl-6-(5-bromothien-2-yl)pyrido[3,2-d]pyrimidin-2-ylamine,
4-benzyl-6-(2-chloro-6-isopropylpyridin-3-yl)pyrido[3,2-d]pyrimidin-2-ylamine,
4-benzyl-6-(2-chloro-3-methylpyridin-5-yl)pyrido[3,2-d]pyrimidin-2-ylamine,
4-benzyl-6-(2-[4-(4-chlorophenylsulfonyl)piperazin-1-yl]pyridin-5-yl)pyrido[3,2-d]pyrimidin-2-ylamine,
4-benzyl-6-(2-chloropyrid-4-yl)pyrido[3,2-d]pyrimidin-2-ylamine,
4-benzyl-6-(2-chloropyrid-5-yl)pyrido[3,2-d]pyrimidin-2-ylamine,
4-benzyl-6-(dibenzo[b,d]furan-4-yl)pyrido[3,2-d]pyrimidin-2-ylamine,
4-benzyl-6-(2-chloro-3-fluoropyridin-4-yl)pyrido[3,2-d]pyrimidin-2-ylamine,
4-benzyl-6-(dibenzo[b,d]thien-4-yl)pyrido[3,2-d]pyrimidin-2-ylamine,
4-benzyl-6-(3,4-dihydro-2H-1,5-benzodioxepin-7-yl)pyrido[3,2-d]pyrimidin-2-ylamine,
4-benzyl-6-(3,6-dihydro-2H-pyridine-1-tert-butoxycarbonyl)pyrido[3,2-d]pyrimidin-2-ylamine,
4-benzyl-6-(2,5-dibromopyridin-3-yl)pyrido[3,2-d]pyrimidin-2-ylamine,
4-benzyl-6-(2,6-dichloropyridin-3-yl)pyrido[3,2-d]pyrimidin-2-ylamine,
4-benzyl-6-(2,3-dihydro-1-benzofuran-5-yl)pyrido[3,2-d]pyrimidin-2-ylamine,
4-benzyl-6-(2,6-dimethoxypyridin-5-yl)pyrido[3,2-d]pyrimidin-2-ylamine,
4-benzyl-6-(2,6-dimethoxypyridin-3-yl)pyrido[3,2-d]pyrimidin-2-ylamine,
4-benzyl-6-(2,4-dimethoxypyrimidin-5-yl)pyrido[3,2-d]pyrimidin-2-ylamine,
4-benzyl-6-(3,5-dimethylisoxazol-4-yl)pyrido[3,2-d]pyrimidin-2-ylamine,
4-benzyl-6-(2-(3-N,N-dimethylaminopropoxy)pyridin-5-yl)pyrido[3,2-d]pyrimidin-2-ylamine,
4-benzyl-6-(3,5-dimethylpyrazol-4-yl)pyrido[3,2-d]pyrimidin-2-ylamine,
4-benzyl-6-(1-[1,3]dioxolan-2-ylmethyl-1H-pyrazol-4-yl)pyrido[3,2-d]pyrimidin-2-ylamine,
4-benzyl-6-(2,4-dioxo-1,2,3,4-tetrahydro-5-pyrimidinyl)pyrido[3,2-d]pyrimidin-2-ylamine,
4-benzyl-6-(2,4-di(tert-butoxy)pyrimidin-5-yl)pyrido[3,2-d]pyrimidin-2-ylamine,
4-benzyl-6-(2-ethoxypyridin-3-yl)pyrido[3,2-d]pyrimidin-2-ylamine,
4-benzyl-6-(2-fluoro-3-methylpyridin-5-yl)pyrido[3,2-d]pyrimidin-2-ylamine,
4-benzyl-6-(2-fluoropyridin-5-yl)pyrido[3,2-d]pyrimidin-2-ylamine,
4-benzyl-6-(5-formyl-2-furyl)pyrido[3,2-d]pyrimidin-2-ylamine,
4-benzyl-6-(5-formylthien-2-yl)pyrido[3,2-d]pyrimidin-2-ylamine,
4-benzyl-6-(furan-2-yl)pyrido[3,2-d]pyrimidin-2-ylamine,
4-benzyl-6-(2-hydroxypyridin-5-yl)pyrido[3,2-d]pyrimidin-2-ylamine,
4-benzyl-6-(1-isobutyl-1H-pyrazol-4-yl)pyrido[3,2-d]pyrimidin-2-ylamine,
4-benzyl-6-(isoquinolin-4-yl)pyrido[3,2-d]pyrimidin-2-ylamine,
4-benzyl-6-(2-methoxypyridin-3-yl)pyrido[3,2-d]pyrimidin-2-ylamine,
4-benzyl-6-(2-methoxypyrimidin-5-yl)pyrido[3,2-d]pyrimidin-2-ylamine,
4-benzyl-6-(5-methyl-1-benzothien-2-yl)pyrido[3,2-d]pyrimidin-2-ylamine,
4-benzyl-6-(1-(3-methylbutyl)-1H-pyrazol-4-yl)pyrido[3,2-d]pyrimidin-2-ylamine,
4-benzyl-6-(5-methylfuran-2-yl)pyrido[3,2-d]pyrimidin-2-ylamine,
4-benzyl-6-(1-methylindol-5-yl)pyrido[3,2-d]pyrimidin-2-ylamine,
4-benzyl-6-(5-methyl-3-phenyl-4-isoxazolyl)pyrido[3,2-d]pyrimidin-2-ylamine,
4-benzyl-6-(5-(methylthio)thien-2-yl)pyrido[3,2-d]pyrimidin-2-ylamine,
4-benzyl-6-(2-(4-methylpiperazinyl)pyridin-4-yl)pyrido[3,2-d]pyrimidin-2-ylamine,
4-benzyl-6-(2-(4-methylpiperazinyl)pyridin-5-yl)pyrido[3,2-d]pyrimidin-2-ylamine,
4-benzyl-6-(1-methyl-1H-pyrazol-4-yl)pyrido[3,2-d]pyrimidin-2-ylamine,
4-benzyl-6-(3-methylpyridin-2-yl)pyrido[3,2-d]pyrimidin-2-ylamine,
4-benzyl-6-(5-methylpyridin-2-yl)pyrido[3,2-d]pyrimidin-2-ylamine,
4-benzyl-6-(5-methylpyridin-3-yl)pyrido[3,2-d]pyrimidin-2-ylamine,
4-benzyl-6-(2-methoxypyridin-5-yl)pyrido[3,2-d]pyrimidin-2-ylamine,
4-benzyl-6-(4-methylthien-2-yl)pyrido[3,2-d]pyrimidin-2-ylamine,
4-benzyl-6-(5-methylthien-2-yl)pyrido[3,2-d]pyrimidin-2-ylamine,
4-benzyl-6-(2-(2-morpholinoethylamino)-pyridin-5-yl)pyrido[3,2-d]pyrimidin-2-ylamine,
4-benzyl-6-(2-(2-morpholinoethyl)-1H-pyrazol-4-yl)pyrido[3,2-d]pyrimidin-2-ylamine,
4-benzyl-6-(2-(morpholin-1-yl)-pyridin-5-yl)pyrido[3,2-d]pyrimidin-2-ylamine,
4-benzyl-6-(1-(phenylsulfonyl)-1H-indol-3-yl)pyrido[3,2-d]pyrimidin-2-ylamine,
4-benzyl-6-(5-phenyl-2-thienyl)pyrido[3,2-d]pyrimidin-2-ylamine,
4-benzyl-6-(2-(piperazin-1-yl)-pyridin-5-yl)pyrido[3,2-d]pyrimidin-2-ylamine,
4-benzyl-6-(2-(piperazin-1-yl)-pyridin-4-yl)pyrido[3,2-d]pyrimidin-2-ylamine,
4-benzyl-6-(1-propyl-1H-pyrazol-4-yl)pyrido[3,2-d]pyrimidin-2-ylamine, 4-benzyl-6-(pyrazol-4-yl)pyrido[3,2-d]pyrimidin-2-ylamine,
4-benzyl-6-(pyridin-4-yl)pyrido[3,2-d]pyrimidin-2-ylamine,
4-benzyl-6-(4-phenoxathiinyl)pyrido[3,2-d]pyrimidin-2-ylamine,
4-benzyl-6-(quinolin-8-yl)pyrido[3,2-d]pyrimidin-2-ylamine,
4-benzyl-6-(quinolin-3-yl)pyrido[3,2-d]pyrimidin-2-ylamine,
4-benzyl-6-(2-(4-tert-butoxycarbonylpiperazinyl)-pyrid-4-yl)pyrido[3,2-d]pyrimidin-2-ylamine,
4-benzyl-6-(1-tert-butoxycarbonyl-1H-pyrazol-4-yl)pyrido[3,2-d]pyrimidin-2-ylamine,
4-benzyl-6-(1-tert-butoxycarbonyl-2-pyrrolyl)pyrido[3,2-d]pyrimidin-2-ylamine,
4-benzyl-6-(1-(tert-butoxycarbonyl)-5-bromo-1H-indol-2-yl)pyrido[3,2-d]pyrimidin-2-ylamine,
4-benzyl-6-(1-(tert-butoxycarbonyl)-1H-indol-5-yl)pyrido[3,2-d]pyrimidin-2-ylamine,
4-benzyl-6-(1-(tert-butoxycarbonyl)-5-methoxy-1H-indol-2-yl)pyrido[3,2-d]pyrimidin-2-ylamine,
4-benzyl-6-(1-thianthrenylthien-3-yl)pyrido[3,2-d]pyrimidin-2-ylamine, and
4-benzyl-6-(1,3,5-trimethyl-1H-pyrazol-4-yl)pyrido[3,2-d]pyrimidin-2-ylamine.

The invention claimed is:
1. A pyrido(3,2-d)pyrimidine derivative represented by the structural formula:

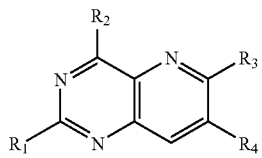

wherein:
$R_1$ is selected from the group consisting of hydrogen; halogen; cyano; carboxylic acid; acyl; thioacyl; $C_{1-7}$ alkoxycarbonyl; acyloxy; carbonate; carbamate; $C_{1-7}$ alkyl; aryl; amino; acylamino; thioacylamino; N-protected amino; (mono- or di-) $C_{1-7}$ alkylamino; (mono- or di-) arylamino; (mono- or di-) $C_{3-10}$ cycloalkylamino; (mono- or di-) hydroxy $C_{1-7}$ alkylamino; (mono- or di-) $C_{1-7}$ alkyl-arylamino; mercapto $C_{1-7}$ alkyl; $C_{1-7}$ alkyloxy; and groups having the structural formula $R_6$—$NR_7R_{12}$, wherein $R_6$ is a bond or $C_{1-7}$ alkylene, and wherein $R_7$ and $R_{12}$ are independently selected from the group consisting of hydrogen, $C_{1-7}$ alkyl, $C_{2-7}$ alkenyl, $C_{2-7}$ alkynyl, aryl $C_{1-7}$ alkyl, $C_{3-10}$ cycloalkyl, aryl and heteroaryl, wherein said aryl or heteroaryl is optionally substituted with one or more substituents independently selected from the group consisting of halogen and $C_{1-7}$ alkyl, and wherein said $C_{3-10}$ cycloalkyl is optionally substituted at the carbon position adjacent to the nitrogen atom to which it is attached, with aryl or heteroaryl wherein said aryl or heteroaryl is optionally substituted with halogen, or wherein $R_7$ and $R_{12}$ together with the nitrogen to which they are attached form a heterocyclic group; and groups having the structural formula —NH—$CHR_8R_8'$ wherein $R_8$ is selected from the group consisting of $C_{1-7}$ alkyl substituted with one or more substituents independently selected from the group consisting of halogen and $C_{1-7}$ alkoxy, $C_{3-10}$ cycloalkyl, aryl substituted with one or more $R_{14}$, and heterocyclyl, and wherein $R_8'$ is selected from the group consisting of hydrogen, $C_{1-7}$ alkyl optionally substituted with one or more substituents independently selected from the group consisting of halogen and $C_{1-7}$ alkoxy, $C_{3-10}$ cycloalkyl, aryl optionally substituted with one or more $R_{14}$, and heterocyclyl;
$R_2$ is selected from the group consisting of $C_{1-14}$ alkyl, $C_{2-7}$ alkenyl, $C_{2-7}$ alkynyl, and $C_{1-7}$alkoxy-$C_{1-7}$alkyl;
$R_4$ is hydrogen and $R_3$ is a heteroaryl or aryl group, wherein said heteroaryl or aryl group is optionally substituted with one or more substituents independently selected from the group consisting of halogen, $C_{1-7}$ alkyl, $C_{2-7}$ alkenyl, $C_{2-7}$ alkynyl, halo $C_{1-7}$ alkyl, $C_{3-10}$ cycloalkyl, aryl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclyl, arylalkylthio, heterocyclyl-$C_{1-7}$ alkylthio, formyl, —CO—$NHR_9$, —CO—$NR_9R_9'$, —CS—$NHR_9$, —$NR_{13}$—CO—$NHR_{13}$, —$NR_{13}$—CS—$NHR_{13}$, —$SO_2NH_2$, —$NR_{13}$—$SO_2R_{11}$, —$NR_{13}$—$COR_{10}$, —$NR_{13}$—$CSR_{10}$, hydroxylamino, $C_{1-7}$ alkoxyamino, mercaptoamino, thioalkylamino, cyano, carboxylic acid or esters or thioesters or halides or anhydrides or amides thereof, thiocarboxylic acid or esters or thioesters or halides or anhydrides or amides thereof, $C_{1-7}$ alkylamino, $C_{3-10}$ cycloalkylamino, $C_{2-7}$ alkenylamino, $C_{3-10}$cycloalkenylamino, $C_{2-7}$alkynylamino, arylamino, aryl$C_{1-7}$alkylamino, hydroxy $C_{1-7}$alkylamino, mercapto $C_{1-7}$alkylamino, heterocyclylamino, $C_{1-7}$ alkylsulfoxide, $C_{1-7}$ alkylsulfone, hydrazino, $C_{1-7}$ alkylhydrazino, phenylhydrazino, and heterocyclyl optionally substituted with one or more substituents independently selected from the group consisting of hydroxy, oxo, halogen, amino, $C_{1-7}$ alkyl and $C_{1-7}$alkoxy;
$R_9$ and $R_9'$ are each independently selected from the group consisting of hydrogen, $C_{3-10}$ cycloalkyl optionally substituted with one more substituents independently selected from the group consisting of cyano, halogen, hydroxy, amino, $C_{1-7}$ alkyl and $C_{1-7}$ alkoxy; $C_{1-7}$ alkoxy; $C_{1-7}$ alkyl optionally substituted with one or more substituents independently selected from the group consisting of amino $C_{1-7}$ alkylamino, cyano, di-$C_{1-7}$ alkylamino, halogen, and heterocyclyl optionally substituted with $C_{1-7}$alkyl; aryl and aryl$C_{1-7}$alkyl wherein the aryl moiety is optionally substituted with one or more halogens; or $R_9$ and $R_9'$ together with the nitrogen atom to which they are attached form a heterocyclyl group;
each $R_{10}$ and each $R_{11}$ is independently selected from the group consisting of $C_{1-7}$ alkyl optionally substituted with one or more substituents independently selected from the group consisting of amino, cyano, halogen and hydroxy; $C_{1-7}$ alkoxy optionally substituted with one or more substituents independently selected from the group consisting of amino, $C_{1-7}$ alkylamino, cyano, di-$C_{1-7}$ alkylamino, halogen, and heterocyclyl optionally substituted with one or more substituents independently selected from the group consisting of $C_{1-7}$ alkyl, acylamino and oxo; $C_{3-10}$ cycloalkyl optionally substituted with one or more substituents independently selected from the group consisting of amino and hydroxy; and amino optionally substituted with one or more substituents independently selected from the group consisting of $C_{1-7}$ alkyl wherein said $C_{1-7}$ alkyl is optionally substituted with one or more substituents independently selected from the group consisting of amino, $C_{1-7}$ alkylamino, cyano, di-$C_{1-7}$ alkylamino, halogen and heterocyclyl;

each $R_{13}$ is hydrogen or $C_{1-7}$ alkyl, optionally substituted with one or more substituents independently selected from the group consisting of cyano, halogen and hydroxy;

each $R_{14}$ is independently selected from the group consisting of halogen, hydroxy, amino, nitro, cyano, halo $C_{1-7}$ alkyl, halo $C_{1-7}$ alkoxy, $C_{1-7}$ alkyl, $C_{1-7}$ alkoxy, di-$C_{1-7}$ alkylamino, mono-$C_{1-7}$ alkylamino, carboxamido, —SO$_2$NH$_2$, carbamoyl, —NR$_{13}$—SO$_2$R$_{11}$ and phenoxy, or a pharmaceutical acceptable addition salt or a stereochemical isomeric form thereof or a N-oxide thereof, provided said pyrido(3,2-d)pyrimidine derivative is not 2-amino-4-n-propyl-6-(4-fluorophenyl)-pyrido(3,2-d)pyrimidine.

2. A pyrido(3,2-d)pyrimidine derivative according to claim 1, wherein R$_1$ is not hydrogen.

3. A pyrido(3,2-d)pyrimidine derivative according to claim 1, wherein R$_1$ is amino or acetamido.

4. A pyrido(3,2-d)pyrimidine derivative according to claim 1, wherein R$_3$ is a phenyl group substituted with one substituent.

5. A pyrido(3,2-d)pyrimidine derivative according to claim 1, wherein R$_2$ is selected from the group consisting of methyl, ethyl, n-propyl, isopropyl and but-3-enyl.

6. A pyrido(3,2-d)pyrimidine derivative according to claim 1, wherein R$_3$ is a phenyl group substituted with a substituent selected from the group consisting of fluoro and acetamido.

7. A pyrido(3,2-d)pyrimidine derivative according to claim 1, wherein R$_3$ is a phenyl group substituted with one substituent in para position on said phenyl group.

8. A pyrido(3,2-d)pyrimidine derivative being 2-amino-4-n-propyl-6-(4-fluorophenyl)-pyrido(3,2-d)pyrimidine or a pharmaceutical acceptable addition salt or a stereochemical isomeric form thereof or a N-oxide thereof.

9. A pyrido(3,2-d)pyrimidine derivative, being selected from the group consisting of:
  6-(4-fluoro-phenyl)-4-isopropyl-pyrido[3,2-d]pyrimidin-2-ylamine,
  4-methyl-6-(4-fluorophenyl)-pyrido[3,2-d]pyrimidin-2-ylamine,
  6-(5-amino-pyrazin-2-yl)-4-ethyl-pyrido[3,2-d]pyrimidin-2-ylamine,
  1-[4-(2-amino-4-ethyl-pyrido[3,2-d]pyrimidin-6-yl)-phenyl]-pyrrolidin-2-one,
  4-but-3-enyl-6-(4-fluoro-phenyl)-pyrido[3,2-d]pyrimidin-2-ylamine,
  6-(4-fluoro-phenyl)-4-isobutyl-pyrido[3,2-d]pyrimidin-2-ylamine,
  4-ethyl-6-(4-fluoro-phenyl)-pyrido[3,2-d]pyrimidin-2-ylamine,
  6-(4-fluoro-phenyl)-4-n-propyl-pyrido[3,2-d]pyrimidine,
  N-[4-(2-amino-4-n-propyl-pyrido[3,2-d]pyrimidin-6-yl)-phenyl]-acetamide,
  6-(4-fluorophenyl)-4-methyl-pyrido[3,2-d]pyrimidine,
  6-(4-fluorophenyl)-4-ethyl-pyrido[3,2-d]pyrimidine,
  6-(4-fluorophenyl)-4-isopropyl-pyrido[3,2-d]pyrimidine,
  6-(4-fluorophenyl)-4-isobutyl-pyrido[3,2-d]pyrimidine,
  6-(4-fluorophenyl)-4-pentyl-pyrido[3,2-d]pyrimidine,
  6-(4-fluorophenyl)-4-tert-butyl-pyrido[3,2-d]pyrimidine,
  6-(4-fluorophenyl)-4-hexyl-pyrido[3,2-d]pyrimidine,
  6-(4-fluorophenyl)-4-heptyl-pyrido[3,2-d]pyrimidine,
  6-(4-fluorophenyl)-4-octyl-pyrido[3,2-d]pyrimidine,
  6-(4-fluorophenyl)-4-decyl-pyrido[3,2-d]pyrimidine,
  6-(4-fluorophenyl)-4-allyl-pyrido[3,2-d]pyrimidine,
  6-(4-fluorophenyl)-4-ethynyl-pyrido[3,2-d]pyrimidine,
  6-(4-fluorophenyl)-4-vinyl-pyrido[3,2-d]pyrimidine,
  6-(4-fluorophenyl)-4-(4-but-3-enyl)-pyrido[3,2-d]pyrimidine,
  6-(4-fluorophenyl)-4-methyl-pyrido[3,2-d]pyrimidin-2-ylamine,
  6-(4-fluorophenyl)-4-ethyl-pyrido[3,2-d]pyrimidin-2-ylamine,
  6-(4-fluorophenyl)-4-isopropyl-pyrido[3,2-d]pyrimidin-2-ylamine,
  6-(4-fluorophenyl)-4-isobutyl-pyrido[3,2-d]pyrimidin-2-ylamine,
  6-(4-fluorophenyl)-4-pentyl-pyrido[3,2-d]pyrimidin-2-ylamine,
  6-(4-fluorophenyl)-4-tert-butyl-pyrido[3,2-d]pyrimidin-2-ylamine,
  6-(4-fluorophenyl)-4-hexyl-pyrido[3,2-d]pyrimidin-2-ylamine,
  6-(4-fluorophenyl)-4-heptyl-pyrido[3,2-d]pyrimidin-2-ylamine,
  6-(4-fluorophenyl)-4-octyl-pyrido[3,2-d]pyrimidin-2-ylamine,
  6-(4-fluorophenyl)-4-decyl-pyrido[3,2-d]pyrimidin-2-ylamine,
  6-(4-fluorophenyl)-4-allyl-pyrido[3,2-d]pyrimidin-2-ylamine,
  6-(4-fluorophenyl)-4-ethynyl-pyrido[3,2-d]pyrimidin-2-ylamine,
  6-(4-fluorophenyl)-4-vinyl-pyrido[3,2-d]pyrimidin-2-ylamine,
  6-(4-fluorophenyl)-4-(4-but-3-enyl)-pyrido[3,2-d]pyrimidin-2-ylamine,
  4-n-propyl-6-(3-aminocarbonylphenyl)pyrido[3,2-d]pyrimidin-2-ylamine,
  4-n-propyl-6-(4-aminocarbonylphenyl)pyrido[3,2-d]pyrimidin-2-ylamine,
  4-n-propyl-6-(2-amino-5-chlorophenyl)pyrido[3,2-d]pyrimidin-2-ylamine,
  4-n-propyl-6-(4-amino-3-methoxyphenyl)pyrido[3,2-d]pyrimidin-2-ylamine,
  4-n-propyl-6-(2-amino-4-methylphenyl)pyrido[3,2-d]pyrimidin-2-ylamine,
  4-n-propyl-6-(2-amino-5-methylphenyl)pyrido[3,2-d]pyrimidin-2-ylamine,
  4-n-propyl-6-(4-amino-2-methyl phenyl)pyrido[3,2-d]pyrimidin-2-ylamine,
  4-n-propyl-6-(5-amino-2-methyl phenyl)pyrido[3,2-d]pyrimidin-2-ylamine,
  4-n-propyl-6-(4-amino-3-nitrophenyl)pyrido[3,2-d]pyrimidin-2-ylamine,
  4-n-propyl-6-(2-benzyloxyphenyl)pyrido[3,2-d]pyrimidin-2-ylamine,
  4-n-propyl-6-(3-benzyloxy-4-methoxyphenyl)pyrido[3,2-d]pyrimidin-2-ylamine,
  4-n-propyl-6-(4-n-butyl phenyl)pyrido[3,2-d]pyrimidin-2-ylamine,
  4-n-propyl-6-(4-isobutylphenyl)pyrido[3,2-d]pyrimidin-2-ylamine,
  4-n-propyl-6-(4-carboxy-3-fluorophenyl)pyrido[3,2-d]pyrimidin-2-ylamine,
  4-n-propyl-6-(3-(3-carboxypropionylamino)phenyl)pyrido[3,2-d]pyrimidin-2-ylamine,
  4-n-propyl-6-(4-(3-carboxypropionylamino)phenyl)pyrido[3,2-d]pyrimidin-2-ylamine,
  4-n-propyl-6-(3-chloro-4-hydroxy-5-methoxyphenyl)pyrido[3,2-d]pyrimidin-2-ylamine, 4-n-propyl-6-(2-chloro-5-hydroxymethylphenyl)pyrido[3,2-d]pyrimidin-2-ylamine,
4-n-propyl-6-(4-cyanomethoxyphenyl)pyrido[3,2-d]pyrimidin-2-ylamine,
4-n-propyl-6-(3-cyanomethoxyphenyl)pyrido[3,2-d]pyrimidin-2-ylamine,
4-n-propyl-6-(2-cyanomethoxyphenyl)pyrido[3,2-d]pyrimidin-2-ylamine,
4-n-propyl-6-(4-cyanophenyl)pyrido[3,2-d]pyrimidin-2-ylamine,
4-n-propyl-6-(3-cyanophenyl)pyrido[3,2-d]pyrimidin-2-ylamine,
4-n-propyl-6-(2-cyanophenyl)pyrido[3,2-d]pyrimidin-2-ylamine,
4-n-propyl-6-(3-(N-cyclopropylaminocarbonyl)phenyl)pyrido[3,2-d]pyrimidin-2-ylamine,
4-n-propyl-6-(3-(N,N-diethylaminocarbonyl)phenyl)pyrido[3,2-d]pyrimidin-2-ylamine,
4-n-propyl-6-(3-(N,N-dimethylamino)phenyl)pyrido[3,2-d]pyrimidin-2-ylamine,
4-n-propyl-6-(2-(N,N-dimethylamino)phenyl)pyrido[3,2-d]pyrimidin-2-ylamine,
4-n-propyl-6-(3-(N,N-dimethylaminocarbonyl)phenyl)pyrido[3,2-d]pyrimidin-2-ylamine,
4-n-propyl-6-(3-[(N,N-dimethylamino)ethylaminocarbonyl]phenyl)-pyrido[3,2-d]pyrimidin-2-ylamine,
4-n-propyl-6-(4-[(N,N-dimethylamino)ethylaminocarbonyl]phenyl)-pyrido[3,2-d]pyrimidin-2-ylamine,
4-n-propyl-6-(3-[1,3]dioxolan-2-ylmethoxyphenyl)pyrido[3,2-d]pyrimidin-2-ylamine,
4-n-propyl-6-(3-(ethoxycarbonyl)methoxyphenyl)pyrido[3,2-d]pyrimidin-2-ylamine,
4-n-propyl-6-(4-(ethoxycarbonyl)methoxyphenyl)pyrido[3,2-d]pyrimidin-2-ylamine,
4-n-propyl-6-(4-ethoxycarbonylphenyl)pyrido[3,2-d]pyrimidin-2-ylamine,
4-n-propyl-6-(3-ethoxycarbonylphenyl)pyrido[3,2-d]pyrimidin-2-ylamine,
4-n-propyl-6-(2-ethoxycarbonylphenyl)pyrido[3,2-d]pyrimidin-2-ylamine,
4-n-propyl-6-(4-(3-ethoxycarbonylpiperidino)carboxamidophenyl)-pyrido[3,2-d]pyrimidin-2-ylamine,
4-n-propyl-6-(4-formylaminophenyl)pyrido[3,2-d]pyrimidin-2-ylamine,
4-n-propyl-6-(3-formylaminophenyl)pyrido[3,2-d]pyrimidin-2-ylamine,
4-n-propyl-6-(2-formylaminophenyl)pyrido[3,2-d]pyrimidin-2-ylamine,
4-n-propyl-6-(2-formyl-5-methoxyphenyl)pyrido[3,2-d]pyrimidin-2-ylamine,
4-n-propyl-6-(3-formyl-4-methoxyphenyl)pyrido[3,2-d]pyrimidin-2-ylamine,
4-n-propyl-6-(5-formyl-2-methoxyphenyl)pyrido[3,2-d]pyrimidin-2-ylamine,
4-n-propyl-6-(2-formyl-5-methylphenyl)pyrido[3,2-d]pyrimidin-2-ylamine,
4-n-propyl-6-(4-formylphenyl)pyrido[3,2-d]pyrimidin-2-ylamine,
4-n-propyl-6-(3-formylphenyl)pyrido[3,2-d]pyrimidin-2-ylamine,
4-n-propyl-6-(2-formylphenyl)pyrido[3,2-d]pyrimidin-2-ylamine,
4-n-propyl-6-(4-hydroxy-3,5-dimethylphenyl)pyrido[3,2-d]pyrimidin-2-ylamine,
4-n-propyl-6-(3-(2-hydroxyethyl)-aminocarbonylphenyl)pyrido[3,2-d]pyrimidin-2-ylamine,
4-n-propyl-6-(4-(2-hydroxyethyl)aminocarbonyl)phenyl)pyrido[3,2-d]pyrimidin-2-ylamine,
4-n-propyl-6-(3-hydroxy-4-methoxycarbonylphenyl)pyrido[3,2-d]pyrimidin-2-ylamine,
4-n-propyl-6-(4-hydroxy-3-methoxyphenyl)pyrido[3,2-d]pyrimidin-2-ylamine,
4-n-propyl-6-(4-(hydroxymethyl)phenyl)pyrido[3,2-d]pyrimidin-2-ylamine,
4-n-propyl-6-(3-(hydroxymethyl)phenyl)pyrido[3,2-d]pyrimidin-2-ylamine,
4-n-propyl-6-(4-hydroxy-3-nitrophenyl)pyrido[3,2-d]pyrimidin-2-ylamine,
4-n-propyl-6-(4-isopropoxyphenyl)pyrido[3,2-d]pyrimidin-2-ylamine,
4-n-propyl-6-(4-(4-isopropylpiperazinyl)phenyl)pyrido[3,2-d]pyrimidin-2-ylamine,
4-n-propyl-6-(4-isopropylphenyl)pyrido[3,2-d]pyrimidin-2-ylamine,
4-n-propyl-6-(4-methanesulfonamidophenyl)pyrido[3,2-d]pyrimidin-2-ylamine,
4-n-propyl-6-(3-methanesulfonamidophenyl)pyrido[3,2-d]pyrimidin-2-ylamine,
4-n-propyl-6-(2-methanesulfonamido phenyl)pyrido[3,2-d]pyrimidin-2-ylamine,
4-n-propyl-6-(4-methoxycarbonylphenyl)pyrido[3,2-d]pyrimidin-2-ylamine,
4-n-propyl-6-(3-methoxycarbonylphenyl)pyrido[3,2-d]pyrimidin-2-ylamine,
4-n-propyl-6-(2-methoxycarbonylphenyl)pyrido[3,2-d]pyrimidin-2-ylamine,
4-n-propyl-6-(3-methoxy-4-methoxycarbonylphenyl)pyrido[3,2-d]pyrimidin-2-ylamine,
4-n-propyl-6-(2-methoxy-5-methylphenyl)pyrido[3,2-d]pyrimidin-2-ylamine,
4-n-propyl-6-(4-methoxy-3-nitrophenyl)pyrido[3,2-d]pyrimidin-2-ylamine,
4-n-propyl-6-(4-methoxyphenyl)pyrido[3,2-d]pyrimidin-2-ylamine,
4-n-propyl-6-(3-methoxyphenyl)pyrido[3,2-d]pyrimidin-2-ylamine,
4-n-propyl-6-(4-(4-methylpiperazine-1-carbonyl)phenyl)pyrido[3,2-d]pyrimidin-2-ylamine,
4-n-propyl-6-(4-(methylthio)phenyl)pyrido[3,2-d]pyrimidin-2-ylamine,
4-n-propyl-6-(3-(methylthio)phenyl)pyrido[3,2-d]pyrimidin-2-ylamine,
4-n-propyl-6-(2-(methylthio)phenyl)pyrido[3,2-d]pyrimidin-2-ylamine,
4-n-propyl-6-(4-(morpholinocarbonyl)phenyl)pyrido[3,2-d]pyrimidin-2-ylamine,
4-n-propyl-6-(4-morpholinophenyl)pyrido[3,2-d]pyrimidin-2-ylamine,
4-n-propyl-6-(2-(morpholinomethyl)phenyl)pyrido[3,2-d]pyrimidin-2-ylamine,
4-n-propyl-6-(4-nitrophenyl)pyrido[3,2-d]pyrimidin-2-ylamine,
4-n-propyl-6-(3-nitrophenyl)pyrido[3,2-d]pyrimidin-2-ylamine,
4-n-propyl-6-(2-nitrophenyl)pyrido[3,2-d]pyrimidin-2-ylamine,
4-n-propyl-6-(4-phenoxyphenyl)pyrido[3,2-d]pyrimidin-2-ylamine,
4-n-propyl-6-(4-(N-phenylaminomethyl)phenyl)pyrido[3,2-d]pyrimidin-2-ylamine,
4-n-propyl-6-(4-(phenylcarbonyl)phenyl)pyrido[3,2-d]pyrimidin-2-ylamine, 4-n-propyl-6-(4-(piperazine-1-carbonyl)phenyl)pyrido[3,2-d]pyrimidin-2-ylamine,
4-n-propyl-6-(4-piperazinylphenyl)pyrido[3,2-d]pyrimidin-2-ylamine,
4-n-propyl-6-(4-succinamidophenyl)pyrido[3,2-d]pyrimidin-2-ylamine,
4-n-propyl-6-(3-succinamidophenyl)pyrido[3,2-d]pyrimidin-2-ylamine,
4-n-propyl-6-(sulfamoylphenyl)pyrido[3,2-d]pyrimidin-2-ylamine,
4-n-propyl-6-(2-(toluene-4-sulfonamido)phenyl)pyrido[3,2-d]pyrimidin-2-ylamine,
4-n-propyl-6-(4-(toluene-4-sulfonamido)phenyl)pyrido[3,2-d]pyrimidin-2-ylamine,
4-n-propyl-6-(4-(tert-butoxycarbonylamino)-3-methoxyphenyl)pyrido[3,2-d]pyrimidin-2-ylamine,
4-n-propyl-6-(2-(tert-butoxycarbonyl)phenyl)pyrido[3,2-d]pyrimidin-2-ylamine,
4-n-propyl-6-(3-(tert-butoxycarbonyl)phenyl)pyrido[3,2-d]pyrimidin-2-ylamine,
4-n-propyl-6-(4-(tert-butoxycarbonyl)phenyl)pyrido[3,2-d]pyrimidin-2-ylamine,
4-n-propyl-6-(2,3,4-trifluorophenyl)pyrido[3,2-d]pyrimidin-2-ylamine,
4-n-propyl-6-(4-tert-butylphenyl)pyrido[3,2-d]pyrimidin-2-ylamine,
4-n-propyl-6-(4-(tetrahydro-2H-pyran-2-yloxy)phenyl)pyrido[3,2-d]pyrimidin-2-ylamine,
4-n-propyl-6-(4-(2-thienyl)phenyl)pyrido[3,2-d]pyrimidin-2-ylamine,
4-n-propyl-6-(2,4,6-trimethylphenyl)pyrido[3,2-d]pyrimidin-2-ylamine,
4-n-propyl-6-(3,4,5-trimethoxyphenyl)pyrido[3,2-d]pyrimidin-2-ylamine,
4-n-propyl-6-(4-vinylphenyl)pyrido[3,2-d]pyrimidin-2-ylamine,
4-n-propyl-6-(4-(2-hydroxyethoxy)phenyl)pyrido[3,2-d]pyrimidin-2-ylamine,
4-n-propyl-6-(6-benzyloxynaphth-2-yl)pyrido[3,2-d]pyrimidin-2-ylamine,
4-n-propyl-6-(naphth-1-yl)pyrido[3,2-d]pyrimidin-2-ylamine,
4-n-propyl-6-(naphth-2-yl)pyrido[3,2-d]pyrimidin-2-ylamine,
4-n-propyl-6-(4'-benzoyl[1,1'-biphenyl]-4-yl)pyrido[3,2-d]pyrimidin-2-ylamine,
4-n-propyl-6-(oxoindan-5-yl)pyrido[3,2-d]pyrimidin-2-ylamine,
4-n-propyl-6-(benzodioxolyl)pyrido[3,2-d]pyrimidin-2-ylamine,
4-n-propyl-6-(2-acetamidopyridin-5-yl)pyrido[3,2-d]pyrimidin-2-ylamine,
4-n-propyl-6-(2-aminopyridin-5-yl)pyrido[3,2-d]pyrimidin-2-ylamine,
4-n-propyl-6-(2-aminopyrido[3,2-d]pyrimidin-5-yl)pyrido[3,2-d]pyrimidin-2-ylamine,
4-n-propyl-6-(1,4-benzodioxan-6-yl)pyrido[3,2-d]pyrimidin-2-ylamine,
4-n-propyl-6-(1-benzothien-3-yl)pyrido[3,2-d]pyrimidin-2-ylamine,
4-n-propyl-6-(2-benzyloxypyridin-5-yl)pyrido[3,2-d]pyrimidin-2-ylamine,
4-n-propyl-6-(1-benzyl-1H-pyrazol-4-yl)pyrido[3,2-d]pyrimidin-2-ylamine,
4-n-propyl-6-(2-bromo-3-chloropyridin-4-yl)pyrido[3,2-d]pyrimidin-2-ylamine,
4-n-propyl-6-(5-bromo-2,3-dihydrobenzo[b]furan-7-yl)pyrido[3,2-d]pyrimidin-2-ylamine,
4-n-propyl-6-(2-bromo-3-methylpyridin-5-yl)pyrido[3,2-d]pyrimidin-2-ylamine,
4-n-propyl-6-(2-bromopyridin-5-yl)pyrido[3,2-d]pyrimidin-2-ylamine,
4-n-propyl-6-(3-bromopyridin-5-yl)pyrido[3,2-d]pyrimidin-2-ylamine,
4-n-propyl-6-(5-bromothien-2-yl)pyrido[3,2-d]pyrimidin-2-ylamine,
4-n-propyl-6-(2-chloro-6-isopropylpyridin-3-yl)pyrido[3,2-d]pyrimidin-2-ylamine,
4-n-propyl-6-(2-chloro-3-methylpyridin-5-yl)pyrido[3,2-d]pyrimidin-2-ylamine,
4-n-propyl-6-(2-[4-(4-chlorophenylsulfonyl)piperazin-1-yl]pyridin-5-yl)pyrido[3,2-d]pyrimidin-2-ylamine,
4-n-propyl-6-(2-chloropyrid-4-yl)pyrido[3,2-d]pyrimidin-2-ylamine,
4-n-propyl-6-(2-chloropyrid-5-yl)pyrido[3,2-d]pyrimidin-2-ylamine,
4-n-propyl-6-(dibenzo[b,d]furan-4-yl)pyrido[3,2-d]pyrimidin-2-ylamine,
4-n-propyl-6-(2-chloro-3-fluoropyridin-4-yl)pyrido[3,2-d]pyrimidin-2-ylamine,
4-n-propyl-6-(dibenzo[b,d]thien-4-yl)pyrido[3,2-d]pyrimidin-2-ylamine,
4-n-propyl-6-(3,4-dihydro-2H-1,5-benzodioxepin-7-yl)pyrido[3,2-d]pyrimidin-2-ylamine,
4-n-propyl-6-(3,6-dihydro-2H-pyridine-1-tert-butoxycarbonyl)pyrido[3,2-d]pyrimidin-2-ylamine,
4-n-propyl-6-(2,5-dibromopyridin-3-yl)pyrido[3,2-d]pyrimidin-2-ylamine,
4-n-propyl-6-(2,6-dichloropyridin-3-yl)pyrido[3,2-d]pyrimidin-2-ylamine,
4-n-propyl-6-(2,3-dihydro-1-benzofuran-5-yl)pyrido[3,2-d]pyrimidin-2-ylamine,
4-n-propyl-6-(2,6-dimethoxypyridin-5-yl)pyrido[3,2-d]pyrimidin-2-ylamine,
4-n-propyl-6-(2,6-dimethoxypyridin-3-yl)pyrido[3,2-d]pyrimidin-2-ylamine,
4-n-propyl-6-(2,4-dimethoxypyrido[3,2-d]pyrimidin-5-yl)pyrido[3,2-d]pyrimidin-2-ylamine,
4-n-propyl-6-(3,5-dimethylisoxazol-4-yl)pyrido[3,2-d]pyrimidin-2-ylamine,
4-n-propyl-6-(2-(3-N,N-dimethylaminopropoxy)pyridin-5-yl)pyrido[3,2-d]pyrimidin-2-ylamine,
4-n-propyl-6-(3,5-dimethylpyrazol-4-yl)pyrido[3,2-d]pyrimidin-2-ylamine,
4-n-propyl-6-(1-[1,3]dioxolan-2-ylmethyl-1H-pyrazol-4-yl)pyrido[3,2-d]pyrimidin-2-ylamine,
4-n-propyl-6-(2,4-dioxo-1,2,3,4-tetrahydro-5-pyrido[3,2-d]pyrimidinyl)pyrido[3,2-d]pyrimidin-2-ylamine,
4-n-propyl-6-(2,4-di(tert-butoxy)pyrido[3,2-d]pyrimidin-5-yl)pyrido[3,2-d]pyrimidin-2-ylamine,
4-n-propyl-6-(2-ethoxypyridin-3-yl)pyrido[3,2-d]pyrimidin-2-ylamine,
4-n-propyl-6-(2-fluoro-3-methylpyridin-5-yl)pyrido[3,2-d]pyrimidin-2-ylamine,
4-n-propyl-6-(2-fluoropyridin-5-yl)pyrido[3,2-d]pyrimidin-2-ylamine,
4-n-propyl-6-(5-formyl-2-furyl)pyrido[3,2-d]pyrimidin-2-ylamine,
4-n-propyl-6-(5-formylthien-2-yl)pyrido[3,2-d]pyrimidin-2-ylamine,
4-n-propyl-6-(furan-2-yl)pyrido[3,2-d]pyrimidin-2-ylamine, 4-n-propyl-6-(2-hydroxypyridin-5-yl)pyrido[3,2-d]pyrimidin-2-ylamine,
4-n-propyl-6-(1-isobutyl-1H-pyrazol-4-yl)pyrido[3,2-d]pyrimidin-2-ylamine,
4-n-propyl-6-(isoquinolin-4-yl)pyrido[3,2-d]pyrimidin-2-ylamine,
4-n-propyl-6-(2-methoxypyridin-3-yl)pyrido[3,2-d]pyrimidin-2-ylamine,
4-n-propyl-6-(2-methoxypyrido[3,2-d]pyrimidin-5-yl)pyrido[3,2-d]pyrimidin-2-ylamine,
4-n-propyl-6-(5-methyl-1-benzothien-2-yl)pyrido[3,2-d]pyrimidin-2-ylamine,
4-n-propyl-6-(1-(3-methylbutyl)-1H-pyrazol-4-yl)pyrido[3,2-d]pyrimidin-2-ylamine,
4-n-propyl-6-(5-methylfuran-2-yl)pyrido[3,2-d]pyrimidin-2-ylamine,
4-n-propyl-6-(1-methylindol-5-yl)pyrido[3,2-d]pyrimidin-2-ylamine,
4-n-propyl-6-(5-methyl-3-phenyl-4-isoxazolyl)pyrido[3,2-d]pyrimidin-2-ylamine,
4-n-propyl-6-(5-(methylthio)thien-2-yl)pyrido[3,2-d]pyrimidin-2-ylamine,
4-n-propyl-6-(2-(4-methylpiperazinyl)pyridin-4-yl)pyrido[3,2-d]pyrimidin-2-ylamine,
4-n-propyl-6-(2-(4-methylpiperazinyl)pyridin-5-yl)pyrido[3,2-d]pyrimidin-2-ylamine,
4-n-propyl-6-(1-methyl-1H-pyrazol-4-yl)pyrido[3,2-d]pyrimidin-2-ylamine,
4-n-propyl-6-(3-methylpyridin-2-yl)pyrido[3,2-d]pyrimidin-2-ylamine,
4-n-propyl-6-(5-methylpyridin-2-yl)pyrido[3,2-d]pyrimidin-2-ylamine,
4-n-propyl-6-(5-methylpyridin-3-yl)pyrido[3,2-d]pyrimidin-2-ylamine,
4-n-propyl-6-(2-methoxypyridin-5-yl)pyrido[3,2-d]pyrimidin-2-ylamine,
4-n-propyl-6-(4-methylthien-2-yl)pyrido[3,2-d]pyrimidin-2-ylamine,
4-n-propyl-6-(5-methylthien-2-yl)pyrido[3,2-d]pyrimidin-2-ylamine,
4-n-propyl-6-(2-(2-morpholinoethylamino)-pyridin-5-yl)pyrido[3,2-d]pyrimidin-2-ylamine,
4-n-propyl-6-(2-(2-morpholinoethyl)-1H-pyrazol-4-yl)pyrido[3,2-d]pyrimidin-2-ylamine,
4-n-propyl-6-(2-(morpholin-1-yl)-pyridin-5-yl)pyrido[3,2-d]pyrimidin-2-ylamine,
4-n-propyl-6-(1-(phenylsulfonyl)-1H-indol-3-yl)pyrido[3,2-d]pyrimidin-2-ylamine,
4-n-propyl-6-(5-phenyl-2-thienyl)pyrido[3,2-d]pyrimidin-2-ylamine,
4-n-propyl-6-(2-(piperazin-1-yl)-pyridin-5-yl)pyrido[3,2-d]pyrimidin-2-ylamine,
4-n-propyl-6-(2-(piperazin-1-yl)-pyridin-4-yl)pyrido[3,2-d]pyrimidin-2-ylamine,
4-n-propyl-6-(1-propyl-1H-pyrazol-4-yl)pyrido[3,2-d]pyrimidin-2-ylamine,
4-n-propyl-6-(pyrazol-4-yl)pyrido[3,2-d]pyrimidin-2-ylamine,
4-n-propyl-6-(pyridin-4-yl)pyrido[3,2-d]pyrimidin-2-ylamine,
4-n-propyl-6-(4-phenoxathiinyl)pyrido[3,2-d]pyrimidin-2-ylamine,
4-n-propyl-6-(quinolin-8-yl)pyrido[3,2-d]pyrimidin-2-ylamine,
4-n-propyl-6-(quinolin-3-yl)pyrido[3,2-d]pyrimidin-2-ylamine,
4-n-propyl-6-(2-(4-tert-butoxycarbonylpiperazinyl)-pyrid-4-yl)pyrido[3,2-d]pyrimidin-2-ylamine,
4-n-propyl-6-(1-tert-butoxycarbonyl-1H-pyrazol-4-yl)pyrido[3,2-d]pyrimidin-2-ylamine,
4-n-propyl-6-(1-tert-butoxycarbonyl-2-pyrrolyl)pyrido[3,2-d]pyrimidin-2-ylamine,
4-n-propyl-6-(1-(tert-butoxycarbonyl)-5-bromo-1H-indol-2-yl)pyrido[3,2-d]pyrimidin-2-ylamine,
4-n-propyl-6-(1-(tert-butoxycarbonyl)-1H-indol-5-yl)pyrido[3,2-d]pyrimidin-2-ylamine,
4-n-propyl-6-(1-(tert-butoxycarbonyl)-5-methoxy-1H-indol-2-yl)pyrido[3,2-d]pyrimidin-2-ylamine,
4-n-propyl-6-(1-thianthrenylthien-3-yl)pyrido[3,2-d]pyrimidin-2-ylamine,
4-n-propyl-6-(1,3,5-trimethyl-1H-pyrazol-4-yl)pyrido[3,2-d]pyrimidin-2-ylamine,
4-phenyl-6-(4-(4'-allyloxycarbonylpiperazino)phenyl)pyrimidin-2-ylamine and pharmaceutical acceptable addition salts, stereochemical isomeric forms, and N-oxides thereof.

10. A pharmaceutical composition comprising one or more pharmaceutically acceptable carriers and a pyrido(3,2-d)pyrimidine derivative according to claim 1.

11. A pharmaceutical composition according to claim 10, further comprising one or more antiviral agents.

12. A method of treatment of a viral infection due to a member of the Flaviridae family, comprising the administration to a patient in need thereof of a therapeutically effective amount of a pyrido(3,2-d)pyrimidine derivative according to claim 1.

13. A method of treatment of a viral infection according to claim 12, wherein said viral infection is due to hepatitis C virus.

14. A method of prevention or treatment of a viral infection according to claim 12, wherein said patient is a human being and said effective amount ranges from 0.01 mg to 20 mg per day per kg bodyweight.

15. A method of making a pyrido(3,2-d)pyrimidine derivative according to claim 1, comprising a step of reacting a pyrido(3,2-d)pyrimidine intermediate represented by the structural formula:

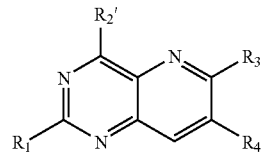

wherein:
  $R_1, R_3, R_4, R_6, R_7, R_8, R_8', R_9, R_9', R_{10}, R_{11}, R_{12}, R_{13}$ and $R_{14}$ are defined as in claim 1; and
  $R_2'$ is a nitrogen-containing aromatic heterocyclyl group attached through the nitrogen atom to position 4 of the pyrido(3,2-d)pyrimidinyl moiety,
with at least one organometallic reagent of the formula $R_2MZ$ wherein $R_2$ is defined as in claim 1, M is a metal selected from the group consisting of magnesium, calcium, zinc and manganese, and Z is an anionic ligand, in the presence of at least one catalyst comprising one or more iron salts or complexes to make the pyrido(3,2-d)pyrimidine derivative.

16. A method according to claim 15, wherein $R_2'$ is selected from the group consisting of 1,2,4-triazolyl, 1,2,3-triazolyl, 1H-tetrazolyl, 4-dimethylaminopyridyl and 2-diethylaminopyridyl.

17. A method according to claim 15, wherein said anionic ligand Z is selected from the group consisting of halogen, $C_{1-7}$ alkyl and aryl.

18. A method according to claim 15, wherein said reaction step is performed in a solvent medium containing one or more ethers and/or hydrocarbons.

19. A method according to claim 15, wherein said organometallic reagent is a Grignard reagent wherein M is magnesium and Z is halogen.

20. A method according to claim 15, wherein said organometallic reagent is a diorganomagnesium reagent wherein M is magnesium, $R_2$ is $C_{1-7}$ alkyl and wherein Z is $C_{1-7}$ alkyl.

* * * * *

UNITED STATES PATENT AND TRADEMARK OFFICE
CERTIFICATE OF CORRECTION

PATENT NO. : 8,338,435 B2  
APPLICATION NO. : 12/374223  
DATED : December 25, 2012  
INVENTOR(S) : Herdewijn et al.

It is certified that error appears in the above-identified patent and that said Letters Patent is hereby corrected as shown below:

Title page item (22), replace "Jun. 20, 2007" with --Jul. 20, 2007--;

In the claims,

Column 74, Claim 1, Line 21, replace "–CO–$NR_9R_9$," with -- –CO–$NR_9R_{9'}$,--.

Column 77, Claim 9, Line 26, replace "[(N,N-dimethylamino)" with --[(N',N'-dimethylamino)--;

Line 28, replace "[(N,N-dimethylamino)" with --[(N',N'-dimethylamino)--.

Column 82, Claim 14, Line 37, replace "A method of prevention or treatment of" with --A method of treatment of--.

Signed and Sealed this  
Twelfth Day of May, 2015

Michelle K. Lee  
*Director of the United States Patent and Trademark Office*